United States Patent
Mutahi et al.

(10) Patent No.: US 7,638,531 B2
(45) Date of Patent: Dec. 29, 2009

(54) PHENOXYPIPERIDINES AND ANALOGS THEREOF USEFUL AS HISTAMINE $H_3$ ANTAGONISTS

(75) Inventors: Mwangi W. Mutahi, Nyeri (KE); Robert G. Aslanian, Rockaway, NJ (US); Michael Y. Berlin, Flemington, NJ (US); Christopher W. Boyce, Flemington, NJ (US); Manuel de Lera Ruiz, Branchburg, NJ (US); Kevin D. McCormick, Basking Ridge, NJ (US); Daniel M. Solomon, Edison, NJ (US); Henry A. Vaccaro, South Plainfield, NJ (US); Junying Zheng, Bridgewater, NJ (US); Purakkattle Biju, Piscataway, NJ (US); Younong Yu, East Brunswick, NJ (US); Wei Zhou, Scotch Plains, NJ (US); Xiaohong Zhu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 171 days.

(21) Appl. No.: 11/641,175

(22) Filed: Dec. 19, 2006

(65) Prior Publication Data
US 2007/0167435 A1 Jul. 19, 2007

Related U.S. Application Data

(60) Provisional application No. 60/752,636, filed on Dec. 21, 2005.

(51) Int. Cl.
| | |
|---|---|
| A01N 43/42 | (2006.01) |
| A61K 31/44 | (2006.01) |
| A01N 43/40 | (2006.01) |
| C07D 471/02 | (2006.01) |
| C07D 491/02 | (2006.01) |
| C07D 498/02 | (2006.01) |
| C07D 211/68 | (2006.01) |
| C07D 211/80 | (2006.01) |
| C07D 213/02 | (2006.01) |

(52) U.S. Cl. ............ 514/303; 514/318; 546/118; 546/194

(58) Field of Classification Search .......... 544/242; 514/256, 303, 318; 546/118, 194
See application file for complete search history.

(56) References Cited

U.S. PATENT DOCUMENTS

| | | | |
|---|---|---|---|
| 5,242,924 A * | 9/1993 | Diana | 514/252.03 |
| 5,364,865 A * | 11/1994 | Diana | 514/318 |
| 5,869,479 A | 2/1999 | Kreutner et al. | |
| 6,720,328 B2 | 4/2004 | Aslanian et al. | |
| 6,849,621 B2 | 2/2005 | Rosenblum et al. | |

(Continued)

FOREIGN PATENT DOCUMENTS

| | | |
|---|---|---|
| EP | 0 157 145 B1 | 10/1985 |
| WO | WO 03/088967 A1 | 10/2003 |
| WO | 2004/069816 * | 8/2004 |
| WO | WO 2004/089373 A1 | 10/2004 |
| WO | WO 2004/101546 A1 | 11/2004 |
| WO | 2005/012293 * | 2/2005 |
| WO | WO 2006/124748 A2 | 11/2006 |

OTHER PUBLICATIONS

Hancock et al., "Cognitive enhancing effects of drugs that target histamine receptors", *Cognitive Enhancing Drugs*, Edited by J. J. Buccafusco, Birkhauser, Basel pp. 97-114 (2004).

(Continued)

*Primary Examiner*—D. Margaret Seaman
*Assistant Examiner*—Niloofar Rahmani
(74) *Attorney, Agent, or Firm*—Jeffrey P. Bergman

(57) ABSTRACT

Disclosed are compounds of the formula (I)

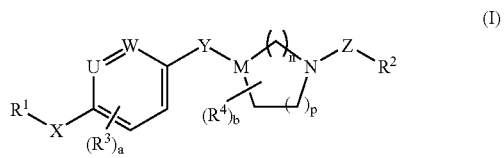

or a pharmaceutically acceptable salt or solvate thereof, wherein:

M is CH or N;
U and W are each CH, or one of U and W is CH and the other is N;
X is a bond, alkylene, —C(O)—, —C(N—OR$^5$)—, —C(N—OR$^5$)—CH(R$^6$)—, —CH(R$^6$)—C(N—OR$^5$)—, —O—, —OCH$_2$—, —CH$_2$O— or —S(O)$_{0-2}$—;
Y is —O—, —(CH$_2$)$_2$—, —C(=O)—, —C(=NOR$^7$)— or —SO$_{0-2}$—;
Z is a bond, optionally substituted alkylene or alkylene interrupted by a heteroatom or heterocyclic group;
R$^1$ is optionally substituted alkyl, cycloalkyl, aryl, arylalkyl, heteroaryl, heterocycloalkyl, or benzimidazolyl or a derivative thereof;
R$^2$ is optionally substituted alkyl, alkenyl, aryl, arylalkyl, heteroaryl, heteroarylalkyl, cycloalkyl or heterocycloalkyl;
and the remaining variables are as defined in the specification;

compositions and methods for treating an allergy-induced airway response, congestion, diabetes, obesity, an obesity-related disorder, metabolic syndrome and a cognition deficit disorder using said compounds, alone or in combination with other agents.

18 Claims, No Drawings

U.S. PATENT DOCUMENTS

| | | |
|---|---|---|
| 2004/0019039 A1 | 1/2004 | Dorwald et al. |
| 2004/0019099 A1 | 1/2004 | Aslanian et al. |
| 2004/0048843 A1 | 3/2004 | Ting et al. |
| 2004/0097483 A1 | 5/2004 | Zeng et al. |
| 2004/0224953 A1 | 11/2004 | Cowart et al. |

OTHER PUBLICATIONS

Ley et al., "A Rapid Approach for the Optimisation of Polymer Supported Reagents in Synthesis", Synlett, 11:1603-1607 (2000).

Leurs et al., "The Histamine $H_3$ Receptor: From Gene Cloning to $H_3$ Receptor Drugs", *Nature Reviews Drug* Discovery, 4(2):107-120 (Feb. 2005).

Morgan et al., "Synthesis and Cardiac Electrophysiological Activity of N-Substituted-4-(1H-imidazol-1-yl) benzamides—New Selective Case III Agents", *J. Med. Chem.*, 33:1091-1097 (1990).

Tashiro et al., "Roles of histamine in regulation of arousal and cognition: functional neuroimaging of histamine H1 receptors in human brain", *Life Sciences,* 72:409-414 (2002).

International Search Report for corresponding PCT Application No. PCT/US2006/1048349 dated Aug. 1, 2007.

\* cited by examiner

_US 7,638,531 B2_

PHENOXYPIPERIDINES AND ANALOGS THEREOF USEFUL AS HISTAMINE H$_3$ ANTAGONISTS

This application claims the benefit of U.S. Provisional Application No. 60/752,636, filed Dec. 21, 2005, which is incorporated by reference herein in its entirety.

FIELD OF THE INVENTION

The present invention relates to phenoxypiperidines and analogs thereof useful as histamine H$_3$ antagonists. The invention also relates to pharmaceutical compositions comprising said compounds and their use in treating inflammatory diseases, allergic conditions, diabetes, obesity, an obesity-related disorder, metabolic syndrome, a cognition deficit disorder, cardiovascular and central nervous system disorders. The invention also relates to the use of a combination of histamine H$_3$ antagonists of this invention with histamine H$_1$ compounds for the treatment of inflammatory diseases and allergic conditions, as well to the use of a combination of an histamine H$_3$ antagonist of this invention with other actives useful for treating diabetes, obesity, an obesity-related disorder, metabolic syndrome or a cognition deficit disorder. Pharmaceutical compositions comprising a combination of at least one novel histamine H$_3$ antagonist compound of the invention with at least one histamine H$_1$ compound or at least one compound useful for treating diabetes, obesity, an obesity-related disorder, metabolic syndrome or a cognition deficit disorder are also contemplated.

BACKGROUND OF THE INVENTION

The histamine receptors, H$_1$, H$_2$, H$_3$ and H$_4$ have been characterized by their pharmacological behavior. The H$_1$ receptors are those that mediate the response antagonized by conventional antihistamines. H$_1$ receptors are present, for example, in the ileum, the skin, and the bronchial smooth muscle of humans and other mammals. The most prominent H$_2$ receptor-mediated responses are the secretion of gastric acid in mammals and the chronotropic effect in isolated mammalian atria. H$_4$ receptors are expressed primarily on eosinophils and mast cells and have been shown to be involved in the chemotaxis of both cell types.

In the periphery, H$_3$ receptor sites are found on sympathetic nerves, where they modulate sympathetic neurotransmission and attenuate a variety of end organ responses under control of the sympathetic nervous system. Specifically, H$_3$ receptor activation by histamine attenuates norepinephrine outflow to resistance and capacitance vessels, causing vasodilation. In addition, in rodents, peripheral H$_3$ receptors are expressed in brown adipose tissue, suggesting that they may be involved in thermogenesis regulation.

H$_3$ receptors are also present in the CNS. H$_3$ receptor expression is observed in cerebral cortex, hippocampal formation, hypothalamus and other parts of the human and animal brain. H$_3$ receptors are expressed on histaminergic neurons and, as heteroreceptors, on neurons involved in other neurotransmitter systems, where H$_3$ receptor activation results in presynaptic inhibition of neurotransmitter release. In the particular case of histaminergic neurons, H$_3$ receptors have been implicated in the regulation of histamine hypothalamic tone, which in turn has been associated with the modulation of sleeping, feeding and cognitive processes in the human brain (see, for example, Leurs et al., _Nature Reviews, Drug Discovery,_ 4, (2005), 107).

It is also known and has been described in the literature that histamine is involved in regulation of cognitive and memory processes in the human brain (see, for example, _Life Sciences,_ 72, (2002), 409-414). Consequently, indirect modulation of histaminergic brain function through the central H$_3$ receptors may be a means to modulate these processes. Different classes of H$_3$ receptor ligands have been described and their use for neurological and psychiatric diseases has been suggested (see, e.g., US Patent Publication No. 20040224953, International Publication No. WO2004089373 and International Publication No. WO2004101546). H$_3$ receptor antagonists may be useful for treating various neuropsychiatric conditions, where cognitive deficits are an integral part of the disease, specifically ADHD, schizophrenia and Alzheimer's disease (see, for example, Hancock, A.; Fox, G. in _Drug Therapy_ (ed. Buccafusco, J. J.). (Birkhauser, Basel, 2003).

Imidazole H$_3$ receptor antagonists are well known in the art. More recently, non-imidazole H$_3$ receptor antagonists have been disclosed in U.S. Pat. Nos. 6,720,328 and 6,849,621, and in US Published Applications 2004/0097483, 2004/0048843 and 2004/0019099.

U.S. Pat. No. 5,869,479 discloses compositions for the treatment of the symptoms of allergic rhinitis using a combination of at least one histamine H$_1$ receptor antagonist and at least one histamine H$_3$ receptor antagonist.

SUMMARY OF THE INVENTION

In one aspect, the present invention provides compounds of formula (I):

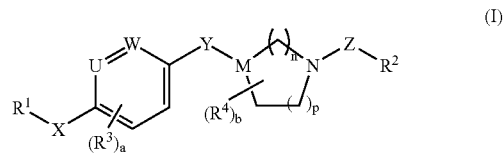

(I)

and pharmaceutically acceptable salts and solvates thereof, wherein:

a is 0, 1, 2, 3 or 4;

b is 0, 1, 2 or 3;

M is CH, n is 1 or 2, and p is 0, 1 or 2; or M is N, n is 2, and p is 1 or 2;

U and W are each CH, or one of U and W is CH and the other is N;

X is a bond, alkylene, —C(O)—, —C(N—OR$^5$)—, —C(N—OR$^5$)—CH(R$^6$)—, —CH(R$^6$)—C(N—OR$^5$)—, —O—, —OCH$_2$—, —CH$_2$O—, —CH(OH)—, —S—, —S(O)— or —S(O)$_2$—;

Y is —O—, —CH$_2$—, —(CH$_2$)$_2$—, —C(=O)—, —C(=NOR$^7$)—, —S—, —S(O)— or —SO$_2$—, provided that when M is N, Y is —CH$_2$—, —(CH$_2$)$_2$—, —C(=O)—, —S—, —S(O)— or —SO$_2$—;

Z is a bond, —CH(R$^9$)—(R$^{10}$—C$_1$-C$_5$ alkylene), —CH(R$^9$)—CH(R$^9$)—O—, —CH(R$^9$)—CH(R$^9$)—N—, —CH(R$^9$)—C(R$^{9a}$)=C(R$^{9a}$)—, —CH(R$^9$)—C(R$^{9a}$)=C(R$^{9a}$)—(R$^{10}$—C$_1$-C$_3$ alkylene) or R$^8$-alkylene interrupted by a cycloalkylene or heterocycloalkylene group, provided that when Z is R$^8$-alkylene interrupted by a heterocycloalkylene group bonded through a ring nitrogen, the alkylene portion of the Z group has 2-4 carbon atoms between the ring to which it is attached and said nitrogen;

R$^1$ is R$^{11}$-alkyl, R$^{11}$-cycloalkyl, R$^{11}$-aryl, R$^{11}$-arylalkyl, R$^{11}$-(6-membered heteroaryl), R$^{11}$-(6-membered heteroaryl)

alkyl, $R^{11}$-(5-membered heteroaryl), $R^{11}$-(5-membered heteroaryl)alkyl, $R^{11}$-heterocycloalkyl,

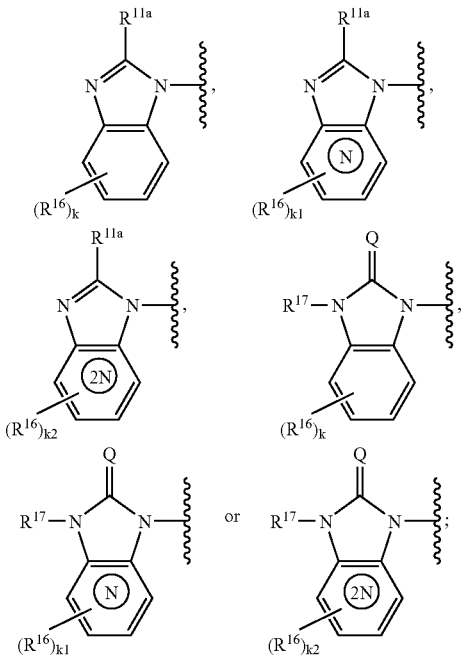

wherein

represents one nitrogen atom in the place of any one of the four unfused ring carbon atoms, and

represents two nitrogen atoms in the place of any two of the four unfused ring carbon atoms, provided that when $R^1$ is attached to X by a nitrogen atom, X is a bond or alkylene;

k is 0, 1, 2, 3 or 4;

k1 is 0, 1, 2 or 3;

k2 is 0, 1 or 2;

Q is O or S;

$R^2$ is $R^{13}$-alkyl, $R^{13}$-alkenyl, $R^{13}$-aryl, $R^{13}$-arylalkyl, $R^{13}$-heteroaryl, $R^{13}$-heteroarylalkyl, $R^{13}$-cycloalkyl or $R^{13}$-heterocycloalkyl;

each $R^3$ is independently selected from the group consisting of H, alkyl, halo, —OH, alkoxy, —CF$_3$, —OCF$_3$, —OCHF$_2$, —NO$_2$, —CO$_2R^{14}$, —N(R$^{14}$)$_2$, —CON(R$^{14}$)$_2$, —NHC(O)R$^{14}$, —NHSO$_2R^{14}$, —SO$_2$N(R$^{14}$)$_2$ and —CN;

each $R^4$ is independently selected from the group consisting of H, halo, alkyl, haloalkyl, —OH, alkoxy, —CF$_3$ and —CN;

$R^5$ is H, alkyl, haloalkyl, $R^{15}$-aryl, $R^{15}$-heteroaryl, $R^{15}$-cycloalkyl, $R^{15}$-heterocycloalkyl, $R^{15}$-arylalkyl, —CF$_3$ or —CH$_2$CF$_3$;

$R^6$ is H or alkyl;

$R^7$ is H, alkyl, haloalkyl, $R^{15}$-aryl or $R^{15}$-heteroaryl;

$R^8$ is 1, 2 or 3 substituents independently selected from the group consisting of H, $R^{15}$-cycloalkyl, $R^{15}$-heterocycloalkyl, $R^{15}$-aryl, $R^{15}$-heteroaryl and haloalkyl, provided that when the $R^8$ substituent is on the carbon joined to the nitrogen atom of the M-containing ring, $R^8$ is joined through a ring carbon atom;

$R^9$ is independently selected from the group consisting of H, alkyl and haloalkyl;

$R^{9a}$ is independently selected from the group consisting of H, fluoro, alkyl and haloalkyl;

$R^{10}$ is 1, 2 or 3 substituents independently selected from the group consisting of H, $R^{15}$-cycloalkyl, $R^{15}$-heterocycloalkyl, $R^{15}$-aryl, $R^{15}$-heteroaryl, halo, haloalkyl, —CN, —OH, alkoxy, —OCF$_3$, —NO$_2$, and —N(R$^6$)$_2$;

$R^{11}$ is 1, 2, 3 or 4 substituents independently selected from the group consisting of H, halo, alkyl, haloalkyl, —OH, alkoxy, alkylthio, $R^{15}$-cycloalkyl, $R^{15}$-heterocycloalkyl, $R^{15}$-aryl, $R^{15}$-arylalkyl, $R^{15}$-heteroaryl, $R^{15}$-heteroarylalkyl, aryloxy, —OCF$_3$, —OCHF$_2$, —NO$_2$, —CO$_2R^{12}$, —N(R$^{12}$)$_2$, —CON(R$^{12}$)$_2$, —NHC(O)R$^{12}$, —NHSO$_2R^{12}$, —SO$_2$N(R$^{12}$)$_2$ and —CN;

$R^{11a}$ is H, alkyl, haloalkyl, alkoxy, alkylthio, $R^{15}$-cycloalkyl, $R^{15}$-heterocycloalkyl, $R^{15}$-aryl, $R^{15}$-arylalkyl, $R^{15}$-cycloalkyl, $R^{15}$-heterocycloalkyl, $R^{15}$-heteroaryl, $R^{15}$-heteroarylalkyl, $R^{15}$-aryloxy, —OCF$_3$, —OCHF$_2$, —N(R$^{12}$)$_2$ or —SCF$_3$;

$R^{12}$ is independently selected from the group consisting of H, alkyl, haloalkyl, $R^{15}$-aryl, $R^{15}$-heteroaryl, $R^{15}$-arylalkyl, $R^{15}$-cycloalkyl and $R^{15}$-heterocycloalkyl;

$R^{13}$ is 1, 2 or 3 substituents independently selected from the group consisting of H, halo, alkyl, haloalkyl, —OH, alkoxy, $R^{15}$-aryl, $R^{15}$-aryloxy, —OCF$_3$, —OCHF$_2$, —NO$_2$, —CO$_2R^{14}$, —N(R$^{14}$)$_2$, —CON(R$^{14}$)$_2$, —NHC(O)R$^{14}$, —NHSO$_2R^{14}$, —SO$_2$N(R$^{14}$)$_2$ and —CN;

$R^{14}$ is independently selected from the group consisting of H, alkyl, haloalkyl, $R^{15}$-aryl, $R^{15}$-heteroaryl, $R^{15}$-cycloalkyl and $R^{15}$-heterocycloalkyl;

$R^{15}$ is 1, 2 or 3 substituents independently selected from the group consisting of H, alkyl, halo, haloalkyl, alkoxy, —N(R$^{18}$)$_2$, -alkylene-N(R$^{18}$)$_2$, —CN, —OCF$_3$ and —OCHF$_2$;

$R^{16}$ is independently selected from the group consisting of alkyl, halogen, haloalkyl, alkenyl, OH, alkoxy, —SO$_{0-2}$-alkyl and —OCF$_3$;

$R^{17}$ is H, alkyl, hydroxy(C$_2$-C$_6$)alkyl-, haloalkyl-, haloalkoxyalkyl-, alkoxyalkyl-, $R^{15}$-aryl, $R^{15}$-arylalkyl-, $R^{15}$-heteroaryl, $R^{15}$-heteroarylalkyl-, $R^{15}$-cycloalkyl or $R^{15}$-cycloalkylalkyl; and $R^{18}$ is independently selected from the group consisting of H and alkyl.

This invention further provides methods for treating: allergy; an allergy-induced airway (e.g., upper airway) response, including but not limited to, pruritis, sneezing, rhinorrhea and mucosal inflammation (see, for example, McLeod, *JPET,* 305 (2003) 1037); congestion, such as nasal congestion; hypotension; a cardiovascular disease; a disease of the gastrointestinal tract; hyper- and hypo-motility and acidic secretion of the gastrointestinal tract, such as GERD; metabolic syndrome; obesity; an obesity-related disorder; a sleeping disorder such as hypersomnia, somnolence, insomnia or narcolepsy; hypo- and hyperactivity of the central nervous system, such as agitation and depression of the CNS; diabetes, including Type I and Type II diabetes mellitus; a CNS disorder, such as migraine, Parkinson's disease, amyotrophic lateral sclerosis (ALS), or a cognition deficit disorder (e.g., attention deficit hyperactivity disorder (ADHD), Alzheimer's Disease (AD) or schizophrenia); (each of the above described diseases/disorders being a "Condition") comprising administering to a patient in need of such treatment an effective amount of at least one compound of formula (I).

The invention also provides pharmaceutical compositions comprising an effective amount of at least one compound of formula (I) and a pharmaceutically acceptable carrier. In one aspect, the compositions further comprise one or more additional agents useful for treating obesity, diabetes, an obesity-related disorder, metabolic syndrome or a cognition deficit disorder. In one aspect, the compositions further comprise one or more $H_1$ receptor antagonists. The compositions are useful for treating a Condition.

The invention further provides methods for treating obesity, an obesity-related disorder, metabolic syndrome or a cognition deficit disorder comprising administering to a patient in need of such treatment an effective amount of a combination of at least one compound of formula (I) and at least one other compound useful for treating obesity, an obesity-related disorder, metabolic syndrome or a cognition deficit disorder.

The invention also provides methods for treating obesity or an obesity-related disorder in a patient, comprising administering to the patient an effective amount of at least one compound of formula (I) and an anti-diabetic agent.

The present invention also provides methods for treating allergy, an allergy-induced airway response or congestion comprising administering to a patient in need of such treatment an effective amount of at least one compound of claim 1 and an effective amount of an $H_1$ receptor antagonist.

The present invention further provides methods for treating diabetes in a patient, comprising administering to the patient an effective amount of at least one compound of claim 1.

The invention also provides kits comprising a single package which contains: (i) a container containing a pharmaceutical composition comprising an effective amount of a compound of formula (I), and (ii) another container containing a pharmaceutical composition comprising an $H_1$ receptor antagonist. Also provided are kits comprising a single package which contains: (i) a container containing a pharmaceutical composition comprising an effective amount of a compound of formula (I), and (ii) another container containing a pharmaceutical composition comprising an effective amount of a separate compound useful for treating obesity, an obesity-related disorder, metabolic syndrome or a cognition deficit disorder.

DETAILED DESCRIPTION OF THE INVENTION

The present invention provides compounds of formula (I), pharmaceutical compositions comprising at least one compound of formula (I), and methods of using at least one compound of formula (I) to treat or prevent a Condition.

Definitions and Abbreviations

As used herein, the following terms have the following meanings, unless indicated otherwise:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"Alkyl" (including, for example, the alkyl portions of arylalkyl and alkoxy) refers to straight and branched carbon chains and contains from one to six carbon atoms.

"Alkylene" refers to a divalent straight or branched alkyl chain, e.g., methylene ($—CH_2—$) or propylene ($—CH_2CH_2CH_2—$).

"Haloalkyl" or "haloalkoxy" refer to alkyl or alkoxy chains as defined above wherein one or more hydrogen atoms are replaced by halogen atoms, e.g., $—CF_3$, $CF_3CH_2CH_2—$, $CF_3CF_2—$ or $CF_3O—$.

"Aryl" (including the aryl portion of arylalkyl) refers a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment.

"Arylalkyl" refers to an aryl group, as defined above, bound to an alkyl group, as defined above, wherein said alkyl group is the point of attachment.

"Cycloalkyl" refers to a non-aromatic mono- or multicyclic ring system comprising about 3 to about 10 carbon atoms. In one embodiment, a cycloalkyl contains from about 5 to about 10 carbon atoms. In one embodiment, cycloalkyl rings contain about 3 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantly and the like.

"Halogen" or "halo" refers to $—F$, $—Cl$, $—Br$, or $—I$.

"Heteroaryl" refers to cyclic groups, having 1 to 4 heteroatoms selected from O, S or N, said heteroatom interrupting a carbocyclic ring structure and having a sufficient number of delocalized pi electrons to provide aromatic character. In one embodiment, the aromatic heterocyclic groups contain from 2 to 14 carbon atoms. The rings do not contain adjacent oxygen and/or sulfur atoms. Examples include but are not limited to 5-membered rings such as isothiazolyl, isoxazolyl, oxazolyl, furazanyl, triazolyl, tetrazolyl, thiazolyl, thienyl, furanyl (furyl), pyrrolyl and pyrazolyl, and 6-membered rings such as pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide) and triazinyl, and bicyclic groups such as pteridinyl, indolyl (benzopyrrolyl), pyridopyrazinyl, isoquinolinyl, quinolinyl, naphthyridinyl. All available substitutable carbon and nitrogen atoms can be substituted as defined.

"Heterocycloalkyl" refers to a saturated carbocylic ring containing from 3 to 15 carbon atoms. In one embodiment, from 4 to 6 carbon atoms, which carbocyclic ring is interrupted by 1 to 3 hetero atoms selected from $—O—$, $—S—$, $—SO—$, $—SO_2$ or $—NR^{40}—$ wherein $R^{40}$ represents H, $C_1$ to $C_6$ alkyl, arylalkyl, $—C(O)R^{30}$, $—C(O)OR^{30}$, or $—C(O)N(R^{30})_2$ (wherein each $R^{30}$ is independently selected from the group consisting of H, alkyl, phenyl and benzyl). The rings do not contain adjacent oxygen and/or sulfur atoms. Examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

"Cycloalkylene" refers to a divalent cycloalkyl ring, e.g.

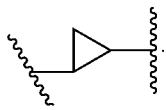

"Heterocycloalkylene" refers to a divalent heterocycloalkyl ring, e.g.

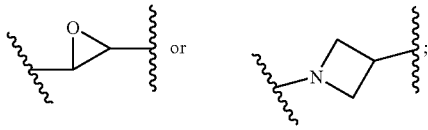

therefore, when $R^8$-alkylene is said to be interrupted by cycloalkylene or heterocycloalkylene, groups such as

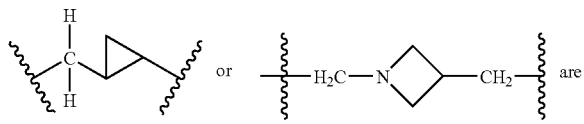

contemplated.

for example in the structure

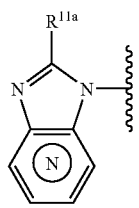

represents a nitrogen atom that is located at one of the 4 non-fused positions of the ring, i.e., positions 4, 5, 6 or 7 indicated below:

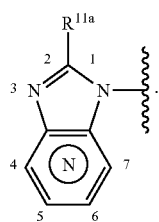

Similarly,

means that two nitrogens are located at any two of the 4 non-fused positions of the ring, e.g., the 4 and 6 positions, the 4 and 7 positions, or the 5 and 6 positions.

Also, as used herein, "upper airway" usually means the upper respiratory system, i.e., the nose, throat, and associated structures.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

A line drawn into a ring means that the indicated bond may be attached to any of the substitutable ring carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. The term "stable compound" or "stable structure" is meant to describe a compound that is sufficiently robust to survive isolation to a useful degree of purity from a reaction mixture, and formulation into an efficacious therapeutic agent.

When M is CH and an $R^4$ substituent is present on the ring (i.e., b is 1, 2 or 3), the $R^4$ substituent can replace the H on said carbon, e.g., the ring can be:

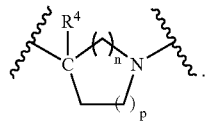

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)-ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of formula (I) incorporates an amine functional group, a prodrug can be formed by the replacement of a hydrogen atom in the amine group with a group such as, for example, R"-carbonyl, R"O-carbonyl, NR"R'"-carbonyl where R" and R'" are each independently $(C_1-C_{10})$alkyl, $(C_3-C_7)$ cycloalkyl, benzyl, or R"-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of formula (I) can form salts which are also within the scope of this invention. Reference to a compound of formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, a salt is a pharmaceutically acceptable (i.e., non-toxic, physiologically acceptable) salt, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of formula (I), and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of formula (I), and of the salts, solvates, esters and prodrugs of the compounds of formula (I), are intended to be included in the present invention.

The phrase "at least one compound of formula (I)" means that one to three different compounds of formula (I) may be used in a pharmaceutical composition or method of treatment. In one embodiment one compound of formula (I) is used. Similarly, "at least one $H_1$ receptor antagonist" or "at least one other compound (or agent) for treating obesity, an obesity-related disorder, metabolic syndrome or a cognition deficit disorder" means that one to three different $H_1$ antagonists or other compounds may be used in a pharmaceutical composition or method of treatment. In one embodiment, one $H_1$ antagonist or one other compound for treating obesity, an obesity-related disorder, metabolic syndrome or a cognition deficit disorder is used in the combinations.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to any disorder which results from a patient having a BMI of 25 or greater. Non-limiting examples of an obesity-related disorder include edema, shortness of breath, sleep apnea, skin disorders and high blood pressure.

The term "metabolic syndrome" refers to a combination of risk factors for cardiovascular disease (CVD) identified in the National Cholesterol Education Program's Adult Treatment Panel III report. See for example the discussion by Grundy et al in *Circulation*, 109 (2004), 433-438. The components of metabolic syndrome are: 1) abdominal obesity; 2) atherogenic dyslipidemia; 3) raised blood pressure; 4) insulin resistance; 5) proinflammatory state; and 6) prothrombotic state.

Unless otherwise stated, the following abbreviations, as used herein, have the following meanings:

Me=methyl; Et=ethyl; Bn=benzyl; Bu=butyl; Pr=propyl; Ph=phenyl; t-BOC=tert-butoxycarbonyl; Ac=acetyl; BINAP=2,2'-bis(diphenylphosphino)-1,1'binaphthyl; DCE=1,2-dichloroethane; DCM=dichloro-methane; DEAD=diethyl azodicarboxylate; DIPEA=N,N-diisopropylethylamine (Hunig's base); DMF=dimethylformamide; EDC=1-(3-dimethylaminopropyl)-3-ethylcarbodiimide; HOBT=1-hydroxybenzotriazole; NaBH(Oac)$_3$=sodium triacetoxyboro-hydride; PyBOP=benzotriazol-1-yloxytri-pyrrolidinophosphonium hexafluorophosphate; RT=room temperature; TFA=trifluoroacetic acid; THF=tetrahydrofuran; TEMPO=2,2,6,6-tetramethyl-1-piperidinyloxy, free radical; TLC=thin layer chromatography; MS=Mass Spectrometry; nM=nanomolar; Ki=Dissociation Constant for substrate/receptor complex.

The Compounds of Formula (I)

The invention provides compounds having the formula:

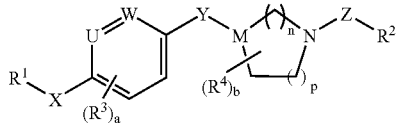
(I)

and pharmaceutically acceptable salts and solvates thereof, wherein $R^1$, $R^2$, $R^3$, $R^4$, M, U, W, X, Y, Z, a, b, n and p are defined above for the compounds of formula (I).

In one embodiment, $R^1$ is $R^{11}$-aryl, $R^{11}$-(6-membered heteroaryl),

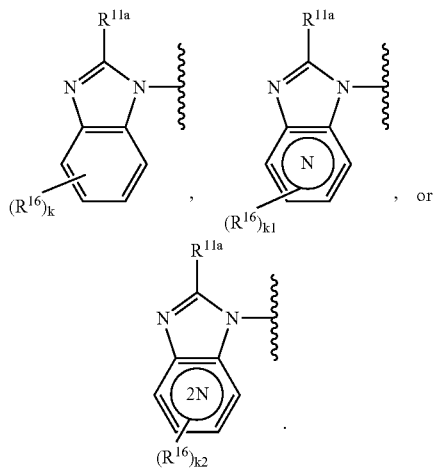

In one embodiment, $R^1$ is $R^{11}$-aryl, aryl is phenyl and $R^{11}$ is 1 to 4 substituents independently selected from the group consisting of H, halo, alkyl, haloalkyl or —CN. In another embodiment, $R^{11}$ is one or two substituents independently selected from H and halo, or $R^{11}$ is one substituent selected from the group consisting of —CF$_3$, —CHF$_2$ and —CN.

In another embodiment, $R^1$ is $R^{11}$-(6-membered heteroaryl), the 6-membered heteroaryl is pyridyl and $R^{11}$ is 1-3 substituents independently selected from the group consisting of H, halo, alkyl, haloalkyl and —CN. In another embodiment, $R^1$ is $R^{11}$-(6-membered heteroaryl), the 6-membered heteroaryl is pyridyl is one or two substituents independently selected from the group consisting of H and halo, or $R^{11}$ is one substituent selected from the group consisting of —CF$_3$, —CHF$_2$ and —CN.

In one embodiment, $R^1$ is

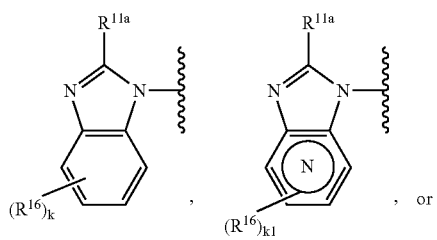

-continued

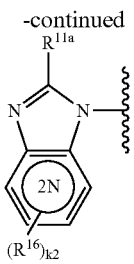

$R^{11a}$ is $C_1$-$C_3$ alkyl, halo($C_1$-$C_3$)alkyl, $C_1$-$C_3$ alkoxy, $C_1$-$C_3$ alkylthio, $R^{15}$-phenyl or $R^{15}$-heteroaryl; $R^{15}$ is 1-3 substituents independently selected from the group consisting of H, halo, alkyl, haloalkyl, —OCF$_3$, —CHF$_2$ or —CN; $R^{16}$ is as defined above; and k, k1 and k2 are each 0, 1 or 2.

In another embodiment, $R^1$ is

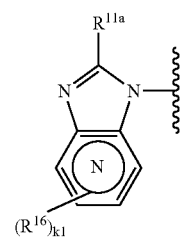

wherein $R^{11a}$ is ($C_1$-$C_3$)alkyl, $C_1$-$C_3$ alkoxy, $C_1$-$C_3$ alkylthio, $R^{15}$-phenyl or $R^{15}$-pyridyl; $R^{15}$ is 1 or 2 substituents independently selected from the group consisting of H, halo, alkyl and haloalkyl; $R^{16}$ is as defined above; and k1 is 0 or 1.

In another embodiment, $R^1$ is

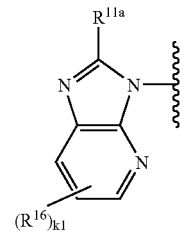

wherein $R^{11a}$ is —C$_2$F$_5$, —CF$_3$, C$_2$H$_5$—O—, CH$_3$—O—, C$_2$H$_5$—S—, CH$_3$—S—, $R^{15}$-phenyl or $R^{15}$-pyridyl; $R^{15}$ is 1 or 2 substituents independently selected from the group consisting of H, F, Cl, —CH$_3$, and —CF$_3$; k1 is 0 or 1; and $R^{16}$ is F, Cl or —CF$_3$.

In one embodiment, M is CH.

In another embodiment, M is N.

In still another embodiment, $R^3$ and $R^4$ are independently selected from the group consisting of H, alkyl, fluoro and —OH.

In a further embodiment, M is CR$^4$, wherein $R^4$ is H or fluoro.

In one embodiment, n is 2 and p is 1.

In another embodiment, a and b are each independently 0 or 1.

In another embodiment, a and b are each 0.

In still another embodiment, both U and W are CH.

In a further embodiment, X is y a single bond or —C(N—OR$^5$)—, wherein R$^5$ is H or alkyl.

In one embodiment, X is a single bond.

In another embodiment, Y is —O— or —C(=O)—,

In another embodiment, Y is —O—.

In still another embodiment, Z is C$_1$-C$_3$ alkylene, —CH(R$^9$)—(R$^{10}$—C$_1$-C$_5$ alkylene)-, —CH(R$^9$)—C(R$^{9a}$)=C(R$^{9a}$)—, —(CH$_2$)$_2$—O— or C$_1$-C$_3$ alkylene interrupted by a cycloalkylene group, wherein R$^9$ and R$^{9a}$ are each H and R$^{10}$ is halo.

In another embodiment, Z is —CH$_2$—, —(CH$_2$)$_3$—, —CH$_2$—CH=CH—, —(CH$_2$)$_2$—CH(F)—, —CH$_2$—CH(F)—CH$_2$—, —(CH$_2$)$_2$—O— or

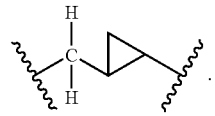

In one embodiment, Z is —CH$_2$—.

In one embodiment, R$^2$ is R$^{13}$-heteroaryl or R$^{13}$-heterocycloalkyl.

In another embodiment, R$^2$ is a R$^{13}$-(5 or 6 membered heteroaryl) or a R$^{13}$-(4, 5 or 6-membered heterocycloalkyl).

In still another embodiment, R$^2$ is R$^{13}$-pyridyl, R$^{13}$-pyrimidyl, R$^{13}$-pyradazinyl, R$^{13}$-tetrahydropyranyl, R$^{13}$-azetidinyl, R$^{13}$-oxazolyl or R$^{13}$-thiazolyl.

In a further embodiment, when R$^2$ is R$^{13}$-pyridyl, R$^{13}$-pyrimidyl, R$^{13}$-pyradazinyl, R$^{13}$-oxazolyl or R$^{13}$-thiazolyl, R$^{13}$ is 1 or 2 substituents independently selected from the group consisting of H, —CH$_3$, —NH$_2$ and —NHCH$_3$.

In one embodiment, when R$^2$ is R$^{13}$-tetrahydropyranyl or R$^{13}$-azetidinyl, R$^{13}$ is 1 or 2 substituents independently selected from the group consisting of H and —CH$_3$.

In another embodiment, R$^2$ is 2-amino pyridyl, 2-amino oxazolyl, 2-amino thiazolyl, 1-methyl-azetidinyl or tetrahydropyranyl.

In one embodiment, R$^2$ is 2-amino pyridyl.

In one embodiment, the compounds of formula (I) have the formula (IA):

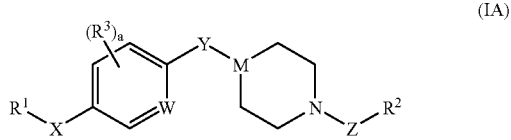

and pharmaceutically acceptable salts or solvates thereof, wherein

M is CH or N;

W is CH or N;

X is a single bond, —CH$_2$—, —C(O)—, —C(=NOR)—, —CH(OH)—;

Y is —O—, —S—, —SO$_2$—, —C(O)— or —CH$_2$—, such that when M is N, Y is —S—, —SO$_2$—, —C(O)— or —CH$_2$—;

Z is a single bond;

R$^1$ is -aryl, -heteroaryl, -heterocycloalkyl,

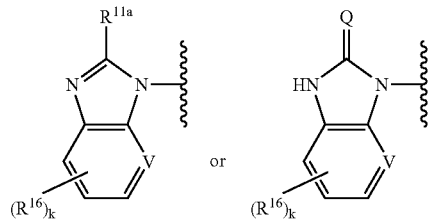

wherein an aryl group can be substituted with up to 2 groups chosen from alkyl, halo or —CN; a heterocycloalkyl can be substituted with up to groups chosen from alkyl and heteroaryl; and a heteroaryl group can be substituted with up to 2 groups chosen from -halo, alkyl and alkoxy;

R$^2$ is -heterocycloalkyl, heteroaryl, —CH(G)-aryl, —CH(G)-heteroaryl,

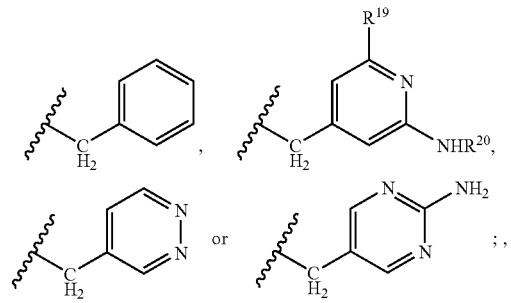

each occurrence of R$^3$ is independently -halo;

R$^{11a}$ is —H, —S-alkyl, heteroaryl, aryl, —CF$_2$(CF$_3$) or —CF$_3$;

R$^{16}$ is —H, -halo, C$_1$-C$_6$ alkyl; or alkenyl;

R$^{19}$ is —H or alkyl;

R$^{20}$ is —H or -alkyl;

G is —H or -alkyl;

Q is O or S;

V is CH or N;

a is 0, 1 or 2; and k is 0 or 1.

In one embodiment, M is CH.

In another embodiment, M is N.

In one embodiment, W is CH.

In another embodiment, W is N.

In one embodiment, X is a bond.

In another embodiment, X is —CH$_2$—.

In another embodiment, X is —C(O)—.

In still another embodiment, X is —C(=NOR)—.

In a further embodiment, X is —CH(OH)—.

In one embodiment, Y is —O—.

In another embodiment, Y is —CH$_2$—.

In another embodiment, Y is —C(O)—.

In still another embodiment, Y is —S—.

In a further embodiment, Y is —SO$_2$—.

In one embodiment, M is CH and Y is —O—.

In another embodiment, M is CH and Y is —CH$_2$—.

In still another embodiment, M is CH and Y is —C(O)—.

In another embodiment, M is CH and Y is —S—.

In still another embodiment, M is CH and Y is —SO$_2$—.

In one embodiment, M is N and Y is —O—.

In another embodiment, M is N and Y is —CH$_2$—.

In still another embodiment, M is N and Y is —C(O)—.

In one embodiment, $R^1$ is aryl.
In another embodiment, $R^1$ is heteroaryl.
In another embodiment, $R^1$ is heterocycloalkyl.
In still another embodiment, $R^1$ is:

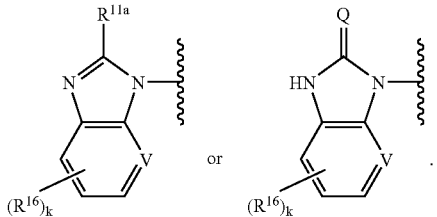

In one embodiment, $R^1$ is phenyl.
In another embodiment, $R^1$ is pyridyl.
In another embodiment, $R^1$ is pyrimidinyl.
In still another embodiment, $R^1$ is thiophenyl.
In a further embodiment, $R^1$ is N-piperazinyl.
In one embodiment, $R^1$ is N-piperidinyl.
In another embodiment, $R^1$ is N-pyrrolidinyl.
In yet another embodiment, $R^1$ is N-morpholinyl.
In another embodiment, $R^1$ is N-azetidinyl.
In a further embodiment, $R^1$ is N-[1,4]-diazapanyl.
In one embodiment, $R^1$ is:

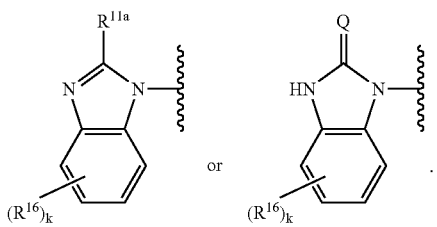

In another embodiment, $R^1$ is:

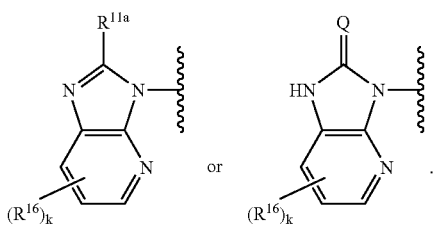

In another embodiment, $R^1$ is:

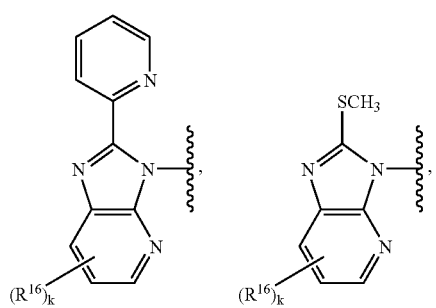

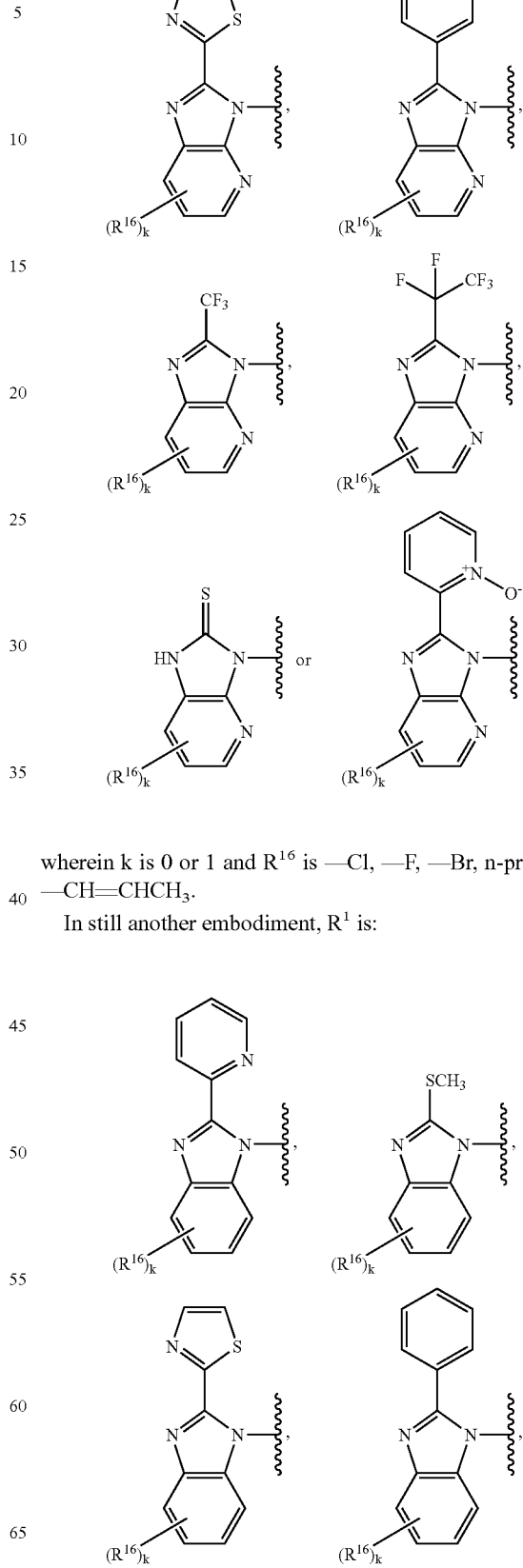

wherein k is 0 or 1 and $R^{16}$ is —Cl, —F, —Br, n-propyl or —CH=CHCH$_3$.

In still another embodiment, $R^1$ is:

-continued

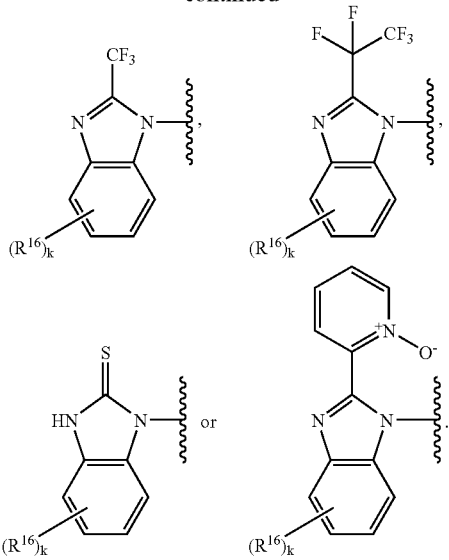

wherein k is 0 or 1 and $R^{16}$, when present, is —Cl, —F, —Br, n-propyl or —CH=CHCH$_3$.

In one embodiment, $R^2$ is -heteroaryl.
In another embodiment, $R^2$ is -heterocycloalkyl.
In another embodiment, $R^2$ is —CH$_2$-heteroaryl.
In still another embodiment, $R^2$ is —CH$_2$-heterocycloalkyl.
In another embodiment, $R^2$ is —CH(G)-aryl.
In still another embodiment, $R^2$ is —CH(G)-heteroaryl.
In yet another embodiment, $R^2$ is:

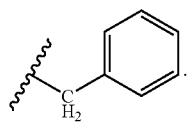

In one embodiment, $R^2$ is:

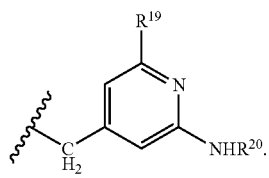

In another embodiment, $R^2$ is:

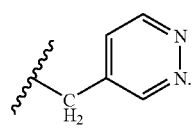

In another embodiment, $R^2$ is:

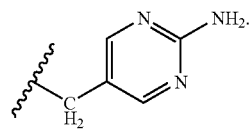

In a further embodiment, $R^2$ is tetrahydropyranyl.
In another embodiment, $R^2$ is thiazolyl.
In one embodiment, $R^2$ is —CH$_2$-aryl.
In another embodiment, $R^2$ is —CH(CH$_3$)-aryl.
In another embodiment, $R^2$ is —CH$_2$-heteroaryl.
In still another embodiment, $R^2$ is —CH(CH$_3$)-heteroaryl.
In one embodiment, $R^2$ is —CH$_2$-phenyl.
In one embodiment, $R^2$ is:

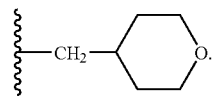

In another embodiment, $R^2$ is —CH(CH$_3$)-pyridyl.
In still another embodiment, $R^2$ is:

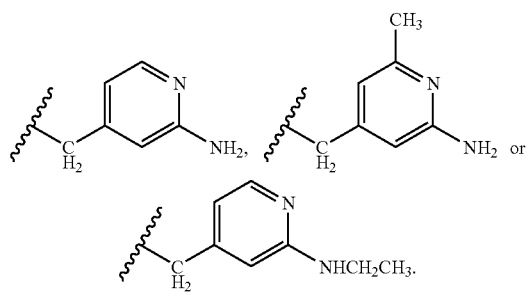

In one embodiment, a is 1 and $R^3$ is —F.
In another embodiment, a is 2 and each occurrence of $R^3$ is —F.
In one embodiment, M is N, Z is a bond and $R^2$ is:

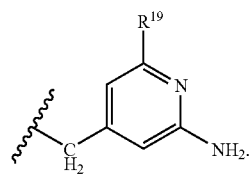

In another embodiment, $R^1$ is:

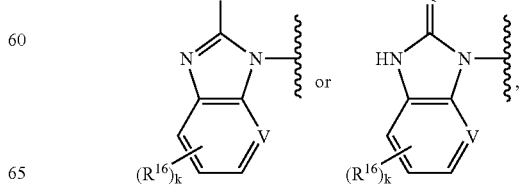

and R² is:

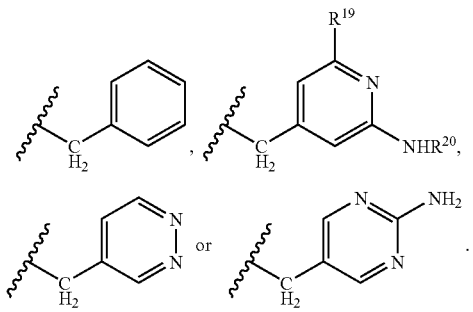

In another embodiment, M is CH, R¹ is

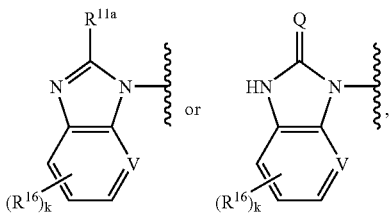

R² is:

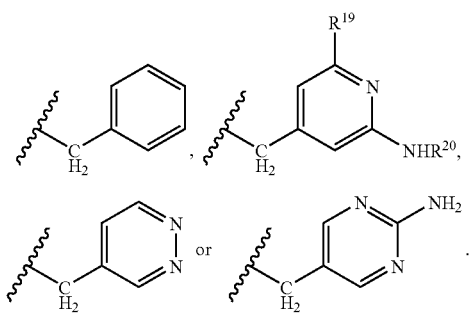

Illustrative compounds of formula (I) include, but are not limited to, the compounds of formulas 1A-16A, 16B, 17A-81A, 81B and 82A-116A as depicted below in the Examples section.

Methods for Making the Compounds of Formula (I)

The compounds of formula (I) can be prepared via procedures known to those skilled in the art. Compounds of this invention are most typically prepared through the initial assembly of the central part of the molecule (BC fragment— see Scheme 1), followed by the attachment of the corresponding A and D fragments. In Scheme 1, R', R'' and R''' are as defined in the Scheme; Pr is a protecting group such as BOC; X' is, for example a halogen, aldehyde, amino or nitro group; and the remaining variables are as defined above for formula (I).

Scheme 1

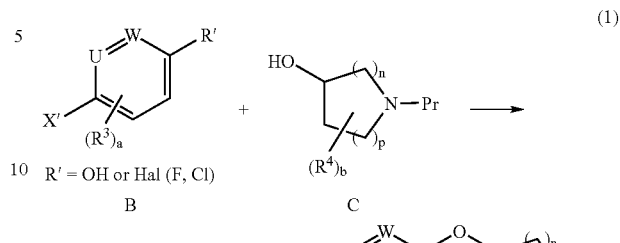

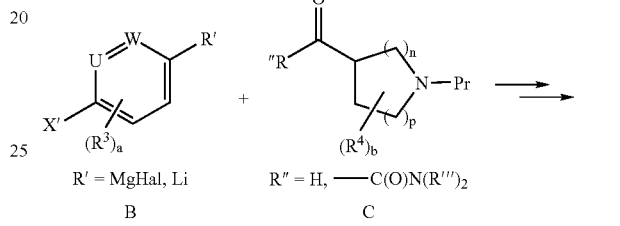

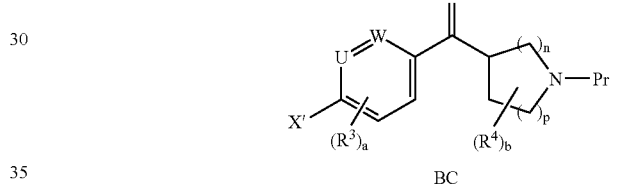

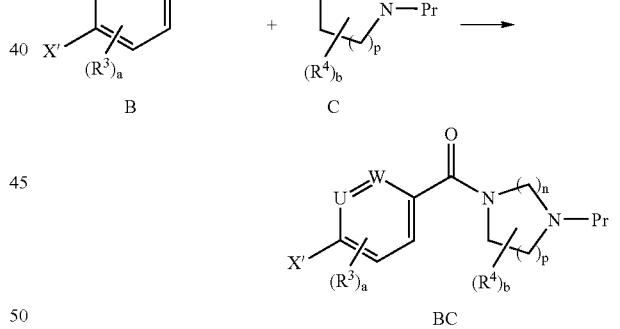

The connection between the B and C rings in cases (1), where Y is —O— and M is CH, is achieved through a Mitsunobu reaction of the B-ring-based phenol, or alternatively, through an aromatic nucleophilic substitution on a halogen-substituted B ring by the C-ring alcohol. In cases (2), where Y is C=O and M is CH, connection between the B and C rings is established through addition of an organometallic nucleophile (a Grignard or an organolithium reagent), derived from one of the fragments, to a carbonyl-based electrophile derived from the other fragment, followed by the adjustment of the oxidation state of the linker, if necessary. In cases (3), where Y is C=O and M is N, connection between the B and C rings is most easily established through amide coupling of the corresponding B-ring benzoic acid and C-ring piperazine or diazepine.

The installation or formation of the A ring is most conveniently accomplished by taking advantage of a preinstalled functionality on the B-ring (X'—see Scheme 1), including, but not limited to an aldehyde, an amino group, a nitro group or a halogen. For example, halogen and aldehyde substituted compounds are used to provide compounds wherein $R^1$ is aryl or heteroaryl, and nitro and amino substituted compounds are used to prepare compounds wherein $R^1$ is benzimidazolyl. Some general approaches are shown in Scheme 2. In Scheme 2, Ar is a $NO_2$-substituted aryl group or a synthetic precursor therefore, which can be later elaborated into a benzimidazole as described in specific procedures, below. $R^{1'}$ is chosen so as to provide $R^1$ upon the transformation shown in the scheme. Pr is a protecting group, Hal and Met are as defined in the scheme, and the remaining variables are as defined for formula (I).

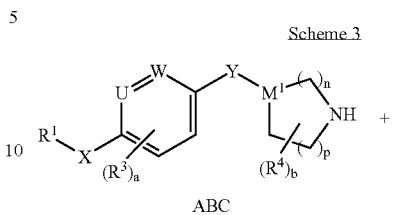

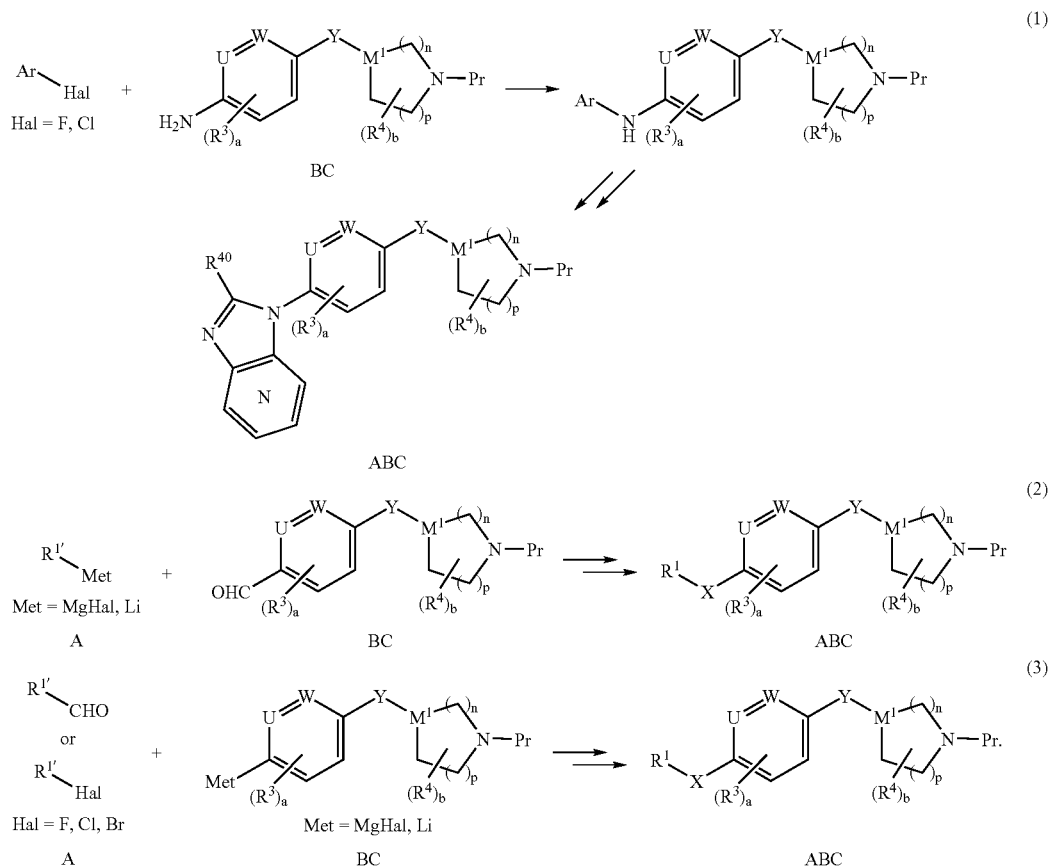

While the preinstalled functional groups play the key role in establishing the connectivity between the A and B rings, final elaboration of the A ring may require several additional steps known to those skilled in the art.

Examples of D fragments, as well as practical methods employed in the addition of D fragments onto the ABC portion of the molecule have been previously described for different structural series (e.g., U.S. Pat. No. 6,720,378 and US 2004/0097483). In Scheme 3, Z' is as described below and the remaining variables are as defined for formula (I).

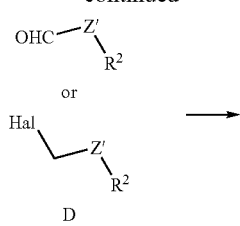

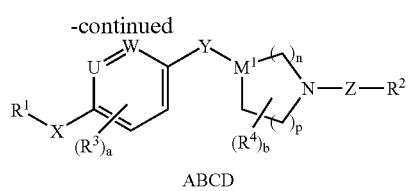

ABCD

In the most simple case the D-electrophile is a one-carbon aldehyde or alkyl halide attached to the $R^2$ group (Z' is a bond in D—Scheme 3), but can also be an epoxide or other longer-chain electrophile in cases where Z' is an optionally substituted $C_1$ to $C_5$ alkyl or alkenyl group. The compounds are synthesized through chain extension of one-carbon starting D-aldehydes (previously described or commercially available) by various methods known to those skilled in the art. Those methods include, but are not limited to, the reactions of starting aldehydes with alkylmetal reagents, carbon-phosphorus reagents (known to those skilled in the art as Wittig reactions and Horner-Emmons reactions), and also include reactions with other carbon nucleophiles, followed by appropriate functional elaboration, leading to compounds of the type D, where Z' is an appropriately substituted $C_1$ to $C_5$ alkyl or alkenyl group. Alternatively, in the particular case when $R^2$ is an aryl or heteroaryl, the corresponding D fragment with the elongated Z' is prepared by coupling an aryl halide with an appropriate alkyl or alkenyl metal reagent (e.g., Li or MgX, wherein X is a halogen), optionally in the presence of an appropriate transition metal catalyst (e.g, Cu, Ni).

Alternatively, compounds described in this invention are prepared in a right-to-left stepwise fashion: C+D, followed by B+CD, followed by A+BCD, using the same synthetic approaches as described above, but in a different sequence. Also, when the process of bond formation between any of the two fragments is generally compatible with the rest of the molecule, the compounds are synthesized through a left-to-right stepwise approach: A+B, followed by AB+C, followed by ABC+D.

Uses of the Compounds of Formula (I)

The compounds of formula (I) are useful for treating or preventing a Condition. Accordingly, the present invention provides methods for treating or preventing a Condition in a patient, comprising administering to the patient an effective amount of at least one compound of formula (I) or a pharmaceutically acceptable salt or solvate thereof.

In one embodiment, the compounds of formula (I) are useful for treating congestion, metabolic syndrome, obesity, an obesity-related disorder or a cognition deficit disorder.

In another embodiment, the compounds of formula (I) are useful for treating obesity or an obesity-related disorder.

In another embodiment, the compounds of formula (I) are useful for treating diabetes. There are two major forms of diabetes: Type I diabetes (also referred to as insulin-dependent diabetes or NIDDM) and Type II diabetes (also referred to as noninsulin dependent diabetes or NIDDM). In one embodiment, the compounds of formula (I) are useful for treating Type I diabetes. In another embodiment, the compounds of formula (I) are useful for treating Type II diabetes.

Combination Therapy

The present methods for treating or preventing a Condition can further comprise administering one or more additional therapeutic agents in addition to the at least one compound of formula (I). Additional therapeutic agents useful in the present methods include, but are not limited to, $H_1$ receptor antagonists, weight-loss agents, HMG-CoA reductase inhibitors, sterol absorption inhibitors, anti-diabetic agents, any agent useful for treating obesity, an obesity-related disorder, any agent useful for treating metabolic syndrome, any agent useful for treating a cognition deficit disorder, or any combination of two or more of these additional therapeutic agents.

In one embodiment, the compounds of formula (I) can be combined with an $H_1$ receptor antagonist (i.e., the compounds of formula (I) can be combined with an $H_1$ receptor antagonist in a pharmaceutical composition, or the compounds of formula (I) can be administered with an $H_1$ receptor antagonist).

Numerous chemical substances are known to have histamine $H_1$ receptor antagonist activity and can therefore be used in the methods of this invention. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

In one embodiment, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole. In another embodiment, said $H_1$ antagonist is selected from loratadine, descarboethoxyloratadine, fexofenadine or cetirizine.

In one embodiment, in the above combinations of $H_3$ and $H_1$ antagonists, nasal congestion is treated.

Weight-loss agents include appetite suppressants, metabolic rate enhancers and nutrient absorption inhibitors. Appetite suppressant agents useful for treating obesity or metabolic syndrome include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagons-like peptide 1 (GLP-1) agonists; topiramate; and phytopharm compound 57. Metabolic rate enhancers include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxyl steroid dehydrogenase type 1 (11β HSD-1) inhibitors; melanocortin-3 receptor (Mc3r) agonists; and stearoyl-CoA desaturase-1 (SCD-1) compounds. Nutrient absorption inhibitors include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Specific compounds for use in the combination for treating obesity and metabolic syndrome include rimonabant, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

In one embodiment, compounds for use in the combination for treating obesity and metabolic syndrome include rimonabant, dexfenfluramine, fenfluramine, phentermine, leptin, nalmefene, axokine, sibutramine, topiramate, phytopharm compound 57, oleoyl-estrone and orlistat.

In another embodiment, the invention provides combinations of at least one compound of formula (I) and one or more HMG-CoA reductase inhibitors and/or one or more substituted azetidinone or substituted β-lactam sterol absorption inhibitors for treating metabolic syndrome or obesity.

Typical HMG-CoA reductase inhibitors include statins such as lovastatin, simvastatin, pravastatin, atorvastatin, fluvastatin, resuvastatin, cerivastatin, rivastatin and pitavastatin. In one embodiment, the HMG-CoA reductase inhibitor is simvastatin.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Non-limiting examples of suitable substituted azetidinones and methods of making the same include those disclosed in U.S. Pat. No. RE 37,721, U.S. Pat. Nos. 5,306,817, 5,561,227, 5,618,707, 5,624,920, 5,631,365, 5,656,624, 5,627,176, 5,633,246, 5,661,145, 5,688,785, 5,688,787, 5,688,990, 5,698,548, 5,728,827, 5,739,321, 5,744,467, 5,756,470, 5,767,115, 5,846,966, 5,856,473, 5,886,171, 5,919,672, 6,093,812, 6,096,883, 6,133,001, 6,207,822, 6,627,757, 6,632,933, U.S. Patent Publication Nos. 2003/0105028, 2004/0180860, 2004/0180861, and 2004/0198700, N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, and diphenyl azetidinones and derivatives disclosed in U.S. Patent Publication Nos. 2002/0039774, 2002/0128252, 2002/0128253 and 2002/0137689, and PCT Published Application Nos. WO 2002/066464, WO 04/000805, WO 04/005247, WO 04/000804, WO 04/000803, WO 04/014947, WO 04/087655, WO 05/009955, WO 05/023305, WO 05/021495, WO 05/021497, WO 05/044256, WO 05/042692, WO 05/033100, WO 05/030225, WO 05/047248, WO 05/046662, WO 05/061451, WO 05/061452, WO 05/062824, WO 05/02897, WO 05/000353, each of which is incorporated by reference herein.

An example of a suitable substituted azetidinone compound is represented by Formula (A) (ezetimibe) below:

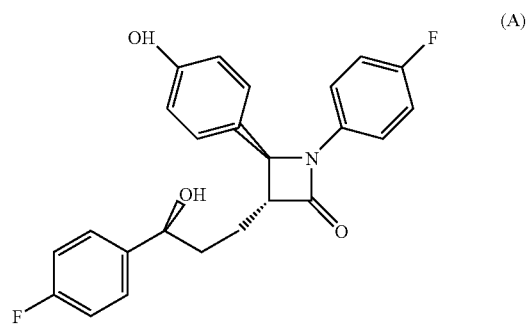

or pharmaceutically acceptable salts or solvates of the compound of Formula (A). The compound of Formula (A) can be in anhydrous or hydrated form. A product containing ezetimibe compound is commercially available as ZETIA® ezetimibe formulation from MSP Pharmaceuticals.

Typical compounds for use in combination with an $H_3$ antagonist of this invention for the treatment of a cognition deficit disorder are atomoxetine and dexmethylphenidate for the treatment of ADHD, olanzapine, risperidone or aripiprazole for treatment of schizophrenia, and donepezil, heptylphysostigmine, tacrine, rivastigmine or galantamine for the treatment of Alzheimer's Disease.

In one embodiment, the compounds of formula (I) can be co-administered with an anti-diabetic agent for treating diabetes.

Examples of anti-diabetic agents useful in the present methods for treating diabetes include sulfonylureas, insulin sensitizers (such as PPAR agonists, DPPIV inhibitors, PTP-1B inhibitors and glucokinase activators), α-glucosidase inhibitors, insulin secretagogues, hepatic glucose output lowering compounds, anti-obesity agents, antihypertensive agents, meglitinides, insulin and insulin-containing compositions.

In one embodiment, the anti-diabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide. Insulin sensitizers include PPAR-γ agonists described in detail above. In one embodiment, useful PPAR-γ agonists are troglitazone, rosiglitazone, pioglitazone and englitazone; biguanidines such as metformin and phenformin; DPPIV inhibitors such as sitagliptin, saxagliptin, denagliptin and vildagliptin; PTP-1B inhibitors; and glucokinase activators. α-Glucosidase inhibitors that can be useful in treating type II diabetes include miglitol, acarbose, and voglibose. Hepatic glucose output lowering drugs include Glucophage and Glucophage XR. Insulin secretagogues include sulfonylurea and non-sulfonylurea drugs such as GLP-1, exendin, GIP, secretin, glipizide, chlorpropamide, nateglinide, meglitinide, glibenclamide, repaglinide and glimepiride. Insulin includes all formulations of insulin, including long acting and short acting forms of insulin.

Non-limiting examples of anti-obesity agents useful in the present methods for treating diabetes include CB1 antagonists or inverse agonists such as rimonabant, neuropeptide Y antagonists, MCR4 agonists, MCH receptor antagonists, histamine H3 receptor antagonists or inverse agonists, leptin, appetite suppressants such as sibutramine, and lipase inhibitors such as xenical.

Non-limiting examples of antihypertensive agents useful in the present methods for treating diabetes include β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Non-limiting examples of meglitinides useful in the present methods for treating diabetes include repaglinide and nateglinide.

Non-limiting examples of insulin sensitizers include biguanides, such as metformin and thiazolidinediones.

In one embodiment, the insulin sensitizer is a thiazolidinedione.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the compounds of formula (I) can be co-administered with an anti-diabetic agent for treating obesity or an obesity-related disorder.

Anti-diabetic agents useful in the present methods for treating obesity or an obesity-related disorder include, but are not limited to the anti-diabetic agents listed above herein.

In the combination therapies of the present invention, the at least one compound of formula (I) and the one or more additional therapeutic agents can be administered simultaneously (at the same time, in a single dosage form or in separate dosage forms) or sequentially (first one and then another, etc. . . . over a period of time) in any order.

Pharmaceutical Compositions and Administration

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound of formula (I) is administered orally.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg. In one embodiment, the quantity per unit dose is from about 1 mg to about 75 mg. In one embodiment, the quantity per unit dose is from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day. In one embodiment the daily dosage is from about 1 mg/day to about 75 mg/day, in two to four divided doses.

When the invention comprises a combination of $H_3$ antagonist and $H_1$ antagonist compounds, the two active components may be co-administered simultaneously or sequentially, or a single pharmaceutical composition comprising a $H_3$ antagonist and an $H_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_1$ antagonist can be determined from published material, and may range from about 1 to about 1000 mg per dose. In one embodiment, when used in combination, the dosage levels of the individual components are lower than the recommended individual dosages because of the advantageous effect of the combination.

When separate $H_3$ and $H_1$ antagonist pharmaceutical compositions are to be administered, they can be provided in a kit comprising in a single package, one container comprising an $H_3$ antagonist in a pharmaceutically acceptable carrier, and a separate container comprising an $H_1$ antagonist in a pharmaceutically acceptable carrier, with the $H_3$ and $H_1$ antagonists being present in amounts such that the combination is therapeutically effective. A kit is advantageous for administering a combination when, for example, the components must be administered at different time intervals or when they are in different dosage forms.

Similarly, when the invention comprises a combination of $H_3$ antagonist and another compound for treating obesity, an obesity-related disorder, metabolic syndrome or a cognition deficit disorder, the two active components may be co-administered simultaneously or sequentially, or a single pharmaceutical composition comprising a $H_3$ antagonist and another compound in a pharmaceutically acceptable carrier can be administered. The components of the combination can be administered individually or together in any conventional dosage form such as capsule, tablet, powder, cachet, suspension, solution, suppository, nasal spray, etc. The dosage of the other compound for treating obesity, an obesity-related disorder, metabolic syndrome or a cognition deficit disorder can be determined from published material, and may range from about 1 to about 1000 mg per dose.

Kits

When separate pharmaceutical compositions comprising an $H_3$ antagonist and another compound for treating obesity, an obesity-related disorder, metabolic syndrome or a cognition deficit disorder are to be administered, they can be provided in a kit comprising in a single package, one container comprising an $H_3$ antagonist in a pharmaceutically acceptable carrier, and a separate container comprising a compound for treating obesity, an obesity-related disorder, metabolic syndrome or a cognition deficit disorder in a pharmaceutically acceptable carrier, with the $H_3$ antagonists and other compounds being present in amounts such that the combination is therapeutically effective. A kit is advantageous for administering a combination when, for example, the components must be administered at different time intervals or when they are in different dosage forms.

Compounds of formula (I) can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

EXAMPLES

General Methods

The starting materials and reagents used in preparing compounds described are either available from commercial suppliers such as Aldrich Chemical Co. (Wisconsin, USA) and Acros Organics Co. (New Jersey, USA) or were prepared using methods well-known to those skilled in the art of organic synthesis. All commercially purchased solvents and reagents were used as received. LCMS analysis was performed using an Applied Biosystems API-100 mass spectrometer equipped with a Shimadzu SCL-10A LC column: Altech platinum C18, 3 µm, 33 mm×7 mm ID; gradient flow: 0 minutes, 10% $CH_3CN$; 5 minutes, 95% $CH_3CN$; 7 minutes, 95% $CH_3CN$; 7.5 minutes, 10% $CH_3CN$; 9 minutes, stop. Flash column chromatography was performed using Selecto Scientific flash silica gel, 32-63 mesh. Analytical and preparative TLC was performed using Analtech Silica gel GF plates. Chiral HPLC was performed using a Varian PrepStar system equipped with a Chiralpak OD column (Chiral Technologies).

Example 1

Preparation of Compound 1A

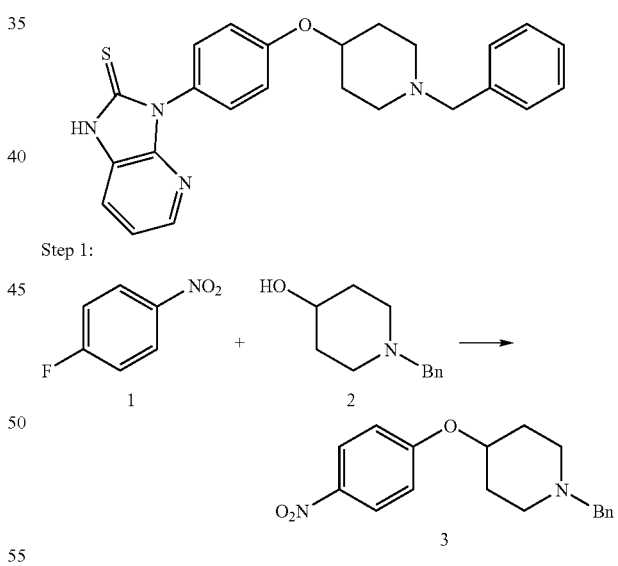

To a stirred suspension of compound 2 (20.1 g, 0.100 mol) in tert-butanol (120 mL) was added portionwise potassium tert-butoxide (9.5 g, 0.084 mol). The mixture was heated under reflux for 30 min, yielding a homogeneous solution, which was cooled to 35° C., and to which was added compound 1 (12.7 g, 0.09 mol) in a single portion. An exothermic reaction raised the internal temperature to 68° C. When the exotherm had subsided, the mixture was heated to reflux for 30 min. Solvent was removed under vacuum, and the residue was treated with ice water, which resulted in formation of an insoluble fraction. Crude product 3 was isolated by filtration of the insoluble solid. Crude 3 (21 g, 0.0672 mol) was treated with a mixture of 2N HCl and EtOAc, and the resultant mixture was stirred at room temperature for 10 min. The insoluble material was filtered and washed thoroughly with water and EtOAc to provide 18.1 g of the HCl salt of compound 3, mp 287-289° C. The HCl salt was stirred in a mixture of 1N NaOH (150 mL) and DCM (250 mL) until all solids dissolved. The organic phase was separated, washed with water and dried (anhydrous MgSO₄). The drying agent was filtered, and the filtrate was stripped of solvent under vacuum to provide 15.7 g of the free base form of compound 3 as a beige solid.

Step 2:

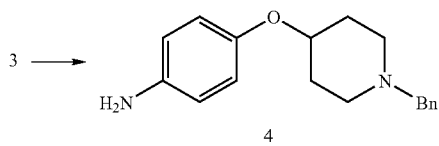

4

A solution of compound 3 (9.0 g, 28.8 mmol) in warm DMF (40 mL) was diluted with EtOH (120 mL). The solution was cooled to room temperature, and to it was added half a teaspoon of Raney nickel paste (50% water). The resultant mixture was hydrogenated at 35 psi until hydrogen uptake leveled off. The spent catalyst was filtered through a pad of celite, and the filtrate was concentrated under vacuum. The residue was partitioned between water and Et₂O:EtOAc (1:1). The organic extract was washed with water, dried over anhydrous MgSO₄ and filtered. The filtrate was concentrated under vacuum to provide 7.8 g of compound 4 as syrup, which was used without purification in next step.

Step 3:

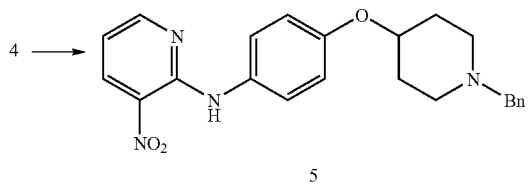

5

A stirred mixture of compound 4 (3.5 g, 12.4 mmol), anhydrous K₂CO₃ (1.87 g, 13.5 mmol) and 2-chloro-3-nitropyridine (1.97 g, 12.4 mmol) in anhydrous toluene (50 mL) was heated under reflux for 18 h. TLC revealed a mixture of starting material and product. Therefore, additional quantities of 2-chloro-3-nitropyridine (0.5 g) and anhydrous K₂CO₃ (0.5 g) were introduced, and heating under reflux was continued for another 18 h. After cooling to room temperature, the mixture was treated with ice-water and extracted with toluene. Combined toluene extracts were washed successively with 0.5N aqueous NaOH and water, and were then treated with 0.5N HCl (200 mL). The red precipitate which formed was filtered to provide 3.3 g of the crude HCl salt of compound 5. The acidic aqueous phase was separated, washed with EtOAc and basified with 10% aqueous NaOH. The resultant red precipitate was filtered and washed with water to provide 1.3 g of the free base form of compound 5. A mixture of HCl salt (3.2 g) and free base (1.3 g) were partitioned between 0.5N NaOH and DCM. The organic phase was washed with water and dried (anhydrous MgSO₄). The drying agent was filtered, and the filtrate was concentrated under vacuum to provide 4.5 g of the free base form of compound 5, which was used in the next step without purification.

Step 4:

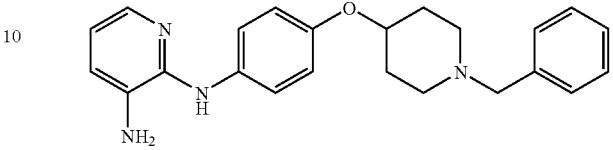

6

A solution of compound 5 (2.2 g, 5.5 mmol) in warm DMF (30 mL) was diluted with EtOH (60 mL). The solution was cooled to room temperature, and to it was added half a teaspoon of Raney nickel paste (50% water). The resultant mixture was hydrogenated at 44 psi until hydrogen uptake leveled off. The spent catalyst was filtered through a pad of celite, and the filtrate was concentrated under vacuum. The residual oil was partitioned between water and EtOAc. The organic extract was washed with water, dried over anhydrous MgSO₄ and filtered. The filtrate was concentrated under vacuum to produce a solid that was triturated with hexane. Filtration yielded 1.58 g of compound 6. MH⁺ 375

Step 5:

To a stirred solution of compound 6 (0.59 g, 1.58 mmol) in 90% EtOH (35 mL) was added carbon disulfide (0.5 mL). The resultant solution was heated under reflux for 18 h, and was then concentrated under vacuum to a solid residue, which was triturated with water and filtered. The crude product was crystallized from EtOH to provide 0.139 g of title compound. MH⁺ 417

Example 2

Preparation of Compound 2A

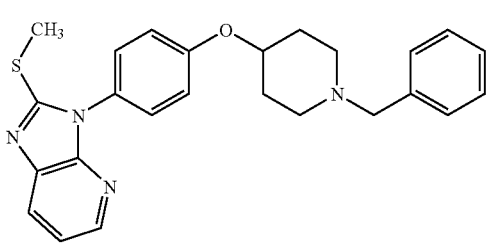

2A

To a stirred solution of compound 1A (0.1 g, 0.24 mmol) and powdered NaOH (24 mg, 0.6 mmol) in MeOH (10 mL) was added dimethylsulfate (38 mg, 0.3 mmol). After stirring at room temperature for 18 h, the reaction mixture was diluted with water and the insoluble pink solid filtered. The solid was crystallized from EtOAc-hexane (including treatment with decolorizing carbon) to provide 38 mg of title compound as a cream-colored solid. MH+ 431

Example 3

Preparation of Compound 3A

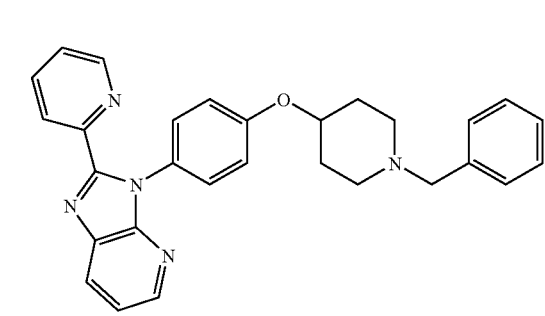

Step 1:

6 →

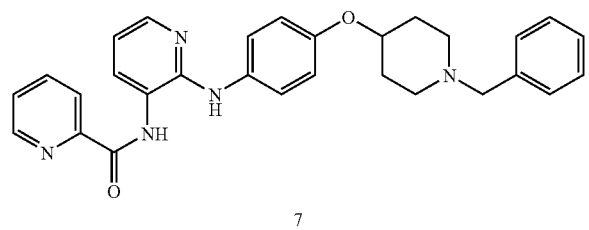

To a stirred, ice-cooled solution of compound 6 (0.73 g, 1.95 mmol) and Et$_3$N (2.0 mL) in dry DCM (30 mL) was added picolinoyl chloride hydrochloride (0.38 g, 2.15 mmol) in a few portions. Stirring at ~5° C. was maintained for 5 min, then continued at room temperature for 18 h. The reaction mixture was treated with ice water, and the organic phase was separated and washed with water, dried over anhydrous MgSO$_4$, filtered and concentrated to a viscous residue, which contained significant unchanged starting material, according to TLC. Therefore, this residue (0.85 g) was dissolved in dry DCM (30 mL), and to this solution were added picolinoyl chloride hydrochloride (0.38 g, 2.15 mmol) and Et$_3$N (1 mL). The reaction solution was stirred at room temperature for 18 h. The reaction mixture was treated with water, and the organic phase was separated and washed with water, dried over anhydrous MgSO$_4$, filtered and concentrated to a viscous residue, which was purified using flash column chromatography on silica gel, eluting with DCM-MeOH (95:5) to provide compound 7 as a glass (810 mg). MH+ 480

Step 2:

To a stirred solution of compound 7 (0.55 g, 1.15 mmol) in EtOH (20 mL) was added dropwise concentrated H$_2$SO$_4$ (2.5 mL). The solution was heated under reflux for 18 h, and was then poured into ice-water, basified with 25% aqueous NaOH and extracted with DCM. Combined organic extracts were washed with water, dried (anhydrous MgSO$_4$) and filtered. The filtrate was concentrated under vacuum to provide a viscous residue, which was purified using flash column chromatography on silica gel, eluting with EtOAc-MeOH (97:3) to provide title compound as a beige solid (140 mg). MH+ 462

Example 4

Preparation of Compound 4A

Step 1:

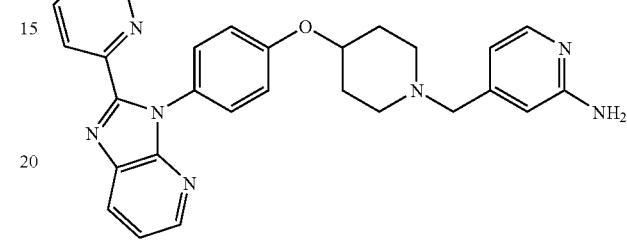

To a stirred mixture of potassium tert-butoxide (19 g, 0.169 mol) and compound 8 (32.7 g, 0.162 mol) in tert-butanol (200 mL) at 50° C. was added compound 1 (25.2 g, 0.178 mol) in one portion. After being heated under reflux for 0.5 h, the mixture was cooled to room temperature, diluted with ether and treated with water. The organic phase was separated, washed with water, dried over anhydrous MgSO$_4$, and filtered. The filtrate was concentrated to a solid which was triturated with hexane and filtered to give 42 g of compound 9.

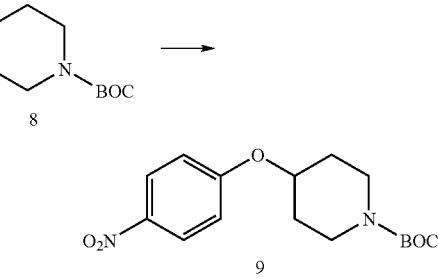

A suspension of compound 9 (20 g, 0.062 mol) in DMF (40 mL) and EtOH (130 mL) was mixed with a half-teaspoonful of 50% Raney Nickel (aqueous slurry) and hydrogenated at 38 psi for 0.5 h. The spent catalyst was filtered off, and the filtrate was concentrated to a solid which was triturated with ether-hexane (1:2) and filtered to produce 17 g of compound 10.

Step 3:

10 →

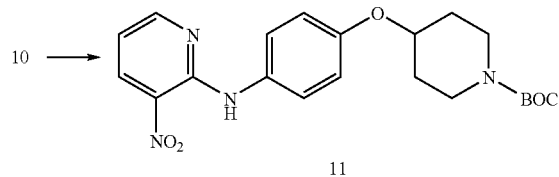

11

A stirred mixture of compound 10 (HCl salt) (4.28 g, 13 mmol), anhydrous potassium carbonate (3.87 g, 28 mmol), 2-chloro-3-nitropyridine (2.06 g, 13 mmol) and NaI (0.1 g) in toluene (80 mL) was heated under reflux for 48 h. After being cooled to room temperature, the mixture was treated with water and extracted with ether. Ether extracts were washed with water, dried over anhydrous MgSO$_4$, and filtered. The filtrate was concentrated to a solid which was triturated with ether-hexane (1:2) and filtered to give 5 g of compound 11.

Step 4:

11 →

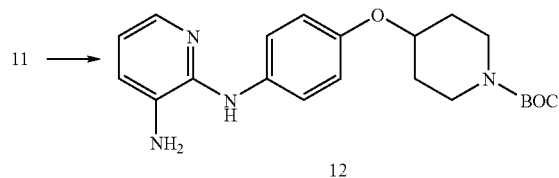

12

A solution of compound 11 (5 g, 12 mmol) in THF (60 mL) and tert-butanol (40 mL) was hydrogenated in the presence of 3 g of 50% Raney Nickel at 25 psi for 18 h. The spent catalyst was filtered off, and the filtrate was concentrated to a solid which was purified using chromatography on silica gel with EtOAc—CH$_2$Cl$_2$ (1.5:8.5) to produce 3 g of compound 12.

Step 5

12 →

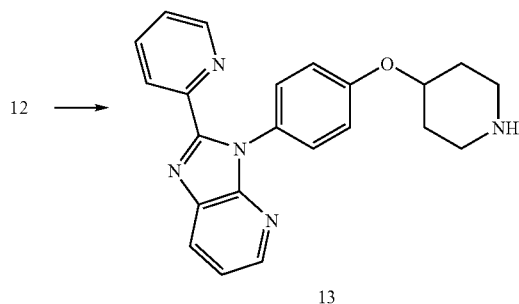

13

To a stirred solution of compound 12 (11.87 g, 4.87 mmol) and Et$_3$N (1.5 mL) in DCM (30 mL) was added picolinoyl chloride hydrochloride (0.87 g, 4.87 mmol) in a few portions. After being stirred at room temperature for 18 h, the mixture was treated with water and the organic phase was separated. The organic solution was washed with water, dried over anhydrous MgSO$_4$, filtered and concentrated to a glass residue (2.4 g, ESI-MS: MH$^+$ 490). This residue (1 g, 2.05 mmol) in EtOH-conc H$_2$SO$_4$ (5:1, 24 mL) was heated under reflux for 18 h, diluted with ice water, basified with 50% aqueous NaOH and extracted with DCM. Organic extracts were concentrated to a glass, which was purified using column chromatography on silica gel, eluting with 7N methanolic ammonia-DCM (3:47) to produce 0.47 g of compound 23 (as a glass).

Step 6:

13 →

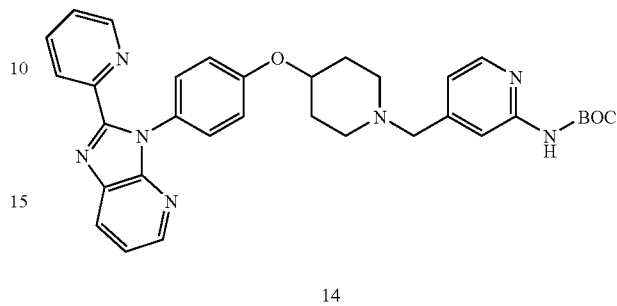

14

A mixture of compound 13 (0.43 g, 1.16 mmol), N-BOC-2-aminopyridine-4-carbaldehydealdehyde (for preparation, see WO2002032893) (0.284 g, 1.28 mmol) and NaBH(OAc)$_3$ (0.81 g, 3.84 mmol) in anhydrous DCM (40 mL) was stirred at room temperature for 48 h. The mixture was treated with water, and the organic phase was separated and concentrated to dryness in vacuo. The solid residue was triturated with a mixture of EtOAc and a 1% aqueous solution of maleic acid (40 mL). Insoluble solids were filtered and washed with EtOAc and water to provide 0.31 g of the maleate salt of compound 14.

Step 7:

A solution of the maleate salt of 14 (300 mg, 0.432 mmol) in a mixture of DCM (2 mL) and TFA (2 mL) was stirred for 2 h at room temperature, and was then concentrated under vacuum. The viscous residue was basified with 0.1N NaOH, and the resultant insoluble solid was crystallized from 5% MeOH-DCM and ether to provide 0.138 g of title compound. MH$^+$ 478

Example 5

Preparation of Compound 5A

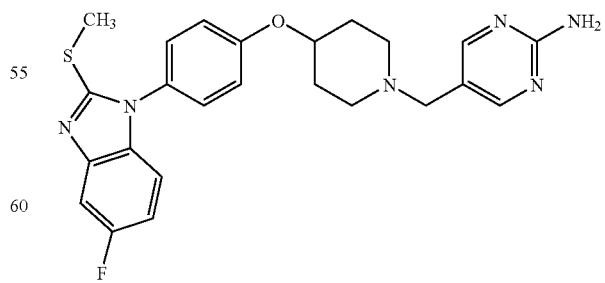

5A

Step 1:

10 ⟶

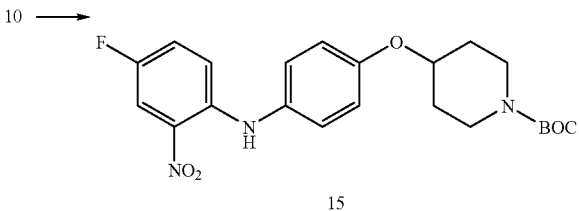

15

A stirred mixture of compound 10 (HCl salt) (12.0 g, 41 mmol), anhydrous potassium carbonate (6.80 g, 49 mmol) and 2,5-difluoronitrobenzene (7.17 g, 45 mmol) in molecular sieve-dried toluene (120 mL) was heated under reflux for 48 h. After cooling to room temperature, the mixture was treated with ice-water and extracted with EtOAc. Combined extracts were washed with water, dried over anhydrous MgSO₄, filtered and concentrated under vacuum to a syrup, which was flash chromatographed on silica gel. Elution with DCM, followed by DCM-MeOH (98:2) yielded 4.5 g of compound 15 as a red syrup.

Step 2:

15 ⟶

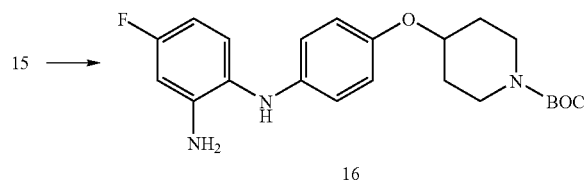

16

A solution of compound 15 (4.4 g, 12 mmol) in warm DMF (20 mL) was diluted with EtOH (80 mL). The solution was cooled in an ice-water bath, and to it was added half a teaspoon of Raney nickel paste (50% water). The resultant mixture was hydrogenated at 33 psi for 18 h. The spent catalyst was filtered off and the filtrate was concentrated under vacuum. The residue was diluted with water and extracted with ether. Combined extracts were washed with water, dried over anhydrous MgSO₄ and filtered. The filtrate was concentrated under vacuum to a solid residue, which was triturated with hexane. Filtration yielded 3.4 g of compound 16.

Step 3:

16 ⟶

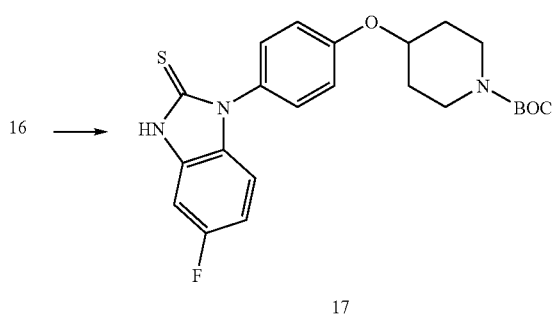

17

A solution of compound 16 (1.85 g, 4.6 mmol) and thiocarbonyldiimidazole (90%; 1.0 g, 5 mmol) in anhydrous THF (30 mL) was heated under reflux for 18 h. Solvent was removed under vacuum. The residue was triturated with 5% HCl in an ice-water bath. Insoluble solid was filtered, dissolved in EtOH (300 mL), washed with water and dried (anhydrous MgSO₄). The drying agent was filtered, and the filtrate was stripped of solvent under vacuum. The solid residue was triturated with hexane and filtered to provide 1.98 g of compound 17.

Step 4:

17 ⟶

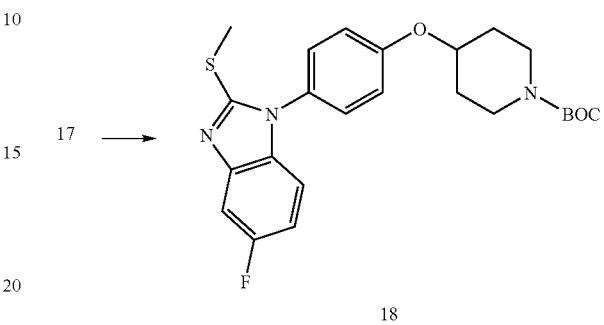

18

To a stirred mixture of compound 17 (1 g, 2.25 mmol) and powdered NaOH (0.185 g, 4.6 mmol) in MeOH (20 mL) was added dimethylsulfate (0.29 g, 2.3 mmol). After stirring at room temperature for 1 h, the reaction mixture was partitioned between water and diethyl ether. Combined extracts were washed successively with 5% aqueous NaOH and water, dried over anhydrous MgSO₄ and filtered. The filtrate was stripped of solvent in vacuo to provide 1 g of compound 28 as a glass.

Step 5:

18 ⟶

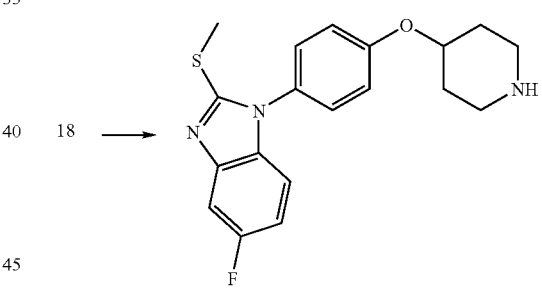

19

A solution of compound 18 (1 g, 2.19 mmol) and TFA (10 mL) in DCM (15 mL) was stirred at room temperature for 18 h. The reaction mixture was concentrated under vacuum. The residue was partitioned between 0.5N aqueous NaOH and diethyl ether. Combined extracts were washed with water and dried over anhydrous MgSO₄. Drying agent was filtered, and the filtrate was stripped of solvent under vacuum to provide 0.88 g of compound 19 as a syrup.

Step 6:

To a stirred solution of compound 19 (0.15 g, 0.42 mmol) in anhydrous DCM (20 mL) was added 2-aminopyrimidine-5-carbaldehyde (see WO2002032893) (0.062 g, 0.5 mmol), followed by NaBH(Oac)₃ (0.32 g, 1.5 mmol). The reaction mixture was stirred at room temperature for ~5 days and was then partitioned between 0.5 N aqueous NaOH and DCM. The organic extract was concentrated in vacuo to a solid residue, which was purified using flash column chromatography on silica gel, eluting with DCM-MeOH (96:4) to provide the title compound as a glass (102 mg). A solution of this free base form of the title compound (0.215 mmol) in EtOAc was mixed with a solution of maleic acid (25 mg, 0.215 mmol) in EtOAc. The mixture was cooled in an ice-water bath. The resultant precipitate was filtered to provide the maleate salt form of title compound. MH+ 465

Example 6

Preparation of Compound 6A

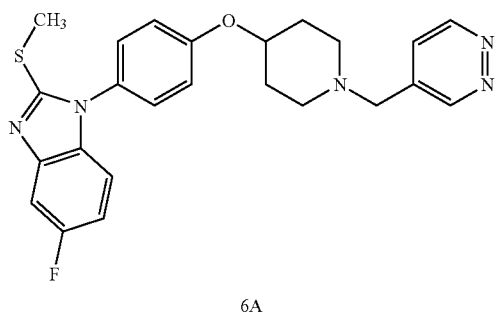

6A

The title compound was prepared using the procedure of Example 5, step 6, except that pyridazine-4-carbaldehyde (see WO2002032893) was used in place of 2-aminopyrimidine-5-carbaldehyde. MH+ 450

Example 7

Preparation of Compound 7A

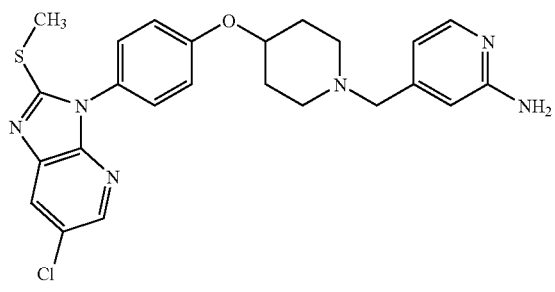

7A

Step 1:

10 →

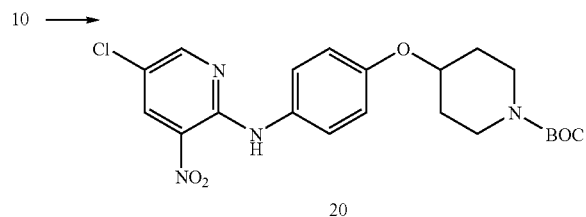

20

Compound 20 was prepared from compound 10 and 2,5-dichloro-3-nitropyridine using the method set forth in Example 6, step 1.

Step 2:

Compound 20 was converted into the title compound using the methods set forth in Example 5, steps 2-5, followed by procedures from Example 4, steps 6 and 7.

MH+ 481

Example 8

Preparation of Compound 8A

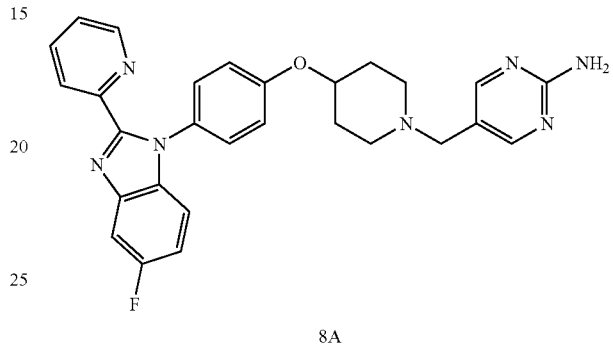

8A

Step 1:

16 →

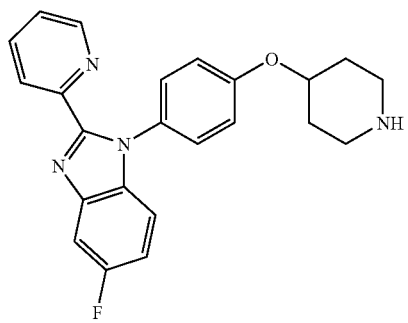

21

A solution of triphenylphosphine oxide (2.8 g, 10 mmol) in dry DCE (15 mL) was cooled to 0° C. in an ice-water bath, and to it was added, dropwise with stirring, a solution of triflic anhydride (0.85 ml, 5 mmol) in dry DCE (15 mL). A precipitate formed, and the resultant mixture was stirred at 0° C. for 15 min before adding a solution of picolinic acid (0.3 g, 2.5 mmol) and compound 16 (0.8 g, 2 mmol) in dry DCE (10 mL), along with a few drops of Et₃N. The mixture was stirred at 0° C. for 30 min, then at room temperature for 18 h. before pouring into water and basifying with 5% aqueous NaHCO₃. The aqueous mixture was extracted with DCM. The organic extract was washed with water and dried over anhydrous MgSO₄. Drying agent was removed by filtration, and the filtrate was concentrated under vacuum to a dark green syrup, which was subjected to flash column chromatography on silica gel, eluting first with EtOAc-hexane (1:1) (to remove triphenylphosphine oxide), then with DCM-7N methanolic ammonia (97:7) to provide a partially purified product. This material was re-subjected to flash chromatography, eluting with DCM-7N methanolic ammonia (95:5) to provide 230 mg of compound 21 as a glass.

Step 2:

Compound 21 was converted into title compound using the procedure from Example 5, step 6. MH+ 496

Example 9

Preparation of Compound 9A

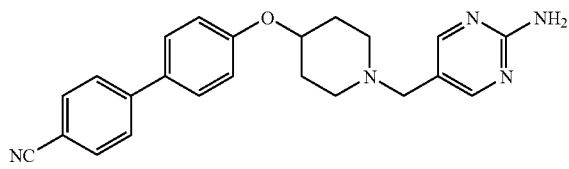

9A

Step 1:

8 →

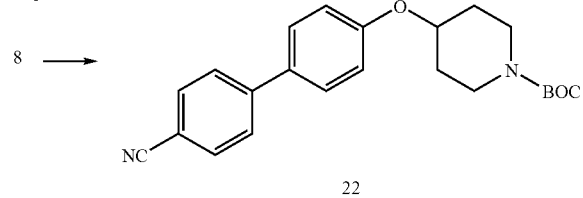

22

To a stirred suspension of polymer-supported triphenylphosphine (8.0 g, 24 mmol) in anhydrous DCM (80 mL) at 0° C. was added DEAD (3.2 g, 18 mmol) dropwise over ~3 min. This was followed by dropwise addition over 30 min of a solution of 4-cyano-4'-hydroxybiphenyl (3.2 g, 15 mmol) and 8 (3.15 g, 15 mmol) in anhydrous DCM (100 mL). The cooling bath was removed, and the reaction mixture was stirred at room temperature for 18 h. Insoluble material was removed by filtration through a pad of celite. The filtrate was concentrated under vacuum. The residue was treated with 0.5N aqueous NaOH and DCM, and the resultant emulsion was filtered to provide two separable phases. The organic layer was separated and washed with water, dried (anhydrous MgSO$_4$) and filtered. The filtrate was concentrated under vacuum to provide a viscous residue which was flash chromatographed on silica gel. Elution with DCM yielded 2.81 g of compound 22.

Step 2:

Compound 22 was converted into the title compound using the procedures from Example 5, steps 5 and 6. MH+ 386

Example 10

Preparation of Compound 10A

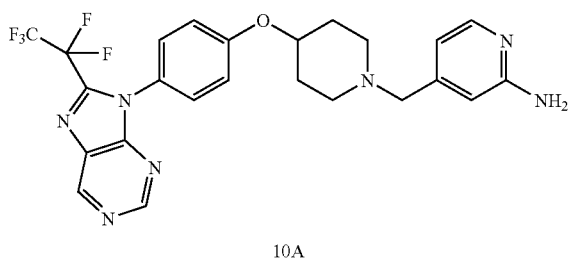

10A

-continued

Step 1:

10 →

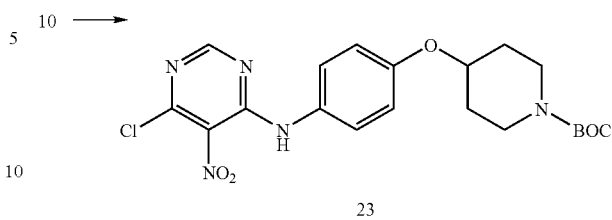

23

To a stirred, ice-cooled mixture of 4,6-dichloro-5-nitropyrimidine (5.30 g, 27.4 mmol) and K$_2$CO$_3$ (7.56 g, 54.8 mmol) in THF (60 mL) was added slowly a solution of compound 10 in THF (60 mL) over 20 min. The resultant mixture was stirred at 0° C. for 1 h. The reaction mixture was then treated with DCM (60 mL) and water (20 mL). Insoluble material was filtered, and the layers of the filtrate were separated. The aqueous layer was extracted with a second portion of DCM (40 mL). Combined extracts were washed with brine (30 mL), dried over anhydrous MgSO$_4$, filtered and concentrated under vacuum. The residue was purified using flash chromatography, eluting with DCM-EtOAc (8:1) to provide 9.82 g of compound 23 as a bright orange solid.

Step 2:

23 →

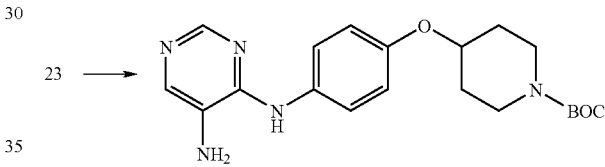

24

To a solution of nitro compound 23 (11.5 g, 25.5 mmol) in EtOH (250 mL) was added 20% palladium hydroxide-on-carbon catalyst (1.5 g), and the resultant mixture was hydrogenated for 16 h on a Parr shaker apparatus at an initial pressure of 40 psi. Catalyst was removed by filtration, and the filtrate was concentrated under vacuum to provide a dark gray solid, which was triturated with EtOH. Filtration yielded ~7.9 g of compound 24 as a gray solid deemed sufficiently pure for use in the next step.

Step 3:

24 →

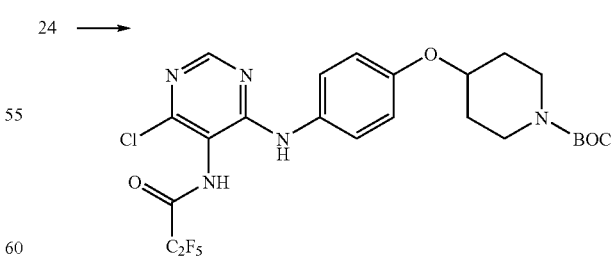

25

To a stirred solution of compound 24 (5.0 g, 13.0 mmol) and Et$_3$N (3.6 ml, 26.0 mmol) in DCM (50 mL), maintained at 0° C. in an ice-water bath, was added slowly via dropping funnel pentafluoropropionic anhydride (2.66 ml, 13.6 mmol).

The resultant mixture was stirred at 0° C. for 1 h, then at room temperature for 16 h. The reaction mixture was concentrated under vacuum, and the residue was flash chromatographed on silica gel, eluting with DCM-2N methanolic ammonia (12:1), to provide 6.53 g of compound 25 as a dark brown solid, containing some Et$_3$N, but sufficiently pure for use in the next step.

Step 4:

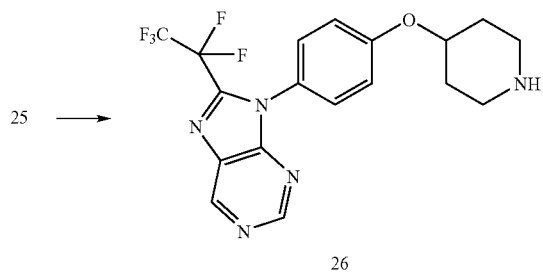

A stirred mixture of compound 25 (6.00 g, 11.3 mmol) and Eaton's reagent (7.7% wt. P$_2$O$_5$ in methanesulfonic acid) (50 mL) was heated at 80° C. for 16 h. The reaction mixture was poured onto ice (~30 g) and was basified to pH 10 by slow addition of 50% aqueous NaOH. The alkaline mixture was extracted with DCM (2×200 mL). Combined extracts were washed with brine (100 mL) and dried over anhydrous MgSO$_4$. Drying agent was filtered, and the filtrate was stripped of solvent under vacuum. The residue was flash chromatographed on silica gel, eluting with DCM-2N methanolic ammonia (12:1), to provide 2.84 g of compound 26 as a yellow solid.

Step 5:

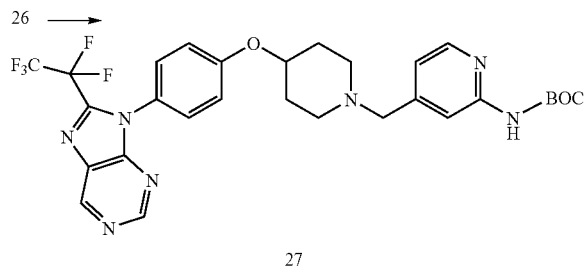

A solution of compound 26 (200 mg, 0.484 mmol) and N-BOC-2-aminopyridine-4-carbaldehydealdehyde (see WO2002032893) (129 mg, 0.581 mmol) in DCM (10 mL) was stirred at room temperature for 1 h before adding NaBH(OAc)$_3$ (205 mg, 0.968 mmol). The resultant mixture was stirred at room temperature for 16 h, and was then washed successively with 1N aqueous NaOH (10 mL) and brine (10 mL). Combined extracts were dried over anhydrous MgSO$_4$. Drying agent was filtered, and the filtrate was stripped of solvent under vacuum. The residue was flash chromatographed on silica gel, eluting with DCM-2N methanolic ammonia (20:1), to provide 315 mg of compound 27 as a yellow solid.

Step 6:

To a stirred solution of compound 27 (300 mg, 0.484 mmol) in anhydrous DCM (8 mL) was added TFA (2.0 mL), and stirring was continued at room temperature for 2 h. The reaction mixture was diluted with DCM (10 mL) and treated with a 1:1 (v/v) mixture of concentrated NH$_4$OH and water (6 mL). Layers were separated, and the aqueous phase was extracted with DCM (8 mL). Combined organic extracts were dried over anhydrous MgSO$_4$, filtered and concentrated under vacuum. The residue was purified using flash chromatography, eluting with DCM-2N methanolic ammonia (16:1), to provide 175 mg of the free base form of the title compound as a cream-colored solid. This free base was dissolved in EtOH (0.5 mL), to which solution was added maleic acid (75 mg, 2 eq). The resultant solution was concentrated in vacuo, and the residue was crystallized from EtOH to provide the bis-maleate salt form of title compound as an off-white solid. MH$^+$ 520

Example 11

Preparation of Compound 11A

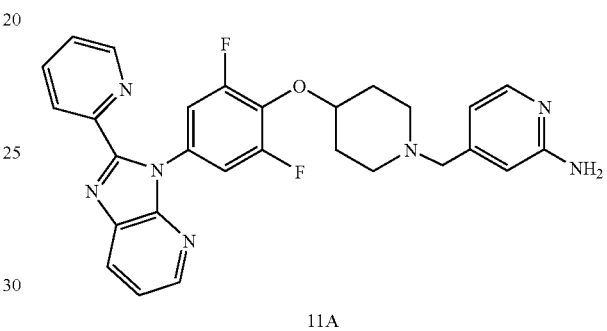

Step 1:

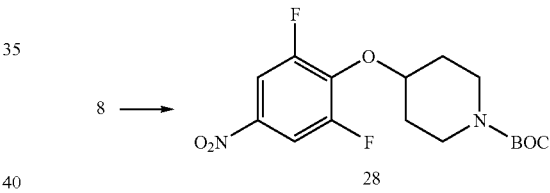

To a stirred mixture of potassium tert-butoxide (11.8 g, 105 mol) and compound 8 (22.5 g, 110 mol) in tert-butanol (150 mL) at 50° C. was added 3,4,5-trifluoronitrobenzene (18.0 g, 102 mmol) in one portion. The resultant mixture was stirred at 50° C. for 16 h. The reaction mixture was cooled to room temperature, diluted with ether (400 mL) and treated with water (250 mL). Layers were separated, and the aqueous phase was extracted with a second volume (200 mL) of ether. The combined extracts were washed with brine (200 mL), dried over anhydrous MgSO$_4$, filtered and concentrated to a residue which was purified using flash chromatography, eluting with EtOAc-hexanes (1:4), to provide 33.2 g of compound 28 as a light yellow solid.

Step 2:

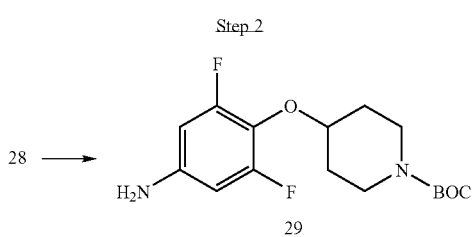

To a solution of nitro compound 28 (30.0 g, 83.8 mmol) in EtOH (100 mL)-THF (300 mL) was added Raney nickel (2800; slurry in water; 10 g), and the resultant mixture was hydrogenated for 16 h on a Parr shaker apparatus at an initial pressure of 35 psi. Catalyst was removed by filtration and washed with EtOH. The filtrate and washings were combined and concentrated under vacuum, and the residue was purified using flash chromatography, eluting with EtOAc-hexanes (1:1) to provide 26.8 g of compound 29 as a white solid.

Step 3:

29 ⟶

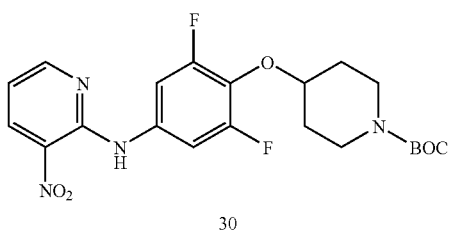

30

A mixture of 2-chloro-3-nitropyridine (3.95 g, 25 mmol), compound 29 (8.20 g, 25 mmol], K$_2$CO$_3$ (6.90 g, 50 mmol), palladium acetate (224 mg, 1 mmol) and BINAP (622 mg, 1 mmol) in toluene (80 mL) was heated at reflux for 16 h. The mixture was cooled to room temperature and partitioned with EtOAc (300 mL) and water (150 mL). Layers were separated, and the aqueous phase was extracted with a second portion of EtOAc (100 mL). Combined extracts were washed with brine (150 mL), dried over anhydrous MgSO$_4$, filtered and concentrated under vacuum. The residue was purified using flash chromatography, eluting with EtOAc-hexanes (1:4) to provide 9.23 g of nitro compound 30 as a bright orange solid.

Step 4

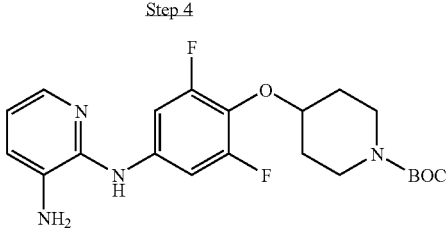

31

To a solution of nitro compound 30 (9.20 g, 20.4 mmol) in EtOH (50 mL)-THF (200 mL) was added Raney nickel (2800; slurry in water; 3.0 g), and the resultant mixture was hydrogenated for 16 h on a Parr shaker apparatus at an initial pressure of 40 psi. Catalyst was removed by filtration, and washed with EtOH. The filtrate and washings were combined and concentrated under vacuum, and the residue was purified using flash chromatography, eluting with EtOAc-hexanes (1:1) to provide 6.02 g of compound 31 as a red solid sufficiently pure for use in the next step.

Step 5:

32 ⟶

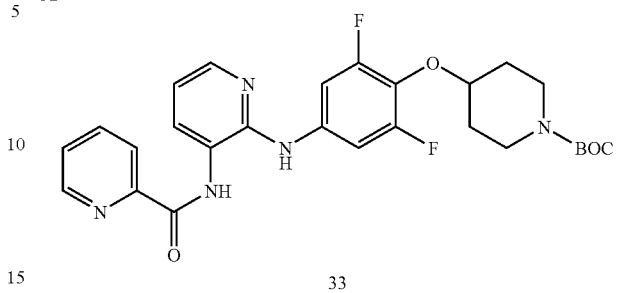

33

To a stirred mixture of compound 31 (2.50 g, 5.95 mmol) and Et$_3$N (1.66 ml, 7.15 mmol) in DCM (30 mL), maintained at 0° C. in an ice-water bath, was added in small portions 2-picolinoyl chloride hydrochloride (1.28 g, 7.15 mmol). The reaction mixture was diluted with DCM (20 mL), washed successively with 1N aqueous NaOH (20 mL) and brine (20 mL), dried over anhydrous MgSO$_4$, filtered and concentrated under vacuum. The residue was flash chromatographed on silica gel, eluting with EtOAc-hexanes (3:4), to provide 2.70 g of compound 32 as a light tan solid.

Step 6

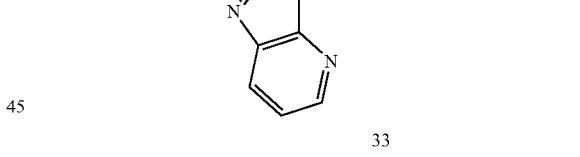

33

Concentrated H$_2$SO$_4$ (1 mL) was added to a solution of compound 32 in EtOH (5 mL). The reaction mixture was stirred in an oil bath maintained at 85° C. for 20.5 h, at which time a second portion of concentrated H$_2$SO$_4$ (1 mL) was added. Stirring at 85° C. was maintained for an additional 19.5 h. The mixture was then cooled to room temperature, treated with 50% aqueous NaOH (25 mL) and extracted with DCM (2×20 mL). Combined organic extracts were washed with brine, dried over anhydrous MgSO$_4$, filtered and concentrated under vacuum to provide crude compound 33, which was purified using flash chromatography, eluting with DCM-2N methanolic ammonia (12:1) to provide 150 mg of compound 33 as a cream-colored solid sufficiently pure for use in the next step.

Step 7:

Compound 33 was converted into the title compound using procedures of Example 10, steps 5 and 6. MH+ 514

Example 12

Preparation of Compound 12A

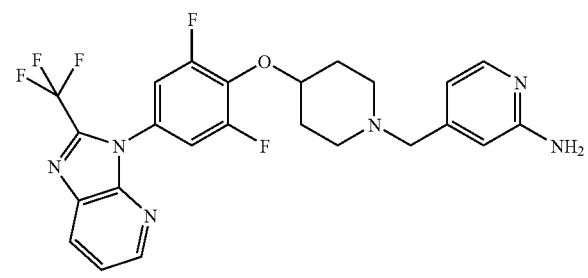

12A

Step 1:

31 ⟶

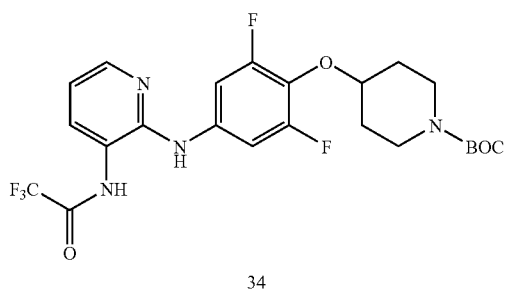

34

To a stirred solution of compound 31 and Et₃N (2.0 ml, 14.3 mmol) in DCM (40 mL), maintained at 0° C. in an ice-water bath, was added trifluoroacetic anhydride (1.15 g, 8.58 mmol). The reaction mixture was concentrated under vacuum, and the residue was flash chromatographed on silica gel, eluting with EtOAc-hexanes (3:2), to provide 3.56 g of compound 34 as a red foamy solid.

Step 2

34 ⟶

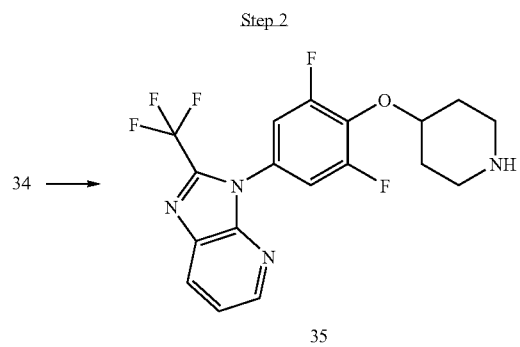

35

Compound 35 was converted into the title compound using the procedures of Example 10, steps 4-6. MH+ 505

Example 13

Preparation of Compound 13A

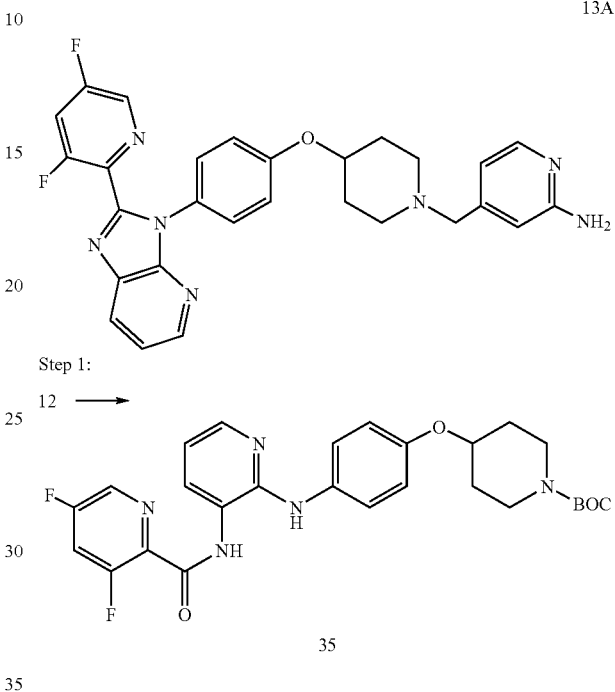

13A

Step 1:

12 ⟶

35

A solution of diamine 12, 3,5-difluoropicolinic acid (1.14 g, 7.16 mmol), HOBT (1.32 g, 9.75 mmol), EDC (1.86 g, 9.75 mmol) and DIPEA (5.0 ml, 28.7 mmol) in DCM (50 mL) was stirred at room temperature for 16 h. The reaction mixture was then washed successively with 1N aqueous NaOH (30 mL) and brine (30 mL) and dried (anhydrous MgSO₄). Drying agent was removed by filtration, and the filtrate was concentrated under vacuum. The residue was flash chromatographed on silica gel, eluting with EtOAc-hexanes (3:4), to provide 3.30 g of compound 35 as a brownish solid.

Step 2:

35 ⟶

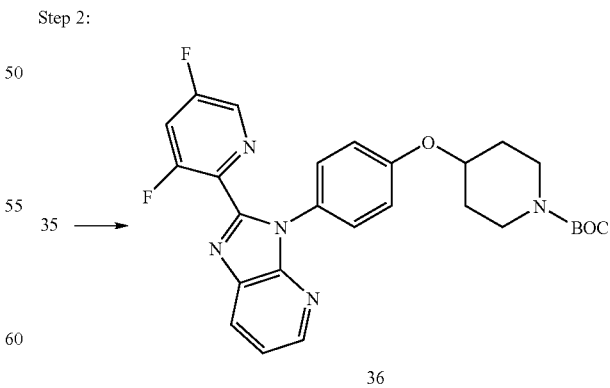

36

A stirred mixture of compound 35 (800 mg, 1.52 mmol) and ethylene glycol (8 mL) in a sealed glass pressure vessel (Chemglass) was heated at 120° C. for 16 h. The reaction mixture was allowed to cool to room temperature and was then partitioned between EtOAc (50 mL) and water (40 mL). The aqueous layer was extracted with a second volume of EtOAc (30 mL). Combined extracts were dried over anhydrous MgSO₄. Drying agent was filtered, and the filtrate was stripped of solvent under vacuum. The residue was flash chromatographed on silica gel, eluting with a stepped gradient of DCM-acetone (20:1->6:1), to provide 210 mg of compound 36 as a light yellow foamy solid.

Step 3

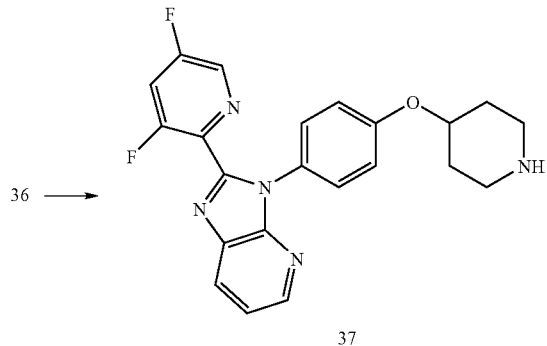

To a stirred solution of compound 36 (210 mg, 0.414 mmol) in anhydrous DCM (4 mL) was added TFA (1.0 mL), and stirring was continued at room temperature for 16 h. The reaction mixture was diluted with DCM (10 mL) and treated with a 1:1 (v/v) mixture of concentrated NH₄OH and water (6 mL). Layers were separated, and the aqueous phase was extracted with DCM (6 mL). Combined organic extracts were dried over anhydrous MgSO₄, filtered and the filtrate concentrated under vacuum to provide 167 mg of compound 37 as a white foamy solid.

Step 4:

Compound 37 was converted into the title compound using the procedures of Example 10, steps 5 and 6. MH⁺ 514

Example 14

Preparation of Compound 14A

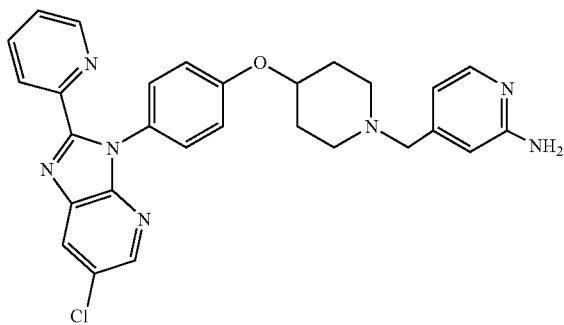

14A

-continued

Step 1:

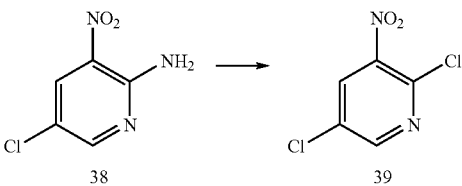

To a stirred solution of tert-butyl nitrite (55.2 ml, 466 mmol) and anhydrous Cu(II)Cl₂ (50.0 g, 372 mmol) in CH₃CN (500 mL), maintained at 70° C., was added 2-amino-5-chloro-3-nitrobenzene 38 (53.6 g, 310 mmol) portionwise over 30 min. The mixture turned from greenish to brown, and gas evolution was observed. Stirring at 70° C. was continued for 16 h. The reaction mixture was cooled and partitioned between 20% aqueous HCl (400 mL) and diethyl ether (1 l). Layers were separated, and the aqueous phase was extracted with EtOAc (500 mL). Combined extracts were washed successively with 20% aqueous HCl (200 mL) and brine (300 mL), dried over anhydrous MgSO₄, filtered and concentrated under vacuum. The residue was flash chromatographed on silica gel, eluting with EtOAc-hexanes (1:4), to provide 17.3 g of compound 39 as a yellow oil, which spontaneously crystallized upon standing at room temperature.

Step 2:

10 + 39 ⟶

40

A mixture of pyridine derivative 39 (15.0 g, 78.1 mmol), compound 10, K₂CO₃ (21.5 g, 156 mmol) and KI (1 g) in toluene (200 mL) was heated at 110° C. for 8 h. The mixture was cooled to room temperature and partitioned with DCM (500 mL) and water (400 mL). Layers were separated, and the aqueous phase was extracted with a second portion of DCM (300 mL). Combined extracts were washed with brine (250 mL), dried over anhydrous MgSO₄, filtered and concentrated under vacuum to provide 35.3 g of compound 40 as a dark red solid.

Step 3:

Compound 40 was converted into the title compound using the following sequence of procedures: Example 11, steps 4 and 5, followed by Example 13, steps 2 and 3, followed by Example 10, steps 5 and 6. MH+ 512

Example 15

Preparation of Compound 15A

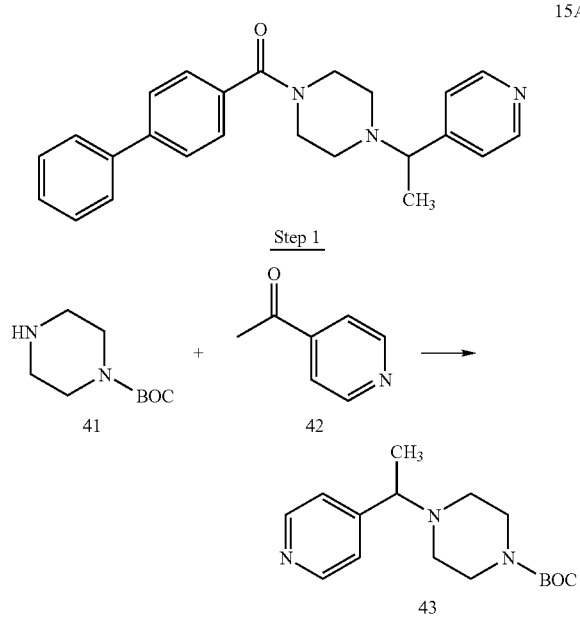

To a solution of N-BOC-piperazine 41 (3.8 g, 20.6 mmol) and 4-acetylpyridine 42 (2.0 g, 16.5 mmol) in ClCH$_2$CH$_2$Cl (15 mL) were added Ti(OPr)$_4$ (5.9 g, 20.6 mmol) and 3 molecular sieves. After stirring at room temperature under N$_2$ for 2 h and at 60° C. for another 2 h, the mixture was cooled to room temperature, Na(OAc)$_3$BH (4.9 g, 21.4 mmol) and ClCH$_2$CH$_2$Cl (85 mL) were added. The mixture was stirred at room temperature under N$_2$ for 72 h. Saturated NaHCO$_3$ aqueous solution was added to the mixture to form the solid. The mixture was then filtered through celite, the filtrate was extracted with DCM, dried over Na$_2$SO$_4$, concentrated in vacuum, and purified using flash chromatography to give 3.0 g of 43.

Step 2:

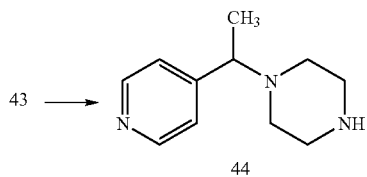

To a solution of 43 (3.0 g, 10.3 mmol) in DCM (60 mL) was added 4N HCl in 1,4-dioxane (15.4 ml, 61.8 mmol). The mixture was stirred at room temperature for 20 h. The solvent was removed in vacuum to give 3.6 g of crude 44.

Step 3:

To a solution of 44 (0.66 g, 2.2 mmol) in DCM (20 mL) were added biphenyl-4-carboxylic acid (0.42 g, 2.0 mmol), DIPEA (1.75 ml, 10.0 mmol), and PyBOP (1.04 g, 2.0 mmol).

After stirring at room temperature under N$_2$ for 20 h, the mixture was extracted with DCM and saturated aqueous NaHCO$_3$. The combined organic layers were dried over Na$_2$SO$_4$, concentrated in vacuum, and purified using flash chromatography to give 0.7 g of the title compound. MH+ 372

Example 16

Preparation of Compounds 16A and 16B

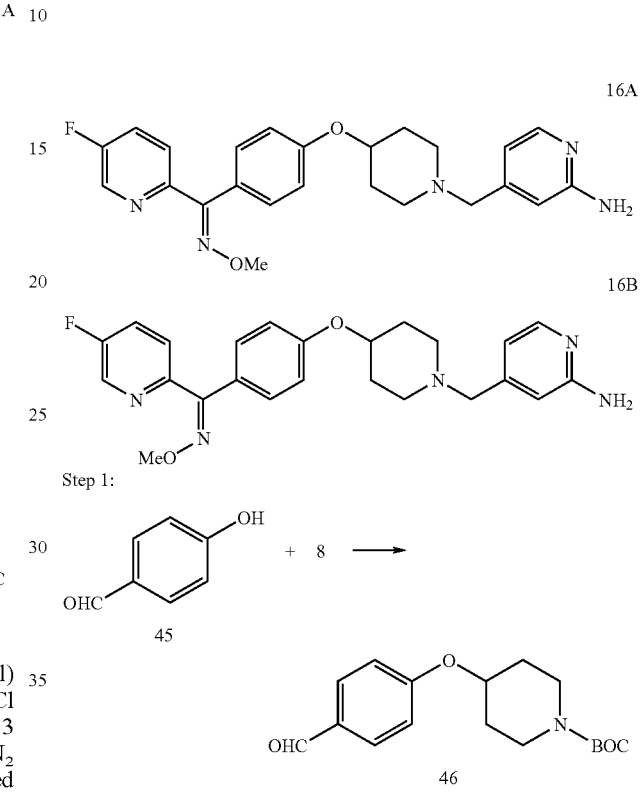

A mixture of phenol 45 (0.61 g, 5.0 mmol), piperidinol 8 (1.00 g, 5.0 mmol), 1,1'-(azodicarbonyl)dipiperidine (1.77 g, 7.0 mmol) and tributylphosphine (1.74 ml, 7.0 mmol) was stirred for 12 h at room temperature. The reaction mixture was subjected to aqueous work-up—EtOAc extraction, followed by flash chromatography (DCM) to produce 0.36 g of compound 46 as a colorless oil.

Step 2:

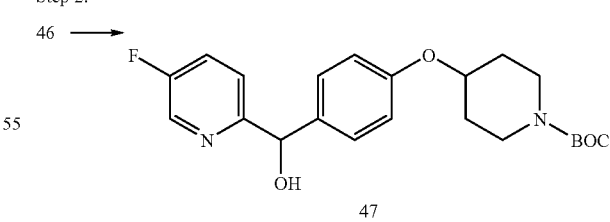

A solution of 2-bromo-5-fluoropyridine (0.29 g, 1.63 mmol) in toluene (6 mL) was added slowly to a solution of n-BuLi (2.5M in hexanes; 0.7 ml, 1.75 mmol) in toluene (10 mL) cooled to −78° C. and the mixture was stirred at −78° C. for 30 min. A solution of aldehyde 46 (0.36 g, 1.16 mmol) in toluene (5 mL) was added and the reaction mixture was stirred at −78° C. for 2 h. It was quenched with AcOH at −78°

C. and diluted with water. The product was extracted with DCM and the organic layer was dried over $Na_2SO_4$. Purification by flash chromatography (0-1% MeOH/DCM) provided 0.30 g of alcohol 47 as a yellow oil.

Step 3:

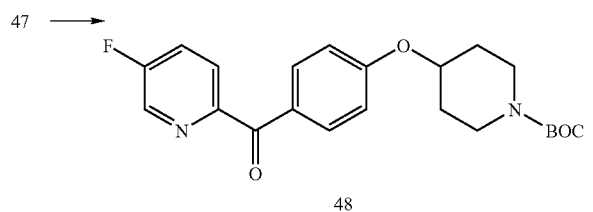

To a solution of alcohol 47 (0.30 g, 0.74 mmol) in DCM (6 mL) was added saturated aqueous solution of $NaHCO_3$ (0.75 g, 0.89 mmol) and NaBr (0.004 g, 0.037 mmol). The mixture was cooled to 0° C. and TEMPO (0.001 g, 0.007 mmol) was added followed by 0.7 M (2.5 ml, 1.48 mmol) commercial bleach (NaOCl) in portions over 15 min. The reaction mixture was stirred at 0° C. for 30 min and it was quenched with saturated aqueous $Na_2S_2O_3$ solution. The product was extracted with DCM and the organic layer was dried over $Na_2SO_4$. Purification by flash chromatography (0-0.5% MeOH/DCM) provided 0.20 g of 48 as a white solid.

Step 4:

48 ⟶

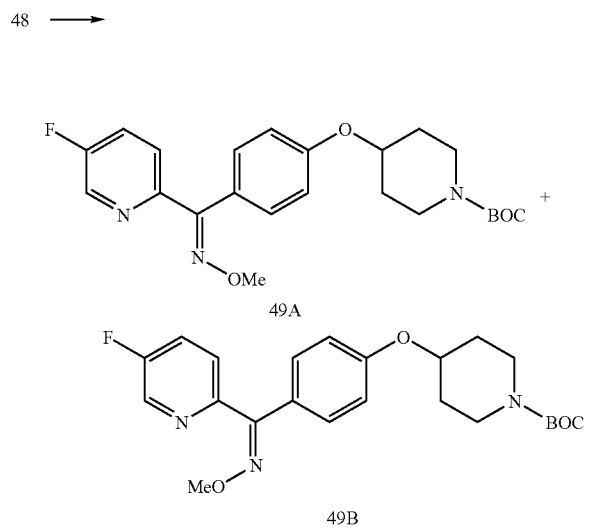

To a solution of 48 (0.19 g, 0.47 mmol) in pyridine (1 mL) was added methoxylamine hydrochloride (0.072 g; 0.095 mmol), and the reaction mixture was stirred at 80° C. overnight. Pyridine was removed and saturated aqueous $NaHCO_3$ solution was added. The product was extracted with DCM. The organic layer was dried over $Na_2SO_4$ and concentrated to provide 0.2038 g (100%) of the crude product (mixture of oximes 49A and 49B) as a yellowish solid. Separation of two isomers was performed by HPLC (OD chiralpak; 5% IPA/hexanes with 0.1 DEA; 15 ml/min) to produce 0.044 g of E-oxime 49A as a clear oil and 0.056 g of Z-oxime 49B as a white solid.

Step 5:

Compounds 49A and 49B were converted into Compounds 16A ($MH^+$ 436) and 16B ($MH^+$ 436), respectively, by using the procedures of Example 13, step 3, followed by Example 10, steps 5 and 6.

Example 17

Preparation of Compound 17A

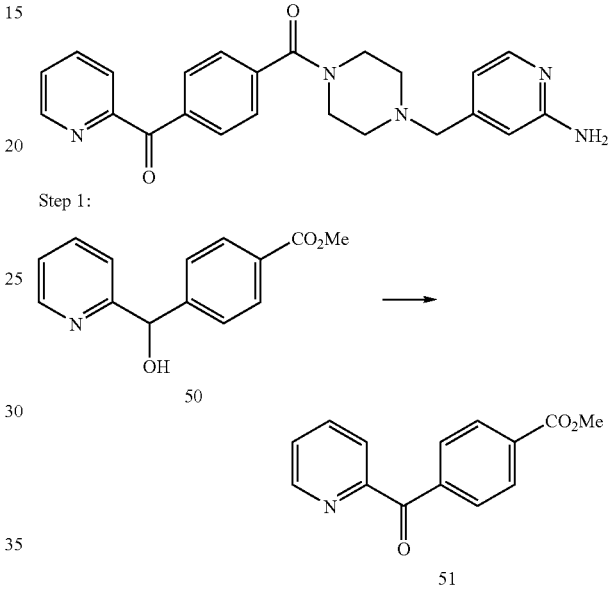

Compound 50 was prepared from 2-bromopyridine and methyl 4-formylbenzoate using the procedure of Example 16A, step 2, except that THF was used instead of toluene as the solvent.

To a solution of 50 (1.3 g; 5.33 mmol) in dioxane (50 mL) was added $MnO_2$ (2.32 g, 26.6 mmol) and conc. $H_2SO_4$ (0.2 mL). The reaction mixture was stirred at 75° C. overnight, cooled down, diluted with MeOH and filtered. The precipitate was washed repeatedly with MeOH and DCM, and the filtrate was combined and concentrated to produce 0.50 g of ketone 51.

Step 2:

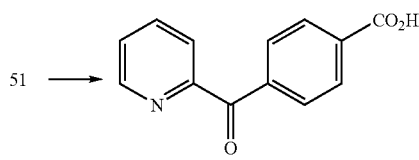

A mixture of 51 (0.50 g, 2.1 mmol) and LiOH monohydrate (0.12 g, 2.9 mmol) in dioxane—water was stirred overnight at 70° C. The reaction mixture was concentrated to dryness to produce crude 52, which was used without purification in the next step.

Step 3

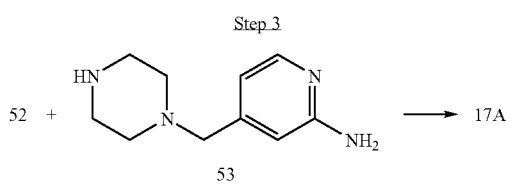

Compound 53 was prepared as described in WO2002032893.

Compounds 52 and 53 were reacted following the procedure of Example 13, step 1, to provide the title compound. MH⁺ 402

Example 18

Preparation of Compound 18A

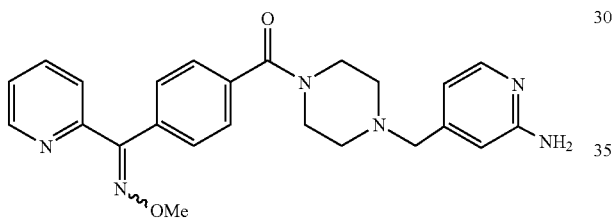

The title compound was prepared from the compound 17A using the procedure of Example 16A, step 4. MH⁺ 431

Example 19

Preparation of Compound 19A

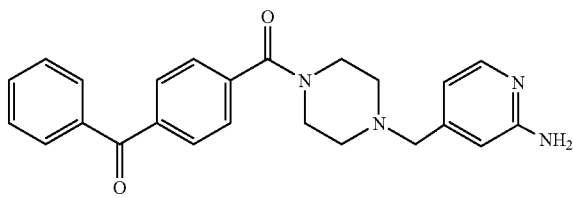

The title compound was prepared from 4-benzoylbenzoic acid and compound 53 using the procedure of Example 13, step 1. MH⁺ 401

Example 20

Preparation of Compound 20A

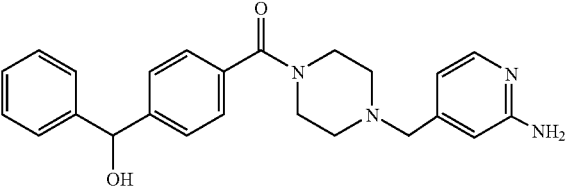

To a solution of the compound 19A (0.10 g; 0.25 mmol) in MeOH (20 mL) was added NaBH₄ (0.029 g, 0.75 mmol). The mixture was stirred for 2 h at room temperature, acidified with 4 N HCl in dioxane, filtered and concentrated in vacuo. The residue was redissolved in 10% MeOH/DCM with 0.5% aqueous NH₄OH. The solution was filtered and concentrated, and the residue was treated with 4 N HCl in dioxane to produce, after concentration, 0.12 g of HCl salt of the title compound as an off-white solid. MH⁺ 403

Example 21

Preparation of Compound 21A

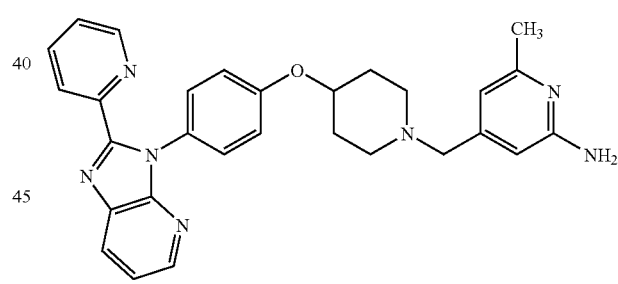

Step 1:

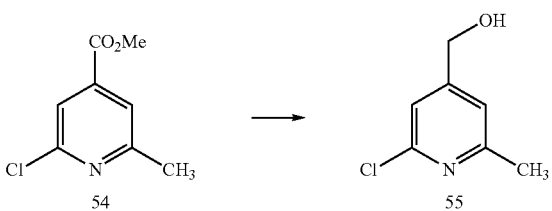

LiAlH₄ (10.0 g, 0.264 mol, 1.24 eq) was portionwise added to a solution of methyl-2-chloro-6-methylpyridine-4-carboxylate 54 (39.62 g, 0.213 mol) in dry THF (800 mL) at room temperature, with stirring, over a period of 1.4 h. The resulting mixture was stirred for 1 h and quenched with water. Then 15% aqueous NaOH (100 mL) was added, followed by aqueous sodium-potassium tartrate (1 l). The resulting mixture was stirred for a further 1.25 h and extracted with DCM (2×1 l) to give, after concentration, (2-chloro-6-methylpyridin-4-yl)-methanol 55 (31.06 g, 93%) as a yellow solid.

Step 2:

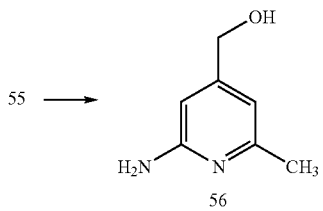

A bomb was charged with 55 (30.0 g, 0.190 mol) and aqueous conc NH₃ (225 mL) and the resulting mixture was heated at 210° C. for 20 h. The system was cooled to room temperature, the volatiles removed under vacuo and the residue purified using column chromatography (DCM: MeOH/ NH₃ 0.4N 9:1) to give (2-amino-6-methylpyridine-4-yl)-methanol as a mixture of free base and hydrochloride salt, which was redissolved in DCM: i-PrOH 1:1 (1 l) and treated with 20% aqueous NaOH (500 mL). The layers were separated and the organic phase extracted with DCM: i-PrOH 1:1 (1×1 l). The combined organic phase was dried and the solvent evaporated to give (2-amino-6-methylpyridine-4-yl)-methanol 56 (15.51 g, 59%) as pale orange crystals.

Step 3:

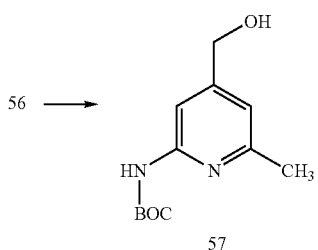

Di-tert-butyl dicarbonate (105.75 g, 0.485 mol, 4.33 eq) was added to a stirred solution of 56 (15.51 g, 0.112 mol) in tert-butyl alcohol (500 mL) at room temperature. The resulting mixture was heated at 95° C. for 19 h under a N₂ atmosphere, then was cooled to room temperature and the solvent evaporated under vacuo. The resulting brown oil was purified using column chromatography (EtOAc:hexanes 1:1) to give the diprotected aminoalcohol (38.25 g) as a yellow solid. Then, 25% aqueous NaOH (150 mL) was added to a solution of the above material in MeOH (500 mL) over a period of 10 min. The resulting mixture was stirred for 1 h, diluted with water (200 mL) and extracted with DCM (2×750 mL) to give 57 (21.0 g, 79% over two steps) as an orange foam.

Step 4:

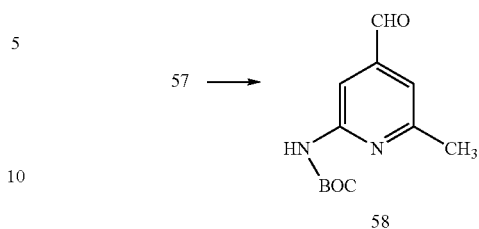

Dess-Martin periodinane (50.0 g, 0.118 mol, 1.34 eq) was portionwise added to a solution of 57 (21.0 g, 0.088 mol) in DCM:pyridine 10:1 (1.1 l). The resulting solution was stirred at room temperature for 2 h and then, water (700 mL) was added. The mixture was stirred for a further 5 min, then the layers were separated. The aqueous layer was extracted with DCM (1×1 l), the combined organic phase dried and the solvent evaporated to give a brown solid which was purified using column chromatography (EtOAc:hexane 1:2) to afford 58 (20.5 g, 99%) as a pale orange solid.

Step 5:

13 + 58 →

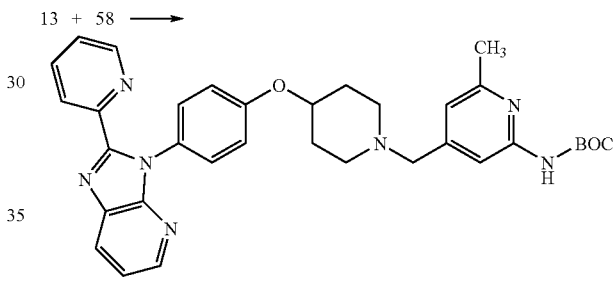

Compound 59 was prepared using the procedure of Example 10, step 5.

Compound 59 was converted into the title compound using the procedure of Example 10, step 6. MH⁺ 492

Example 22

Preparation of Compound 22A

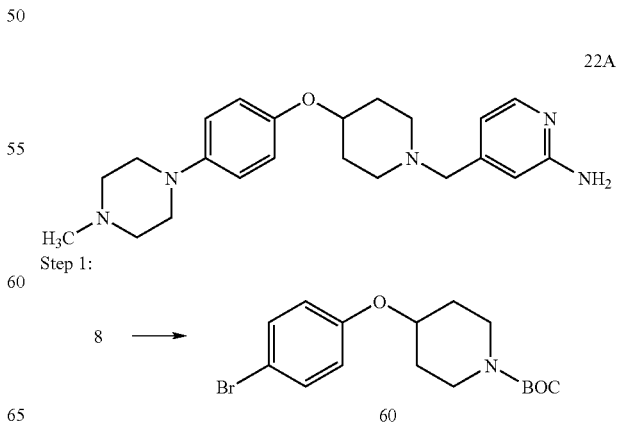

Step 1:

8 →

To a stirred solution of 4-bromophenol (8.52 g, 0.049 mol), 18 (8.25 g, 0.041 mol), PPh$_3$ (12.9 g, 0.049 mol) in dry THF (100 mL) was added DEAD (8.57 g, 0.049 mol) slowly. The mixture was allowed to stir in a sealed flask at 50° C. for 12 h. The mixture was diluted with ether, washed with 1N NaOH (2×), brine, dried and concentrated in vacuo. Flash chromatography (EtOAc:Hexanes/1:9) afforded 60 (8.50 g, 48% yield).

Step 2:

60 → 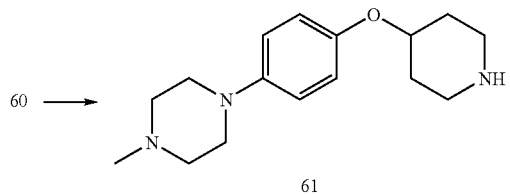

61

The mixture of 69 (800 mg, 2.25 mmol), Pd$_2$(dba)$_3$ (206 mg, 0.225 mmol), P(tBu)$_3$ (10 wt % in hexanes, 730 mg, 0.36 mmol), NaOtBu (324 mg, 3.37 mmol) and N-methylpiperazine (337 mg, 3.37 mmol) was stirred at room temperature in toluene (6 mL) for 48 h. The mixture was diluted with DCM and filtered. Flash chromatography (MeOH:DCM 1:20) afforded a brown oil. The oil was dissolved in DCM (5 mL) and TFA (5 mL). The solution was stirred at room temperature for 1 h and concentrated in vacuo. The resulting residue was stirred in DCM and 1N NaOH for 10 min. The DCM layer was washed with brine and concentrated in vacuo to give the amine 61 (550 mg, 89%).

Step 3:

Compound 61 was converted into the title compound using the procedure of Example 10, steps 5 and 6. MH$^+$ 382

Using the method described above, compounds 23A-69A were prepared:

| Compound | Structure | (M + H) |
|---|---|---|
| 23A | 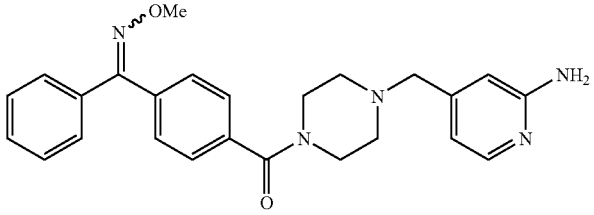 | 430 |
| 24A | 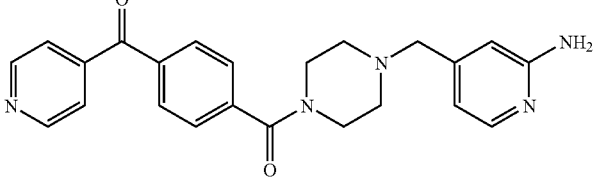 | 402 |
| 25A | 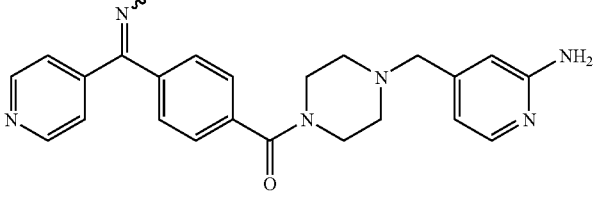 | 431 |
| 26A | 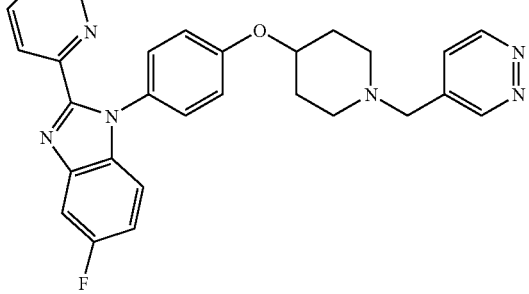 | 481 |

| Compound | Structure | (M + H) |
|---|---|---|
| 27A | 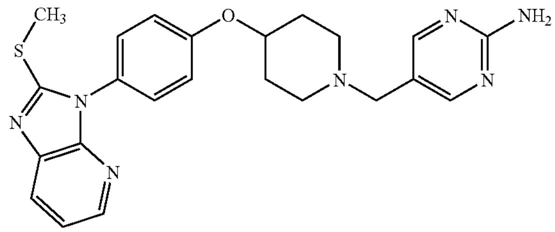 | 448 |
| 28A | 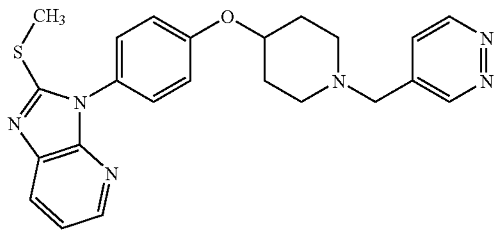 | 433 |
| 29A | 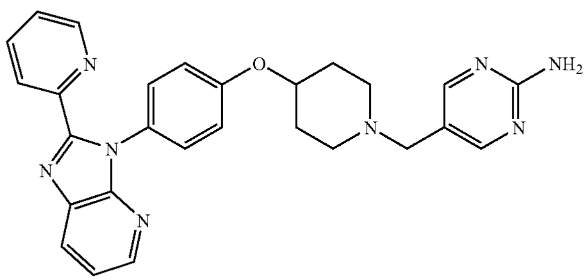 | 479 |
| 30A | 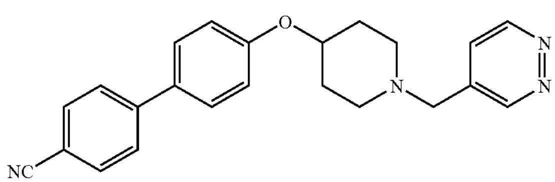 | 371 |
| 31A | 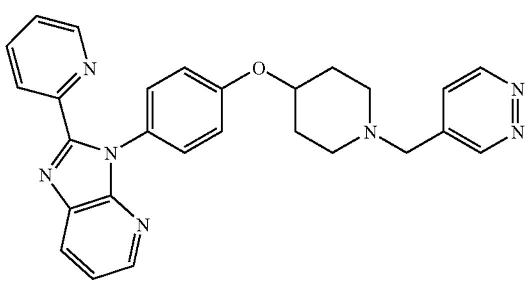 | 464 |
| 32A | 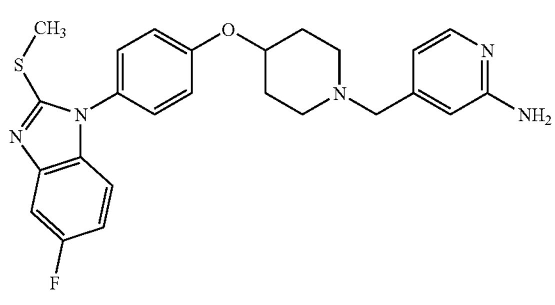 | 464 |

| Compound | Structure | (M + H) |
|---|---|---|
| 33A | 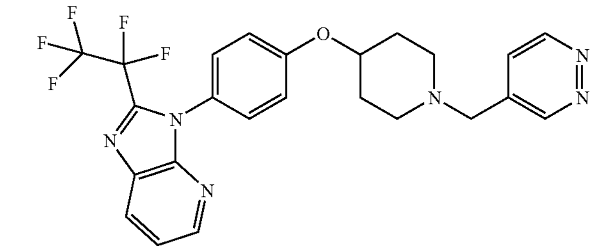 | 505 |
| 34A | 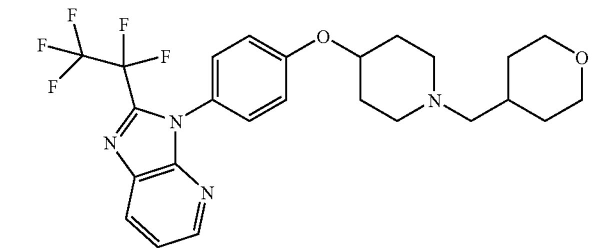 | 511 |
| 35A | 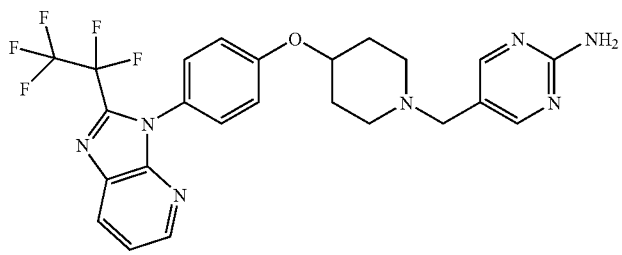 | 520 |
| 36A | 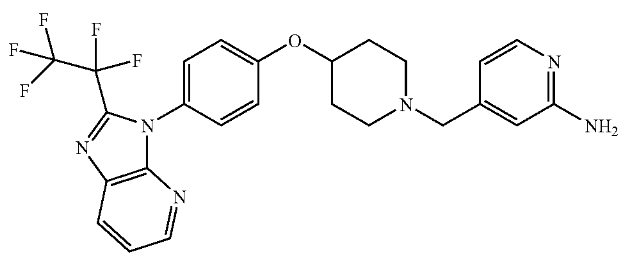 | 519 |
| 37A | 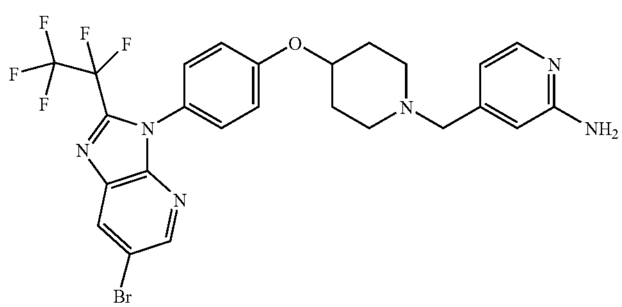 | 597 |

| Compound | Structure | (M + H) |
|---|---|---|
| 38A | 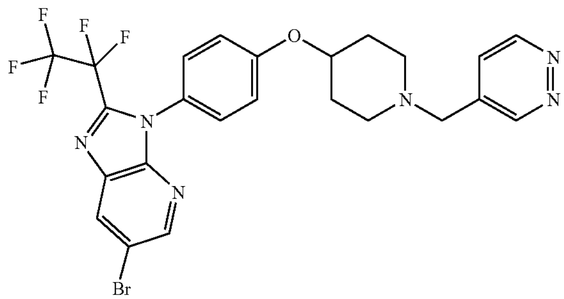 | 583 |
| 39A | 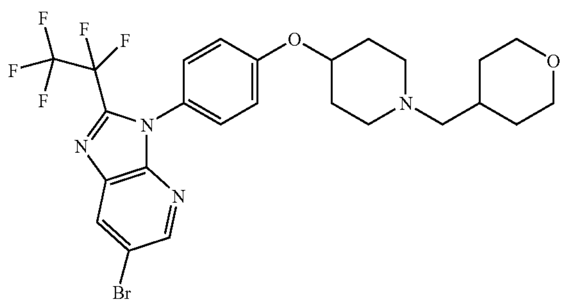 | 589 |
| 40A | 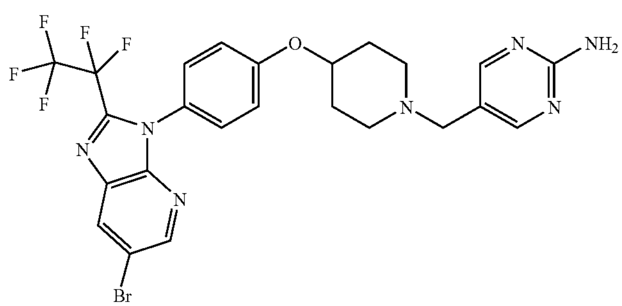 | 598 |
| 41A | 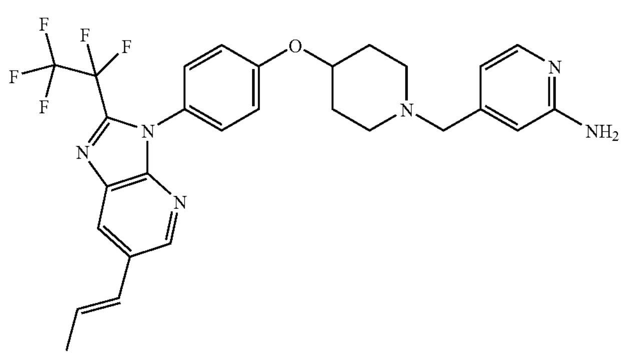 | 559 |

| Compound | Structure | (M + H) |
|---|---|---|
| 42A | 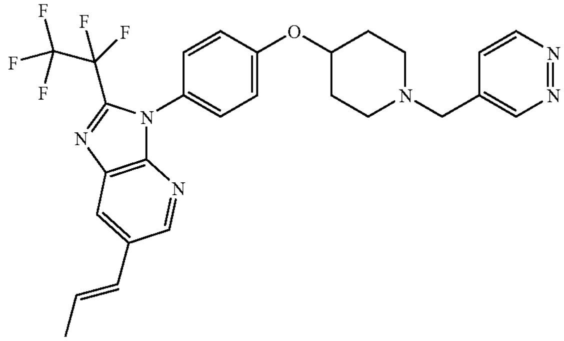 | 545 |
| 43A | 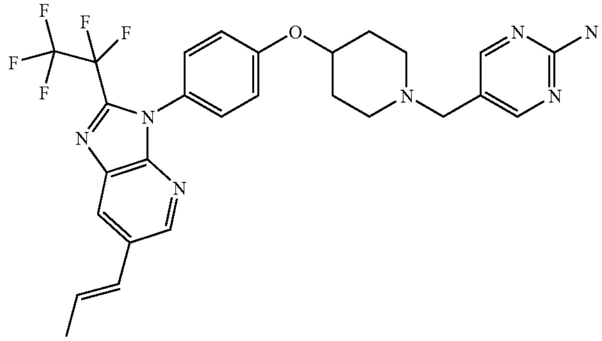 | 560 |
| 44A | 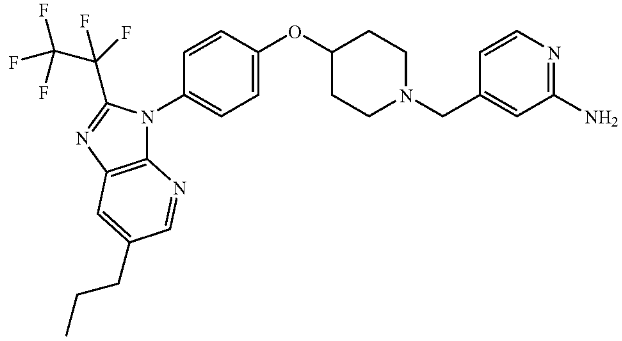 | 561 |
| 45A | 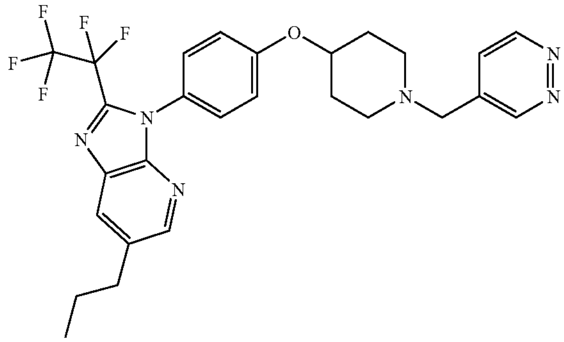 | 547 |

-continued

| Compound | Structure | (M + H) |
|---|---|---|
| 46A | 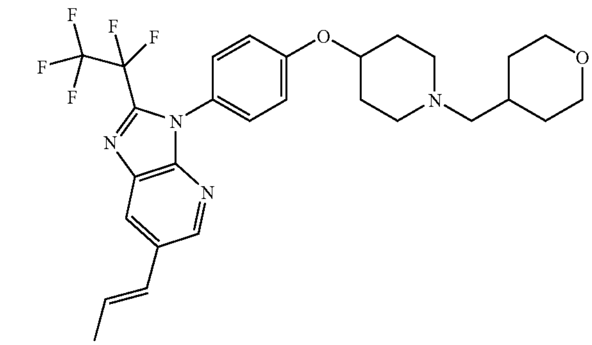 | 551 |
| 47A | 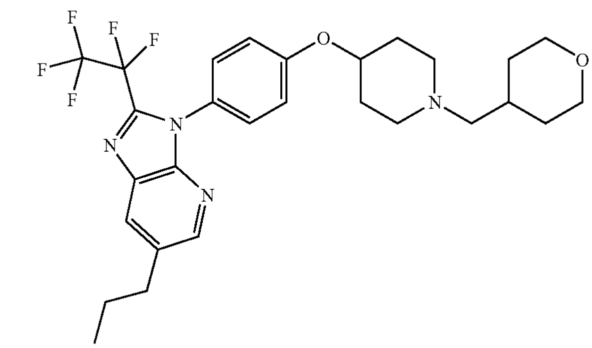 | 553 |
| 48A | 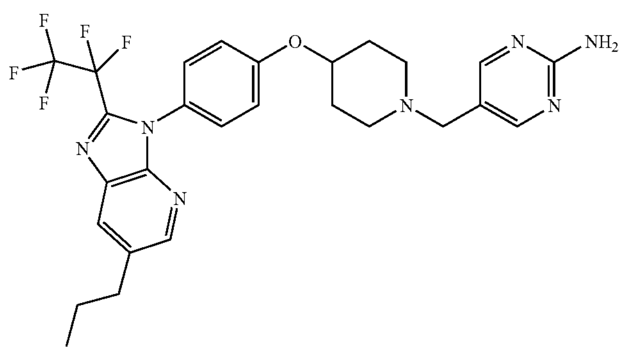 | 562 |
| 49A | 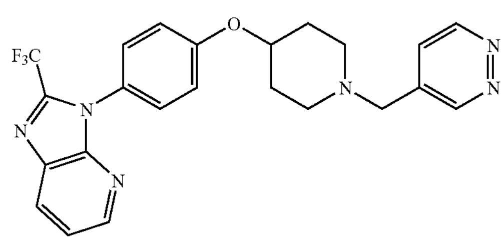 | 455 |
| 50A | 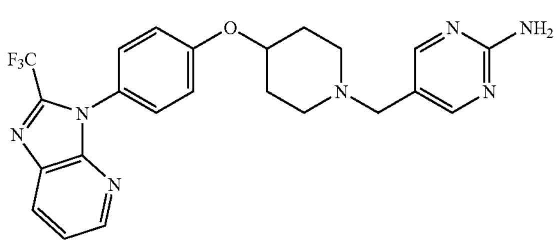 | 470 |

-continued

| Compound | Structure | (M + H) |
|---|---|---|
| 51A | 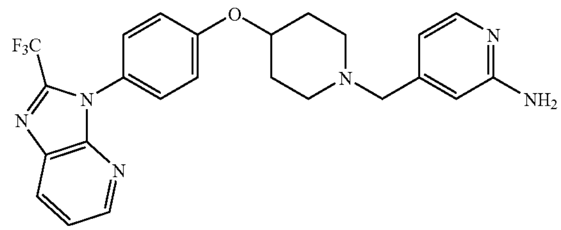 | 469 |
| 52A | 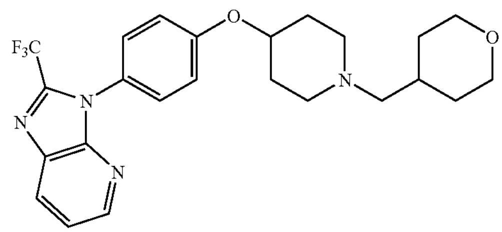 | 461 |
| 53A | 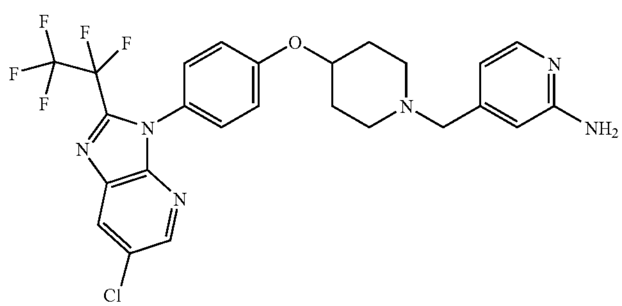 | 553 |
| 54A | 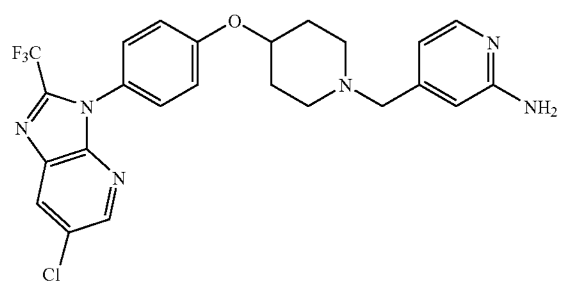 | 503 |
| 55A | 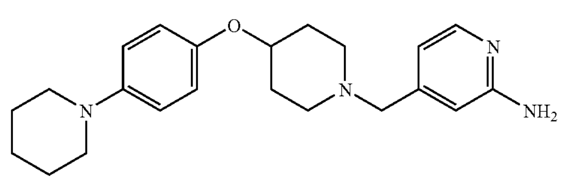 | 368 |
| 56A | 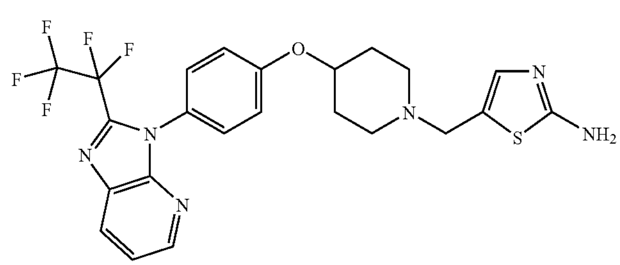 | 525 |

-continued

| Compound | Structure | (M + H) |
|---|---|---|
| 57A | 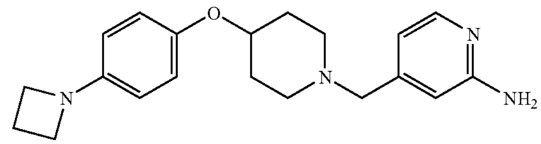 | 339 |
| 58A | 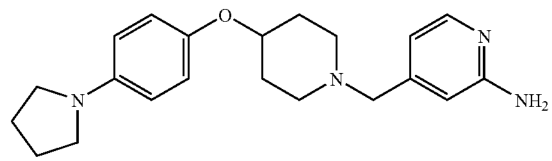 | 353 |
| 59A | 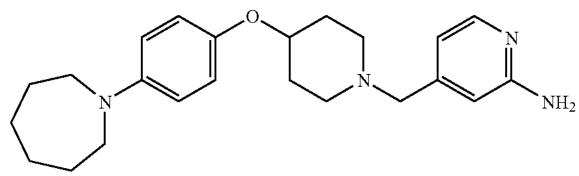 | 381 |
| 60A | 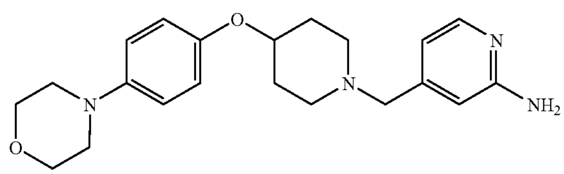 | 369 |
| 61A | 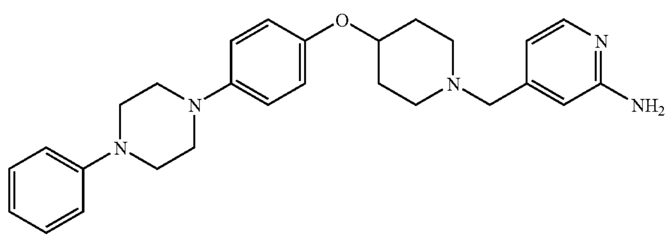 | 444 |
| 62A | 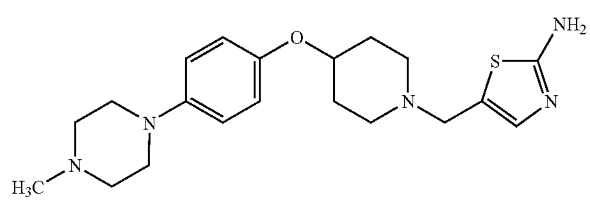 | 388 |
| 63A | 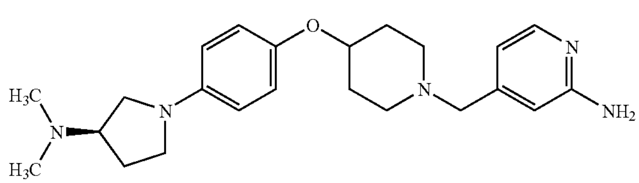 | 396 |
| 64A | 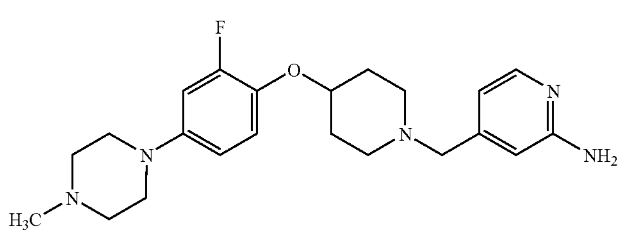 | 400 |

-continued

| Compound | Structure | (M + H) |
|---|---|---|
| 65A | 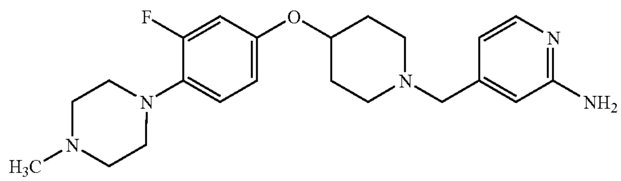 | 400 |
| 66A | 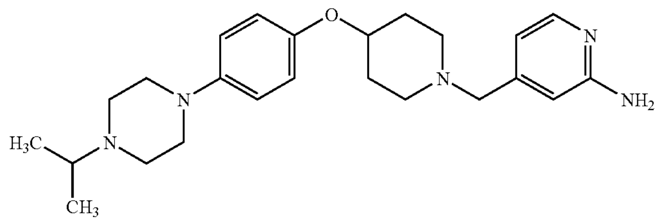 | 410 |
| 67A | 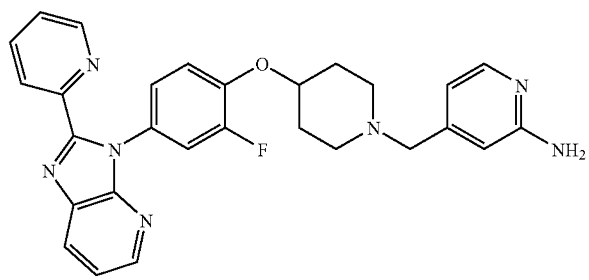 | 496 |
| 68A | 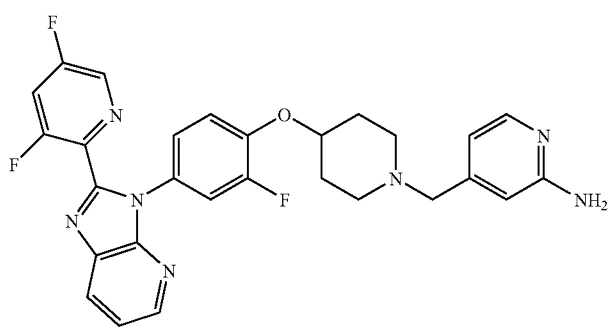 | 532 |
| 69A | 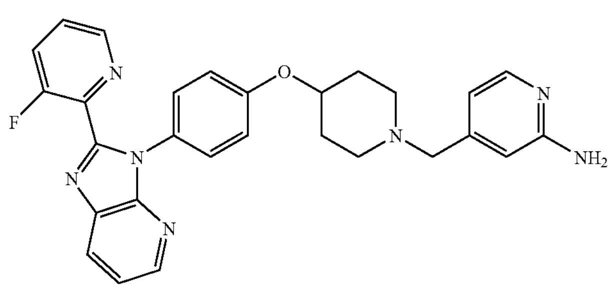 | 496 |

Example 23

Preparation of Compound 70A

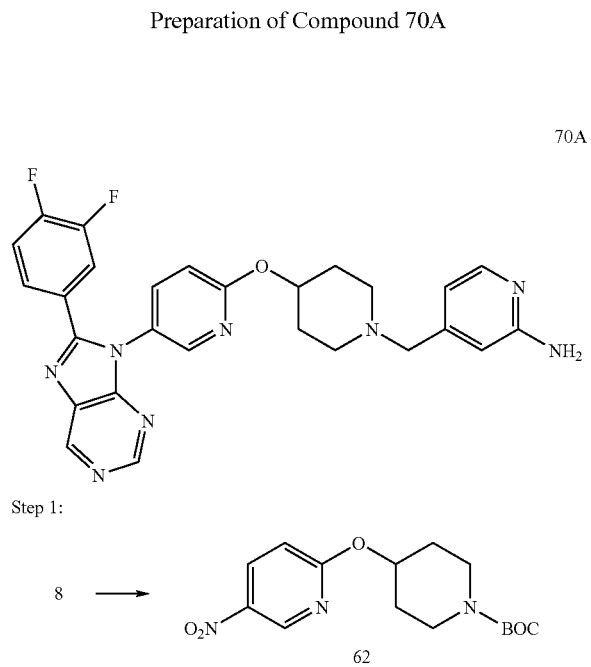

Step 1:

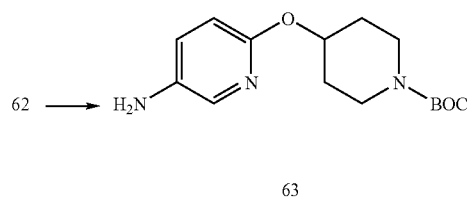

To a stirred mixture of potassium tert-butoxide (12.8 g, 115 mmol) and compound 8 (22.0 g, 110 mmol) in tert-butanol (150 mL), maintained at 50° C., was added 2-chloro-5-nitropyridine (19.0 g, 120 mmol) in one portion. After being heated at 50° C. for 16 h, the mixture was cooled to room temperature, diluted with $Et_2O$ (300 mL) and treated with water (200 mL). The aqueous phase was extracted with a second portion (200 m) of $Et_2O$. Combined extracts were washed with brine (200 mL), dried over anhydrous $MgSO_4$, filtered and concentrated under reduced pressure. The residue was purified using flash chromatography, eluting with DCM-EtOAc (~4.5:1) to provide 31.6 g of compound 62 as a light yellow solid.

Step 2:

62 ⟶ ![structure 63]

Raney nickel (10 g (W. R. Grace; 2800; slurry in water)) was added to a solution of compound 62 (31.5 g, 97.5 mmol) in THF (450 mL)-EtOH (150 mL), and the resultant mixture was hydrogenated at an initial pressure of 30 psi for 16 h. The spent catalyst was filtered off and washed with EtOH. Combined filtrate and washings were concentrated under vacuum to produce crude product 63 as a light cream-colored solid which was used without further treatment in the next step.

Step 3:

63 ⟶

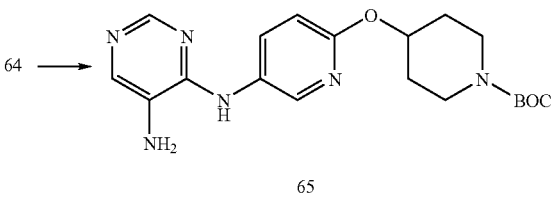

To a stirred, ice-cooled mixture of 4,6-dichloro-5-nitropyrimidine (4.00 g, 20.6 mmol) and $K_2CO_3$ (5.40 g, 39.2 mmol) in THF (30 mL) was added slowly a solution of 63 (5.75 g, 19.6 mmol) in THF (30 mL) over 20 min. The resultant mixture was stirred at 0° C. for 1 h. The reaction mixture was then treated with water (100 mL) and extracted with EtOAc (2×200 mL). Combined extracts were washed with brine (150 mL), dried over anhydrous $MgSO_4$, filtered and concentrated under vacuum. The residue was purified using flash chromatography, eluting with EtOAc-hexanes (1:3) to provide 5.82 g of compound 64 as a lemon-colored solid.

Step 4:

64 ⟶ ![structure 65]

To a mixture of 65 (5.80 g, 12.9 mmol) in EtOH (100 mL)-THF (100 mL) was added 20% palladium hydroxide-on-carbon catalyst (0.60 g), and the resultant mixture was hydrogenated for 16 h on a Parr shaker apparatus at an initial pressure of 40 psi. Catalyst was removed by filtration, and the filtrate was concentrated under vacuum to provide a black residue, which was purified using flash chromatography, eluting with DCM-2N methanolic ammonia (12:1) to provide 4.61 g of compound 65 as a gray solid.

Step 5:

65 ⟶

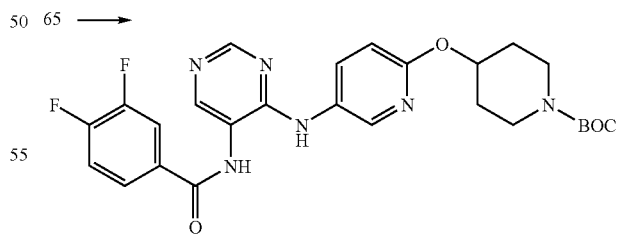

To a stirred solution of 66 (2.3 g, 5.80 mmol) and $Et_3N$ (1.61 ml, 11.6 mmol) in DCM (50 mL), maintained at 0° C. in an ice-water bath, was added slowly via dropping funnel 3,4-difluorobenzoyl chloride (0.877 ml, 6.97 mmol). The resultant mixture was stirred at 0° C. for 1 h, then at room temperature for 16 h. The reaction mixture was washed successively with 1N NaOH solution (25 mL) and brine (25 mL), and was then dried over anhydrous MgSO$_4$. The drying agent was filtered and the filtrate was concentrated under vacuum. The residue was flash chromatographed on silica gel, eluting with DCM-2N methanolic ammonia (20:1), to provide 2.21 g of compound 66 as a yellow solid.

Step 6:

Compound 66 was converted into the title compound using the methods set forth in Example 10, Steps 4-6. MH$^+$ 515

Example 24

Preparation of Compound 71A

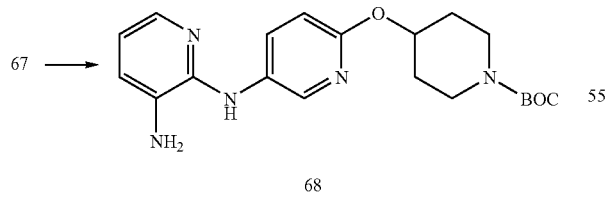

71A

Step 1:

63 ⟶

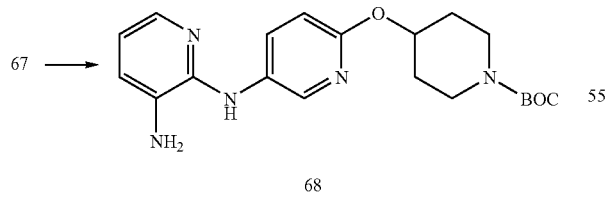

67

A stirred mixture of 2-chloro-3-nitropyridine (4.75 g, 30 mmol), K$_2$CO$_3$ (8.28 g, 60 mmol), KI (150 mg) and 67 (8.80 g, 30 mmol) was heated at 110° C. for 16 h. The reaction mixture was then cooled, treated with water (100 m) and extracted with EtOAc (1×200; 1×100 mL). Combined extracts were washed with brine (100 mL), dried over anhydrous MgSO$_4$, filtered and concentrated under vacuum. The residue was purified using flash chromatography, eluting with DCM-acetone (20:1) to provide 7.1 g of 67 as a bright orange solid.

Step 2:

67 ⟶

68

To a solution of nitro compound 67 (7.10 g, 17.1 mmol) in EtOH (50 mL)-THF (150 mL) was added Raney nickel catalyst (2.4 g (W. R. Grace; 2800; slurry in water)), and the resultant mixture was hydrogenated for 16 h on a Parr shaker apparatus at an initial pressure of 40 psi. Catalyst was removed by filtration, and the filtrate was concentrated under vacuum to provide 6.16 g of 68 as a light brown solid.

Step 3:

Compound 68 was converted into the title compound using the methods set forth in Example 10, Steps 3-6. MH$^+$ 520

Example 25

Preparation of Compound 72A

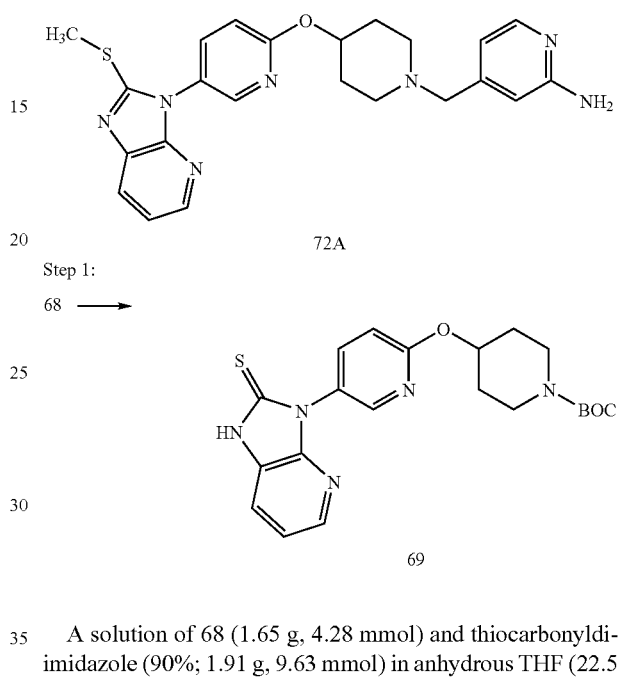

72A

Step 1:

68 ⟶

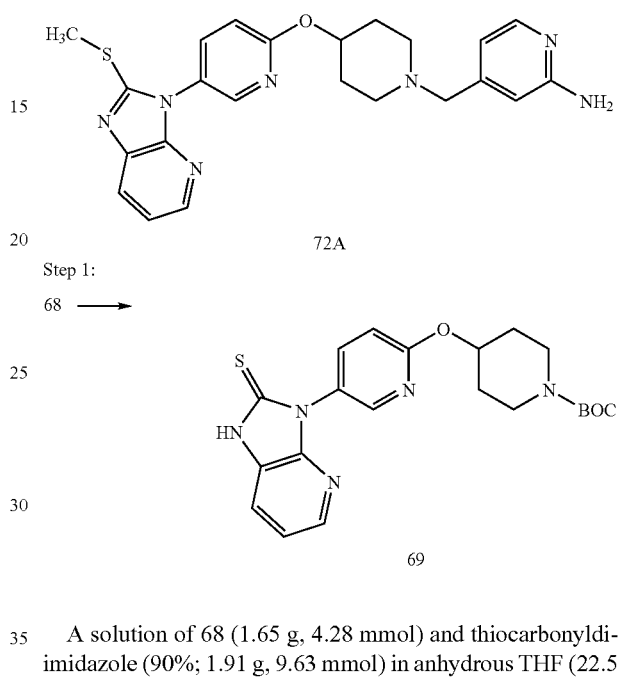

69

A solution of 68 (1.65 g, 4.28 mmol) and thiocarbonyldiimidazole (90%; 1.91 g, 9.63 mmol) in anhydrous THF (22.5 mL) was heated at ~72° C. in a sealed tube for 22 h. Solvent was removed under vacuum. The residue was triturated with EtOAc (~100 mL). Insoluble solid was filtered and purified using flash chromatography on silica gel, eluting with DCM-MeOH-ammonia (97:3:0.25), to provide 832 mg of 69 as a light gray solid.

Step 2:

69 ⟶

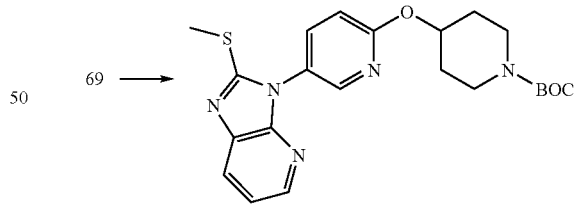

70

To a stirred mixture of 69 (500 mg, 1.17 mmol) and powdered K$_2$CO$_3$ (193 mg, 1.40 mmol) in DMF (14 mL) was added CH$_3$I (76.8 μl; 175 mg, 1.23 mmol). The resultant mixture was stirred at room temperature in a sealed tube until the starting thione was consumed, as judged by TLC (<16 h). The reaction mixture was filtered, and the filtrate was concentrated under vacuum. The residue was purified using flash chromatography on silica gel, eluting with DCM-MeOH-ammonia (98:2:0.25), to provide 489 mg of 70 as a foamy white solid.

Step 3:

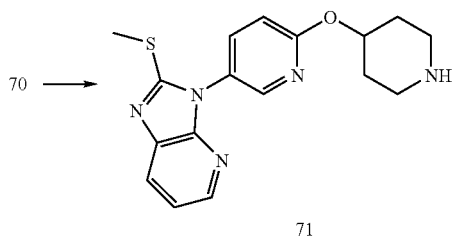

A solution of 71 (485 mg, 1.10 mmol) and TFA (813 μl; 1.25 g, 10.9 mmol) in DCM (8 mL) was stirred at room temperature for 23 h. The reaction mixture was concentrated under vacuum. The residue was partitioned between DCM (25 mL) and water (2 mL)-2M aqueous $Na_2CO_3$ (2 mL)-6N NaOH (2 mL). The aqueous layer was extracted with DCM (3×5 mL). Combined extracts were washed with brine (2 mL) and filtered through anhydrous $MgSO_4$. The filtrate was stripped of solvent under vacuum to provide 344 mg of 71 as an amorphous white solid, which was sufficiently pure for use in the next step.

Step 4:

Compound 71 was converted into the title compound using the methods set forth in Example 10, Steps 5-6. $MH^+$ 448

Example 26

Preparation of Compound 73A

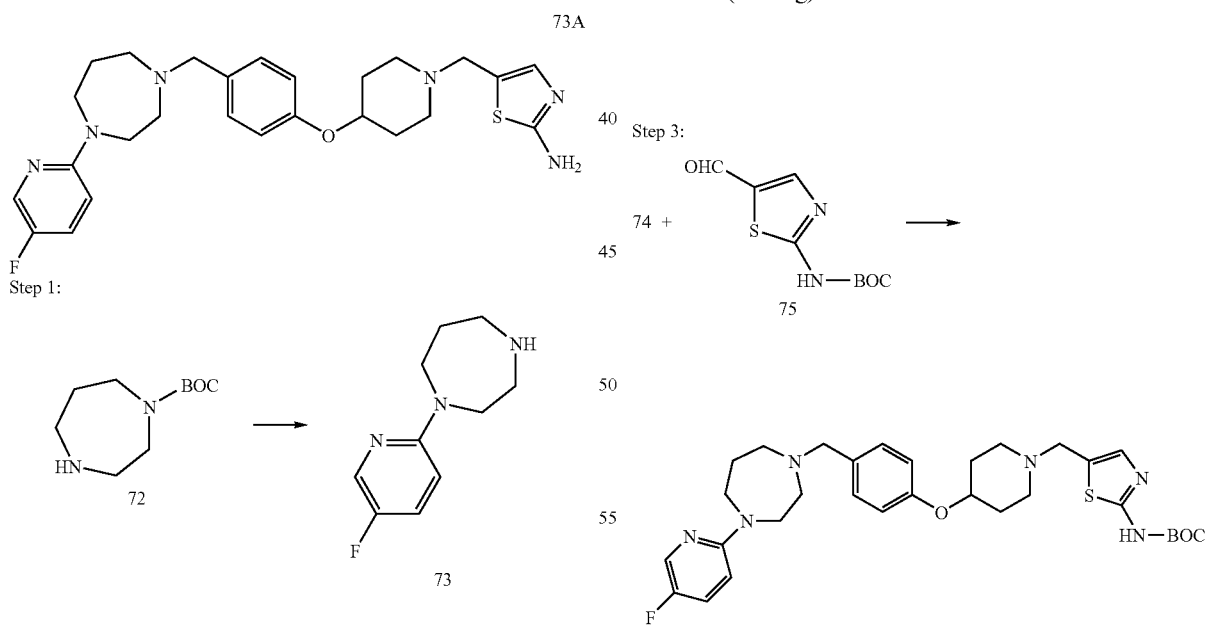

To a solution of 2-bromo-5-fluoropyridine (500 mg, 2.84 mmol) and t-butyl-1,4-diazepine-1-carboxylate 72 (1.7 g, 8.52 mmol) in DMF (5 mL) was added anhydrous $K_2CO_3$ powder (3 g). The mixture was stirred at 120° C. for 12 h under $N_2$. The mixture was filtered and concentrated to remove DMF. Flash chromatography (EtOAc/Hexanes, 1:4) afforded a yellow oil as the coupled product. The oil was stirred in TFA (5 mL) and DCM (5 mL) for 30 min, then concentrated in vacuo. The residue was dissolved in DCM. 1N NaOH was added and the mixture was stirred for 10 min. The DCM layer was separated, dried over $MgSO_4$, filtered and concentrated to give the amine 73 (260 mg).

Step 2:

73 + 46 ⟶

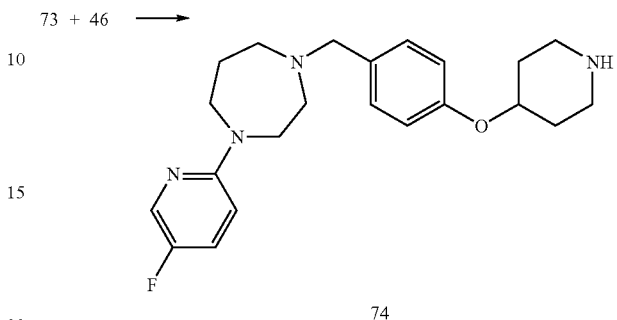

To a solution of 73 (250 mg, 1.28 mmol) and 46 (586 mg, 1.92 mmol) in DCM (5 mL) was added HOAc (0.1 mL). The mixture was stirred for 10 min, then $NaBH(OAc)_3$ (426 mg, 1.92 mmol) was added. The mixture was stirred at room temperature for 12 h. The mixture was diluted with DCM, washed with 1N NaOH, brine, dried over $MgSO_4$, filtered and concentrated in vacuo. Flash chromatography (MeOH/DCM, 1:10) afforded a yellow oil. The oil was stirred in TFA (5 mL) and DCM (5 mL) for 30 min, then concentrated in vacuo. The residue was dissolved in DCM, 1N NaOH was added and the mixture was stirred for 10 min. The DCM layer was separated, dried over $MgSO_4$, filtered and concentrated to give the amine 74 (170 mg).

Step 3:

Compound 75 was prepared from commercially available 2-aminothiazole-5-carbaldehyde by a standard procedure ($(BOC)_2O$, DCM, room temperature).

Using the procedure of Example 10, Step 5, 76 was prepared from 74 and 75.

Step 4:

Compound 76 was converted into the title compound using the procedure of Example 10, Step 6. MH+ 497

Example 27

Preparation of Compound 74A

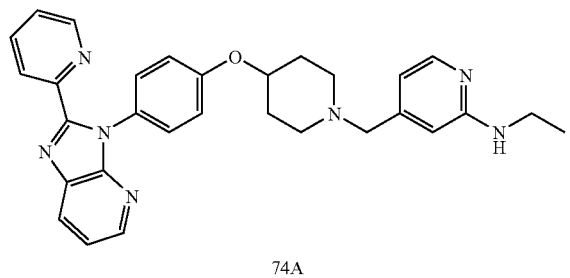

74A

Step 1

14 ⟶

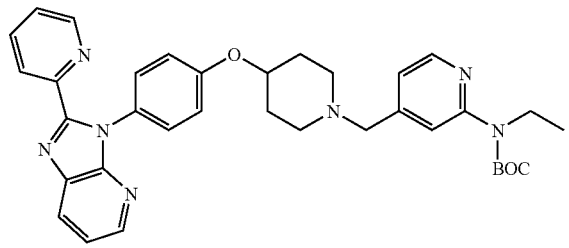

77

NaH (64 mg, 1.6 mmol) was added to a mixture of compound 14 (465 mg, 0.8 mmol, was prepared using the method described in steps 1-6 of example 4) in anhydrous DMF (5 mL). The resulting reaction was allowed to stir at 45° C. for 30 min, then iodoethane (78 μl, 0.96 mmol) was added, and the reaction was heated to 60° C. and allowed to stir at this temperature for 16 h. The reaction mixture was cooled to room temperature, then EtOAc (30 mL) and water (30 mL) were added, and the aqueous phase was extracted again with EtOAc (20 mL). The combined organic phases were washed with brine (20 mL), dried over anhydrous MgSO$_4$, and concentrated in vacuo. The resulting residue was purified using flash column chromatography on silica gel, eluting with CH$_2$Cl$_2$-MeOH (25:1) to provide compound 77 as a beige solid (266 mg).

Step 2

Compound 77 was converted into the title compound using the method set forth in Example 4, step 8. MH+ 506.

Example 28

Preparation of Compound 75A

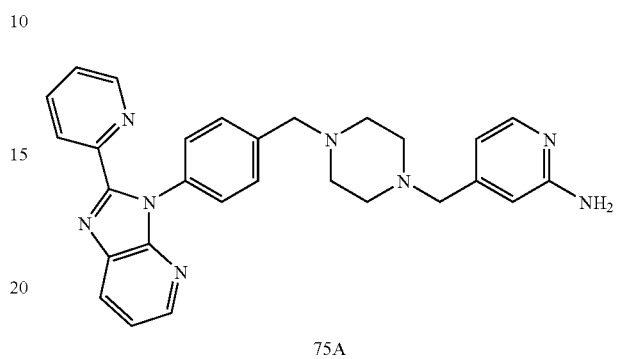

75A

Step 1

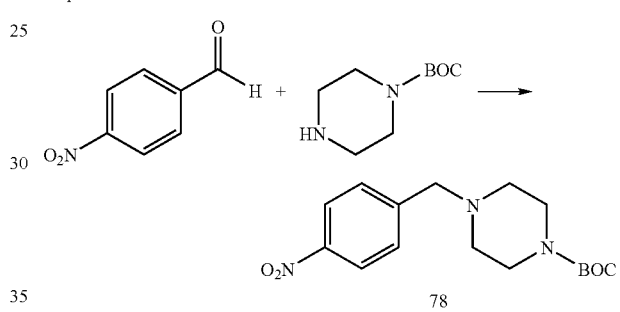

78

A mixture of 4-nitro benzaldehyde (20.0 g, 129 mmol) and 1-Boc piperazine (20.0 g, 107 mmol) in DCM (500 mL) was allowed to stir at room temperature for 1.5 h, then Na(OAc)$_3$BH (45.3 g, 214 mmol) was added and the resultant reaction was allowed to stir stirring at room temperature for an additional 3 h. The reaction mixture was then sequentially washed with 1N NaOH (250 mL) and brine (250 mL), dried over anhydrous MgSO$_4$, and concentrated in vacuo to provide compound 78 as a light orange solid (35.1 g).

Step 2

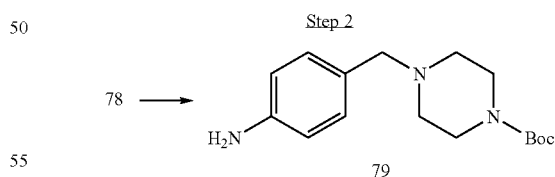

79

To a solution of compound 78 (35 g, 110 mmol) in a mixture of THF (300 mL)-EtOH (100 mL) was added 50% Raney Nickel (12 g, aqueous slurry), and the mixture was placed on a Parr Shaker and hydrogenated at P$_0$=40 Psi for 16 h. The spent catalyst was filtered off, and the filtrate was concentrated in vacuo. The resultant residue was purified using flash column chromatography on silica gel, eluting with CH$_2$Cl$_2$-MeOH (25:1) to provide compound 79 as a light yellow solid (24.1 g).

Step 3

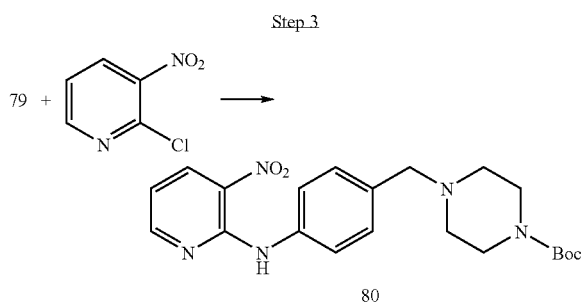

To a mixture of 2-chloro-3-nitropyridine (6.3 g, 40 mmol) in toluene (100 mL) was added compound 79 (11.6 g, 40 mmol), followed by solid $K_2CO_3$ (11 g, 80 mmol), and the resulting reaction was heated to 110° C. and allowed to stir at this temperature for 16 h. BINAP (500 mg, 2% mol) and $Pd(OAc)_2$ (180 mg, 2% mol) were then added to the reaction mixture and the reaction was allowed to stir for an additional 4 h at 110° C. The reaction mixture was cooled to room temperature, then EtOAc (250 mL) and water (200 mL) were added, and the resulting solution was filtered through Celite to remove any insoluble material. The filtrate was separated and the aqueous phase was extracted with EtOAc (200 mL). The combined organic phases were washed with brine (300 mL), dried over anhydrous $MgSO_4$, and concentrated in vacuo. The resulting residue was purified using flash column chromatography on silica gel, eluting with EtOAc-Hexane (1:1) to provide compound 80 as a red solid (24.1 g).

Step 4

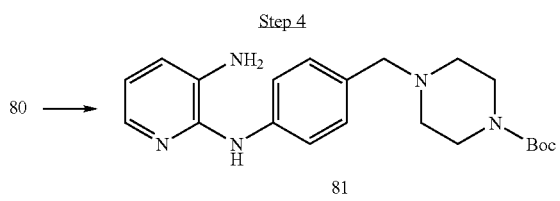

Compound 80 (15.8 g, 38 mmol) was converted to compound 81 using the method set forth in step 2. Compound 81 was a light grey solid (11.8 g).

Step 5

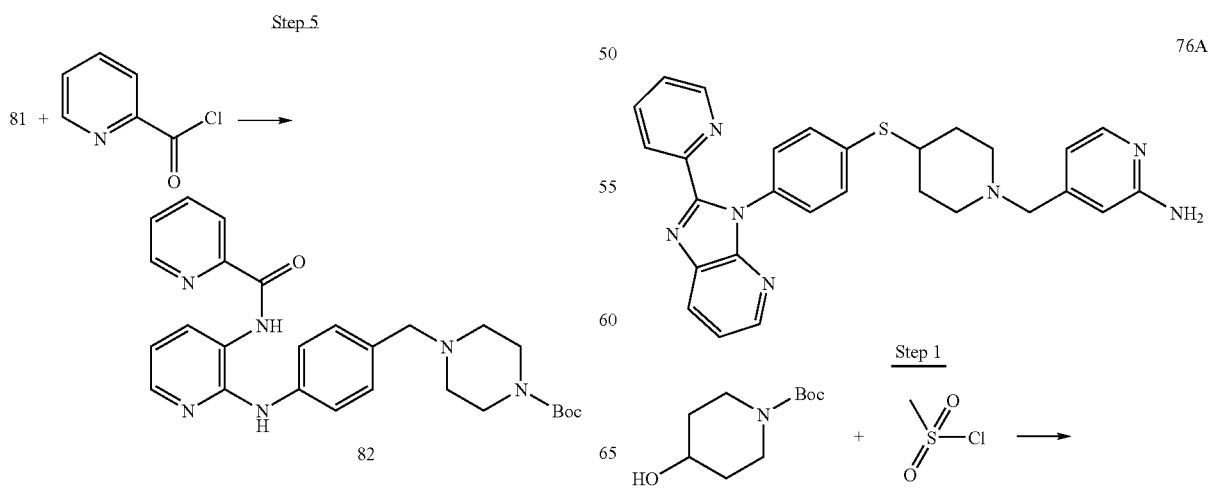

A solution of compound 81 (3.83 g, 10 mmol) in DCM (60 mL) and $Et_3N$ (4 mL) was cooled to 0° C., then 2-picolinoyl chloride (2.14 g, 12 mmol) was added, and the resulting reaction was allowed to stir at 0° C. for 1 h, then at room temperature for 16 h. The reaction mixture was washed sequentially with 1N NaOH (40 mL), and brine (40 mL), dried over anhydrous $MgSO_4$, and concentrated in vacuo. The resulting residue was purified using flash column chromatography on silica gel, eluting with $CH_2Cl_2$-MeOH (50:1) to provide compound 82 as yellow foam (4.41 g).

Step 6

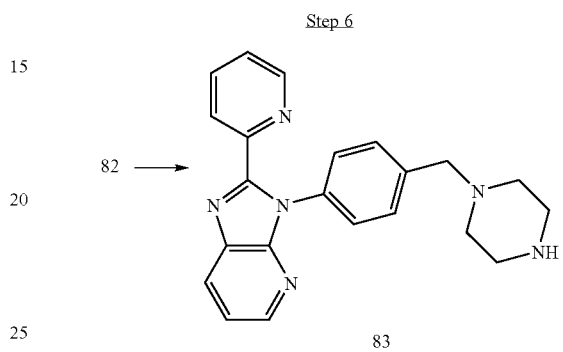

A mixture of compound 82 (2.20 g, 4.5 mmol) in ethylene glycol (15 mL) was heated to 170° C. and allowed to stir at this temperature for 16 h. EtOAc (60 mL) and water (30 mL) were added to the cooled mixture and the aqueous layer was extracted once more with EtOAc (60 mL). The combined organic phases were washed with brine (30 mL), dried over anhydrous $MgSO_4$, and concentrated in vacuo. The resulting residue was purified using flash column chromatography on silica gel, eluting with $CH_2Cl_2$-MeOH (13:1) to provide compound 83 as a light yellow solid (0.41 g).

Step 7

Compound 83 was converted into the title compound using the methods set forth in Example 4, steps 6-7. $MH^+$ 477

Example 29

Preparation of Compound 76A

-continued

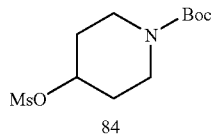
84

A solution of 4-hydroxy-N-Boc piperidine (2.01 g, 10 mmol) in DCM (30 mL) and Et₃N (2.80 mL, 20 mmol) was cooled to 0° C., and methanesulfonyl chloride was slowly added. The reaction was allowed to stir at 0° C. for 2 h and was then concentrated in vacuo. The resulting residue was purified using flash column chromatography on silica gel, eluting with EtOAc-Hexane (1:1) to provide compound 84 as a white solid (2.76 g).

Step 2

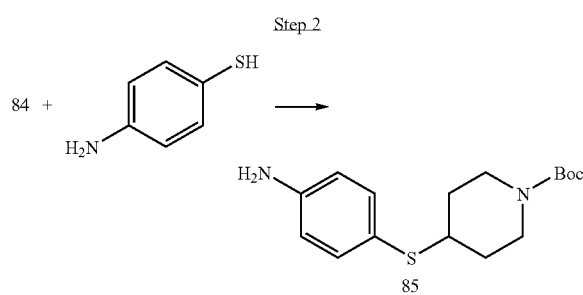
85

NaH (9.2 g, 230 mmol) was added portionwise over a period of 30 min to a solution of compound 84 (43 g, 153 mmol) in DMF (400 mL). The reaction was allowed to stir at room temperature for 2 h, then 4-amino benzene thiol (23 g, 184 mmol) was added. The resulting reaction was allowed to stir at room temperature for 16 h and was then poured into water (400 mL), extracted with EtOAc (500 mL×2), and the combined organics were washed with brine (500 mL), dried over anhydrous MgSO₄, and concentrated in vacuo. The resulting residue was purified using flash column chromatography on silica gel, eluting with EtOAc-Hexane (3:4) to provide compound 85 as a light yellow solid (38.8 g).

Step 3

Compound 85 was converted to the title compound using the procedures from steps 3-6 of Example 1337450, followed by steps 6-7 of Example 4. MH⁺ 494

Example 30

Preparation of Compound 77A

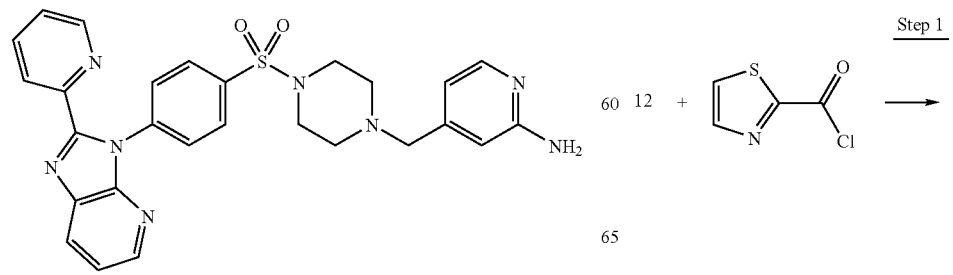
77A

-continued

Step 1

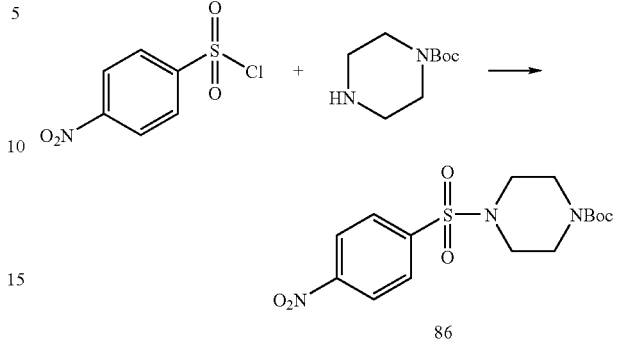
86

A solution of N-Boc piperazine (14.4 g, 77.4 mmol) in DCM (300 mL) and Et₃N (21.6 mL, 155 mmol) was cooled to 0° C. and p-Nitrobenzene sulfonyl chloride (20.5 g, 93 mmol) was added portionwise to the cooled solution. The resulting reaction, was allowed to stir at 0° C. for 1 h, then at room temperature for 16 h. The reaction mixture was washed sequentially with 1N NaOH (50 mL) and brine (50 mL), and the organic phase was dried over anhydrous MgSO₄, and concentrated in vacuo. The resulting residue was purified using flash column chromatography on silica gel, eluting with EtOAc-Hexane (1:1) to provide compound 86 as a light yellow solid (28.0 g).

Step 2

Compound 86 was converted to the title compound using the methods set forth in steps 2-6 of Example 75, followed by steps 6-7 of Example 4. MH⁺ 527

Example 31

Preparation of Compound 78A

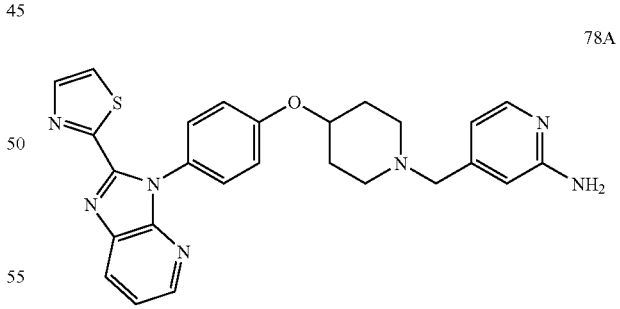
78A

Step 1

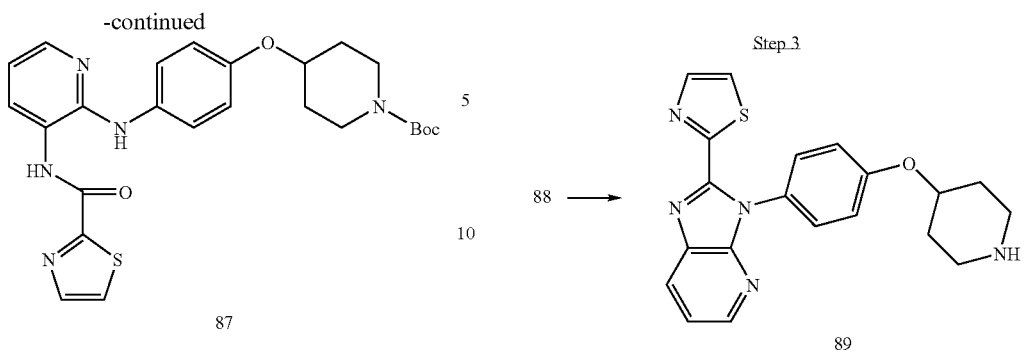

87

A solution of compound 12 (2.40 g, 6.2 mmol, prepared as described in steps 1-4 of Example 4) in DCM (60 mL) and Et$_3$N (1.3 mL, 9.3 mmol) was cooled to 0° C. and, 1,3-thiazole-2-carbonyl chloride (1.00 g, 6.8 mmol) was added to the cooled solution. The resulting reaction was allowed to stir at 0° C. for 1 h, then at room temperature for 16 h. The reaction mixture was washed sequentially with 1N NaOH (30 mL), and brine (30 mL), then the organic phase was dried over anhydrous MgSO$_4$, and concentrated in vacuo. The resulting residue was purified using flash column chromatography on silica gel, eluting with DCM-Acetone (12:1) to provide compound 87 as a tan solid (2.95 g).

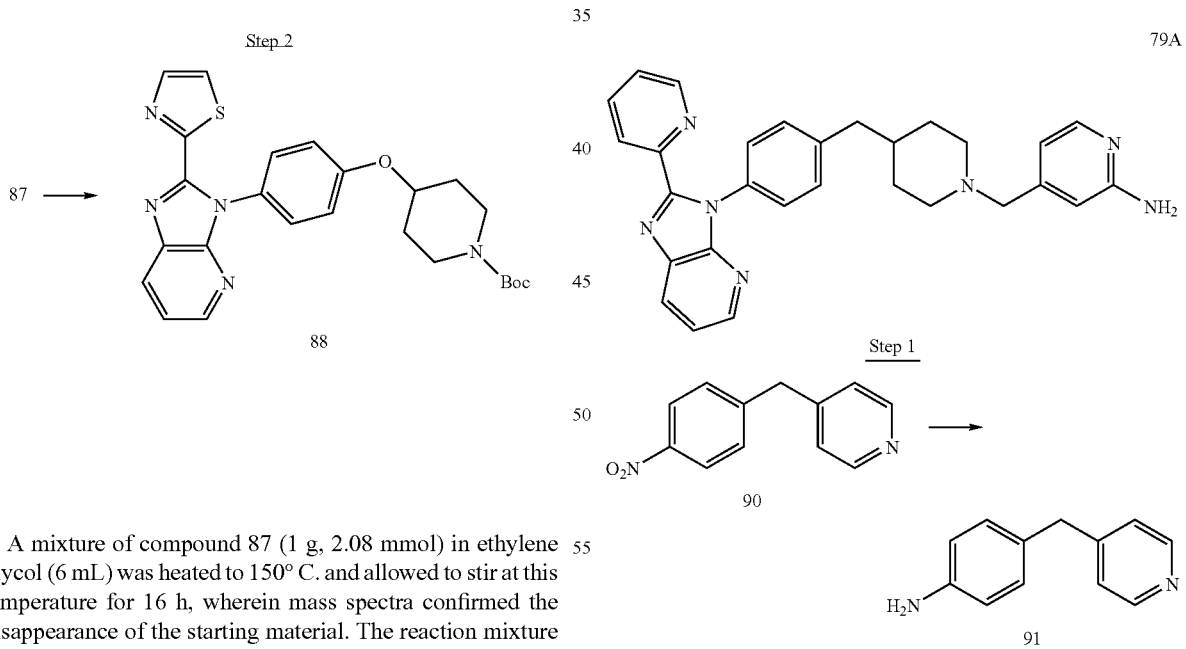

A mixture of compound 87 (1 g, 2.08 mmol) in ethylene glycol (6 mL) was heated to 150° C. and allowed to stir at this temperature for 16 h, wherein mass spectra confirmed the disappearance of the starting material. The reaction mixture was cooled to room temperature, then diluted with EtOAc (60 mL) and water (60 mL). The aqueous layer was separated, and the extracted once more with EtOAc (30 mL). The combined organic layers were dried over anhydrous MgSO$_4$, concentrated in vacuo, and the residue was purified using flash column chromatography on silica gel, eluting with DCM-acetone (15:1) to provide compound 88 as a tan solid (0.362 g).

Trifluoroacetic acid (1 mL) was added to a solution of compound 88 (360 mg, 0.755 mmol) in DCM (4 mL), and the reaction was allowed to stir at room temperature for 16 h. The reaction mixture was then diluted with DCM (10 mL), basified using 50% NH$_4$OH (v/v, 6 mL), then the aqueous was extracted once more with DCM (10 mL). The combined organics were dried over anhydrous MgSO$_4$, and concentrated in vacuo to provide compound 89 as a light pink solid (0.265 g).

Step 4

Compound 89 was converted to the title compound using the methods set forth in steps 6-7 of Example 4. MH$^+$ 484

Example 32

Preparation of Compound 79A

To a solution of compound 90 (25 g, 117 mmol) in a mixture of THF (300 mL)-EtOH (100 mL) was added 50% Raney Nickel (5 g, aqueous slurry), and the mixture was placed on a Parr Shaker and hydrogenated at P$_0$=40 Psi for 16 h. The spent catalyst was filtered off, and the filtrate was passed through Celite, then concentrated in vacuo to provide compound 91 as a light yellow solid (22.3 g).

Step 2

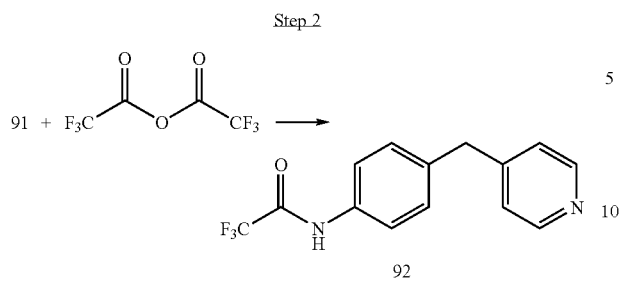

A solution of compound 91 (22 g, 120 mmol) in DCM (500 mL) and Et₃N (10.5 mL, 143 mmol) was cooled to 0° C., then trifluoroacetic anhydride was added to the cooled solution via an addition funnel over a period of 20 min. The resultant reaction was allowed to stir at 0° C. for 1 h, then at room temperature for 2 h. The reaction mixture was then concentrated in vacuo and the resulting residue was purified using flash column chromatography on silica gel, eluting with DCM-acetone (9:1) to provide compound 92 as a yellow solid (25.8 g).

Step 3

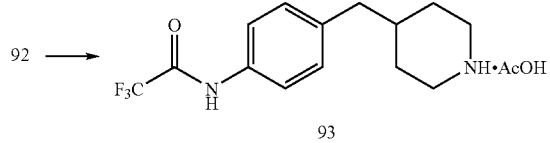

To a mixture of compound 92 (25 g, 89.2 mmol) in acetic acid (180 mL) was added PtO₂ (3 g), and the reaction vessel was place on a Parr shaker and hydrogenated at $P_0$=40 Psi for 16 h. The reaction mixture was then filtered to remove catalyst and the filtrate was washed with MeOH (100 mL), then passed through a pad of Celite and concentrated in vacuo. The resulting residue was dissolved in MeOH (100 mL), and the resulting solution was poured into Et₂O (600 mL). The white precipitate formed and was filtered, washed with Et₂O, and dried to provide compound 93 as a white solid (30.0 g).

Step 4

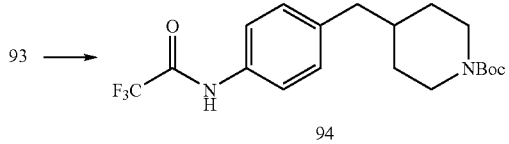

A mixture of compound 93 (30.0 g, 86.7 mmol) in DCM (500 mL) was cooled to 0° C., then Et₃N (18 mL, 130 mmol) was added slowly. To the resulting solution was added a solution of Boc₂O (20.0 g, 95.4 mmol) in DCM (100 mL) via a dropping funnel over a period of 10 min. The resulting reaction was allowed to stir at 0° C. for 2 h, then NaOH (2N, 50 mL) was added to the reaction, and the resulting reaction was allowed to stir at room temperature for 1 h. The reaction mixture was separated and the organic layer was washed with brine (100 mL), dried over anhydrous MgSO₄, and concentrated in vacuo. The resulting residue was purified using flash column chromatography on silica gel, eluting with EtOAc-Hexane (1:4) to provide compound 94 as a white solid (30.1 g).

Step 5

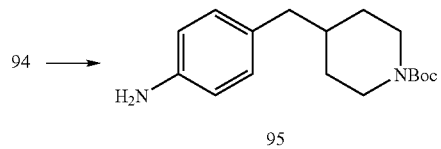

K₂CO₃ (2N aqueous solution, 150 mL) was added to a solution of compound 94 (30.0 g, 78 mmol) in MeOH (300 mL), and the reaction was allowed to stir at room temperature for 16 h. The reaction mixture was concentrated in vacuo and the resulting residue was extracted with DCM (300 mL×2). The combined organics were dried over anhydrous MgSO₄, and concentrated in vacuo to provide compound 95 as light brown syrup which solidified into a tan solid upon standing (24.6 g).

Step 6

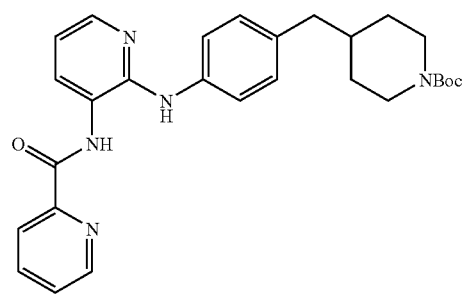

Compound 96 was prepared from compound 95 and 2-chloro-3-nitropyridine using the method set forth in Example 75, step 3.

Step 7

Compound 96 was converted to the title compound using the methods set forth in steps 1-3 of Example 78, followed by steps 6-7 of Example 4. MH⁺ 476

Example 33

Preparation of Compound 80A

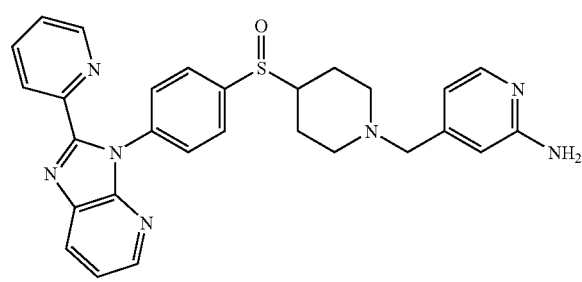

-continued

Step 1

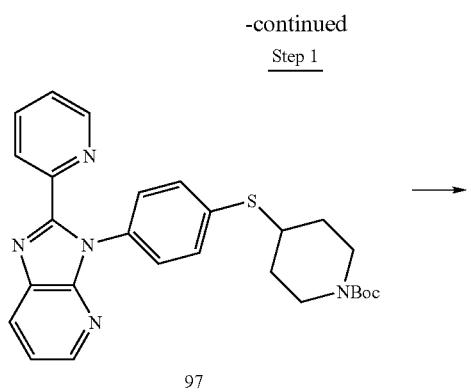

97

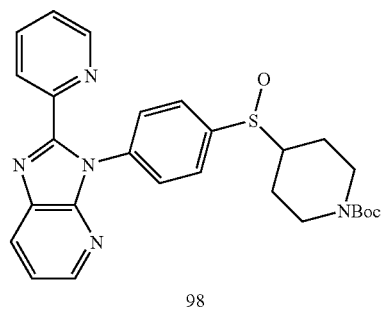

98

A solution of compound 97 (250 mg, 0.513 mmol, prepared using the method set forth in Example 75) in DCM was chilled in an isopropanol-dry ice bath, and to the cooled solution was added m-chloroperbenzoic Acid (114 mg, 0.513 mmol). The reaction was allowed to stir in the cooling bath for 3 h and the reaction mixture was then washed sequentially with 1 N NaOH (6 mL) and brine (6 mL), dried over anhydrous $MgSO_4$, and concentrated in vacuo. The resulting residue was purified using flash column chromatography on silica gel, eluting with DCM-MeOH (1:45) to provide compound 98 as a white foam (236 mg).

Step 2

Compound 98 was converted to the title compound using the methods set forth in step 7 of Example 78, followed by steps 6-7 of Example 4. $MH^+$ 510

Example 34

Preparation of Compound 81A and 81B

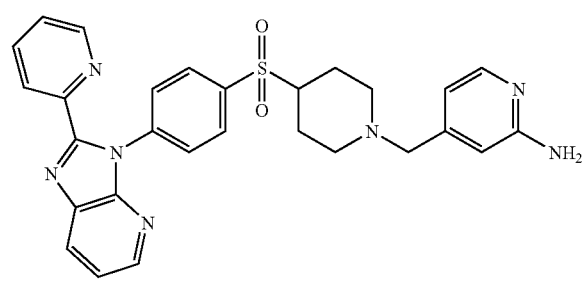

81A

-continued

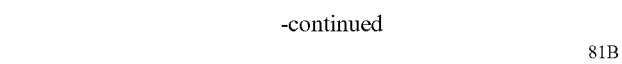

81B

Step 1

97 →

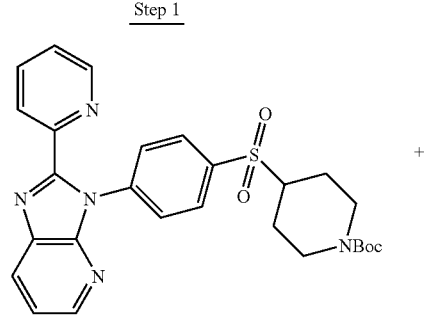

98

99

A solution of compound 97 (250 mg, 0.513 mmol, prepared using the method set forth in Example 1337450) in DCM was chilled in an isopropanol-dry ice bath, and to the cooled solution was added m-chloroperbenzoic Acid (114 mg, 0.513 mmol). The reaction was allowed to stir in the cooling bath for 3 h and the reaction mixture was then washed sequentially with 1 N NaOH (6 mL) and brine (6 mL), dried over anhydrous $MgSO_4$, and concentrated in vacuo. The resulting residue was purified using flash column chromatography on silica gel, eluting with DCM-MeOH (1:45) to provide compound 98 as a light yellow solid (85 mg) and 99 as a light yellow foam (131 mg).

Step 2

Compounds 98 and 99 were converted to the title compounds 81A and 81B, respectively, using the methods set forth in steps 6-7 of Example 4.

Example 35

Preparation of Compound 82A

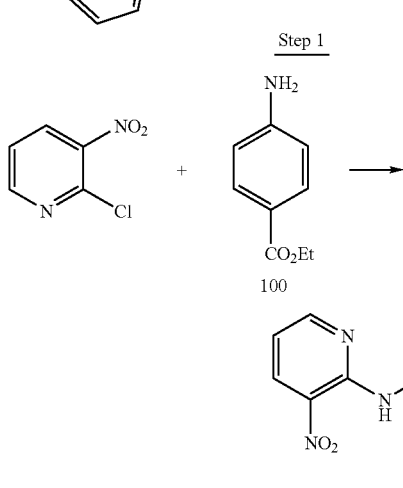

82A

Step 1

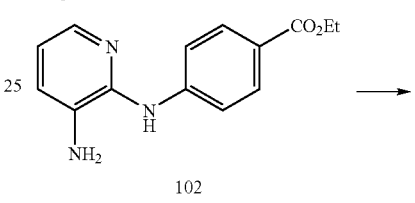

To a solution of 2-chloro-3-nitropyridine (4.75 g, 30 mmol) and compound 100 (4.95 g, 30 mmol) in toluene (150 mL) was added $K_2CO_3$ (8.28 g, 60 mmol), NaI (0.15 g, 1 mmol), BINAP (0.37 g, 0.6 mmol), and Pd(OAc)$_2$ (0.14 g, 0.6 mmol). The resulting reaction was heated to 110° C. and allowed to stir at this temperature for 20 h. The reaction mixture was then cooled to room temperature, extracted with EtOAc and the organics were washed with water, dried over $Na_2SO_4$, concentrated in vacuo. The resulting residue was purified using flash chromatography using 10% of EtOAc/hexane to provide compound 101 as orange solid. Yield: 6.5 g, 75%.

Step 2

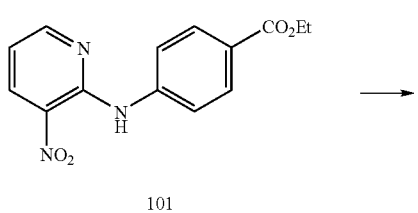

101

-continued

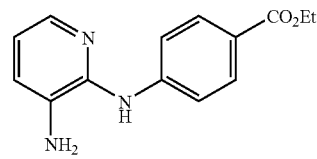

102

To a solution of compound 101 (5.5 g, 19.1 mmol) in EtOH (100 mL) (in a 500 mL hydrogenation bottle) was added Ra—Ni (1.9 g). The mixture was hydrogenated at room temperature at 50 psi under $H_2$ for 20 h. The reaction mixture was then filtered through celite, and the filtrate concentrated in vacuo to provide compound 102. Yield: 4.7 g, 95%.

Step 3

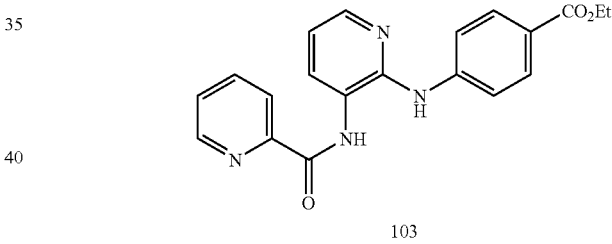

102

103

To a solution of compound 102 (2.2 g, 8.6 mmol) and $Et_3N$ (3.6 mL, 25.8 mmol) in $CH_2Cl_2$ (40 mL) was slowly added picolinoyl chloride hydrochloride (2.0 g, 10.3 mmol). The reaction was allowed to stir at room temperature for 1.5 h, after which time the reaction mixture was extracted with $CH_2Cl_2$ and water. The combined organic layers were dried over $Na_2SO_4$, concentrated in vacuo, and purified using flash chromatography to provide compound 103. Yield: 2.6 g, 84%.

Step 4

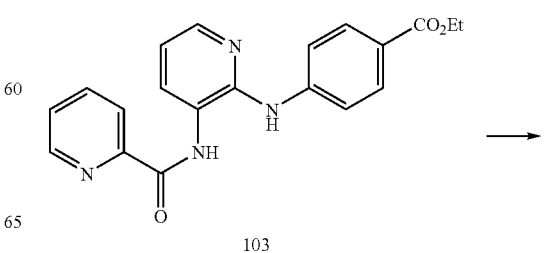

103

-continued

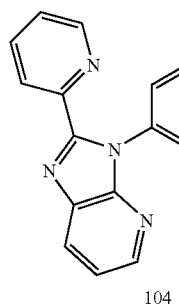
104

A solution of compound 103 (2.6 g, 7.2 mmol) in acetic acid (20 mL) was heated to 120° C. under $N_2$ and allowed to remain at this temperature for 20 h. The reaction mixture was then cooled to room temperature and concentrated in vacuo to provide compound 104. Yield: 2.5 g, 99%.

Step 5

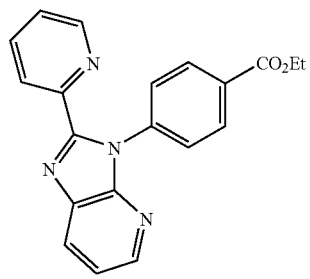
104

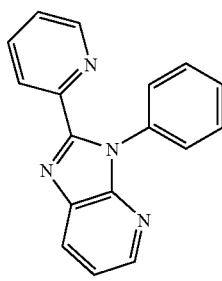
105

To a suspension of compound 104 (1.0 g, 2.9 mmol) in a 1:1 mixture of MeOH/water (20 mL) was added $LiOH \cdot H_2O$ (1.9 g, 4.4 mmol). The reaction mixture was heated to 60° C. and allowed to stir at this temperature for 1.5 h, after which time the reaction was concentrated in vacuo to provide compound 105. Yield: 1.0 g, 100%.

Step 6

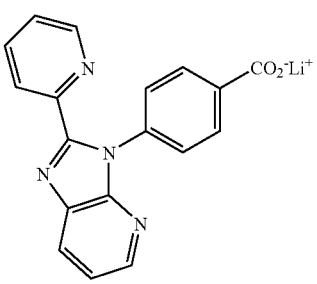
105

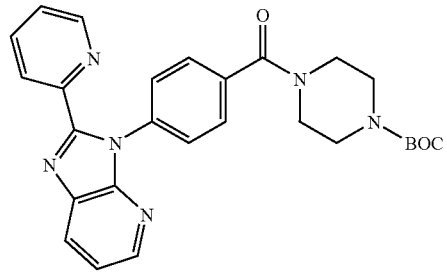
106

To a solution of compound 105 (1.0 g, 3.1 mmol) and 1-Boc-piperazine (0.58 g, 3.1 mmol) in DMF (10 mL) at 25° C., was added DEC (0.89 g, 4.7 mmol) and HOBT (0.63 g, 4.7 mmol). The reaction was heated to 60° C. and allowed to stir at this temperature for 20 h, after which time 5% of NaOH aqueous solution was added. The resulting solution was extracted with $CH_2Cl_2$, washed sequentially with water (3×) and brine, dried over $Na_2SO_4$, then filtered. The filtrate was concentrated in vacuo and purified using flash chromatography to provide compound 106. Yield: 1.3 g, 87%.

Step 7

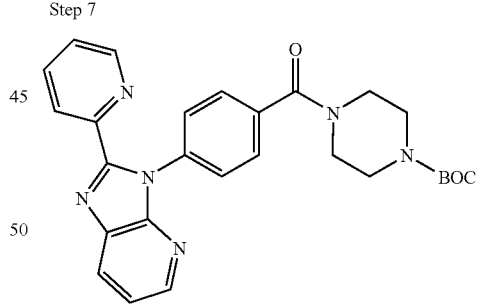
106

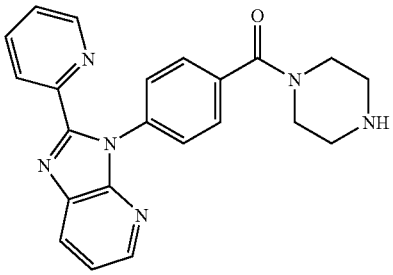
107

To a solution of compound 106 (1.3 g, 2.7 mmol) in CH₂Cl₂ (20 mL) was added CF₃COOH (6 mL). The resulting reaction was allowed to stir at room temperature for 20 h, after which time concentrated NH₄OH was added until the solution was at pH 11-12. The resulting mixture was extracted with CH₂Cl₂, washed with brine, dried over Na₂SO₄, filtered, and concentrated in vacuo to provide compound 107. Yield: 1.0 g, 96%.

Step 8

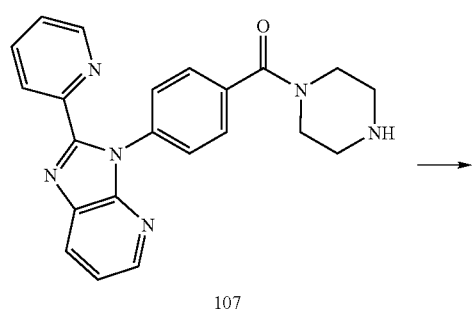

107

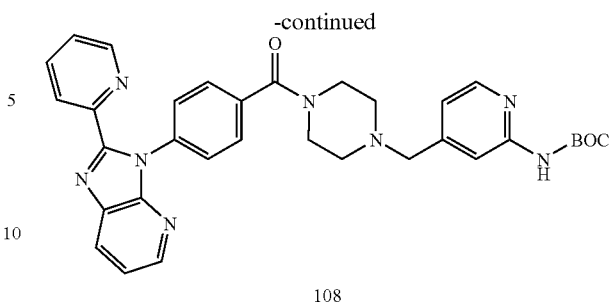

108

To a solution of compound 107 (0.2 g, 0.52 mmol) and N-Boc-2-aminopyridine-4-carbaldehyde (see WO2002032893) (0.14 g, 0.62 mmol) in CH₂Cl₂ (10 mL) was added Na(OAc)₃BH (0.44 g, 2.08 mmol). The resulting reaction was allowed to stir at room temperature for 20 h. The reaction mixture was then extracted with CH₂Cl₂ and the organics were washed with saturated NaHCO₃ aqueous solution then brine, dried over Na₂SO₄, and concentrated in vacuo. The resulting residue was purified using flash chromatography to provide compound 108. Yield: 0.11 g, 36%.

Step 9

Compound 108 was converted to Compound 82A using the method described in step 7 of this example. MH⁺ 491

Using the methods set forth above, compounds 83A-112A were prepared:

| Compound | Structure | (M + H)⁺ |
|---|---|---|
| 83A | 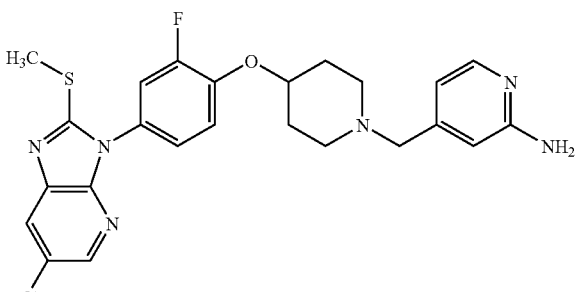 | 499 |
| 84A | 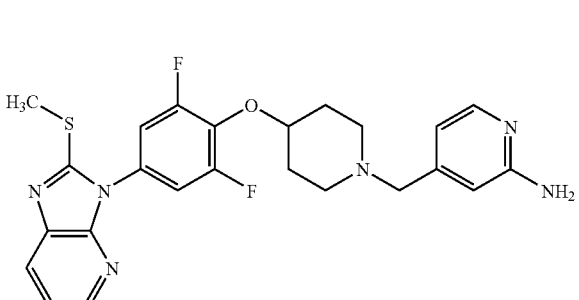 | 517 |

| Compound | Structure | (M + H)+ |
|---|---|---|
| 85A | 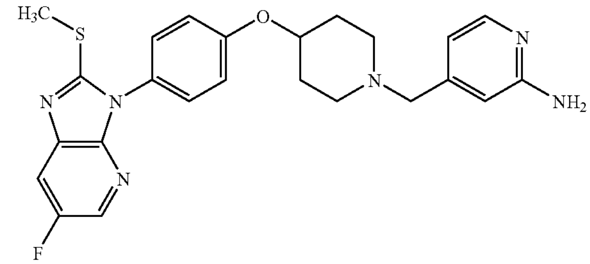 | 465 |
| 86A | 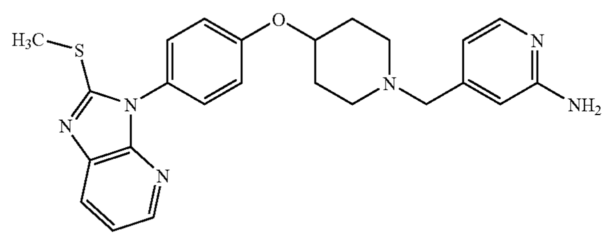 | 445 |
| 87A | 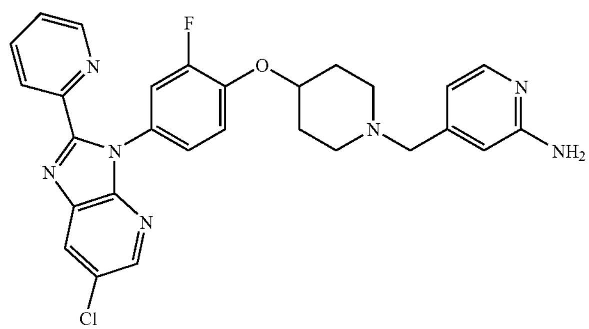 | 530 |
| 88A | 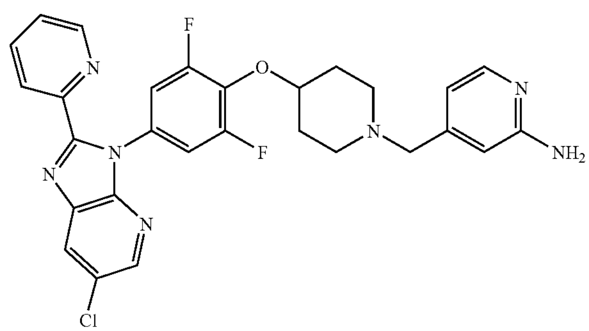 | 548 |
| 89A | 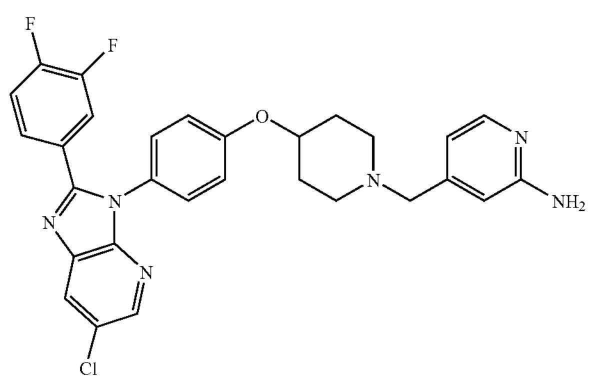 | 547 |

-continued

| Compound | Structure | (M + H)+ |
|---|---|---|
| 90A | 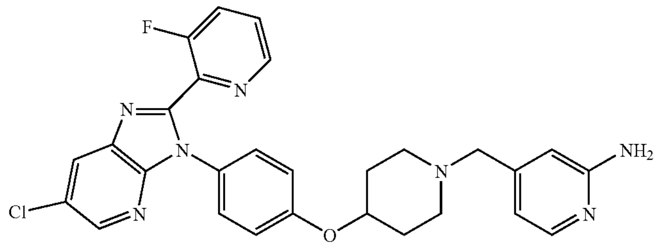 | 530 |
| 91A | 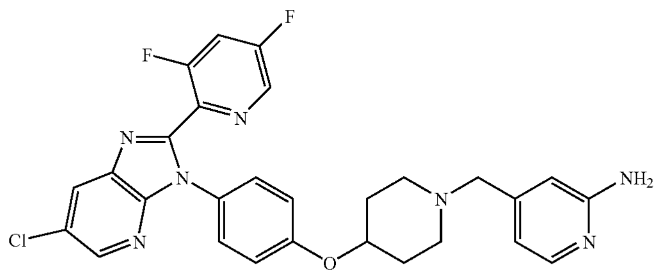 | 548 |
| 92A | 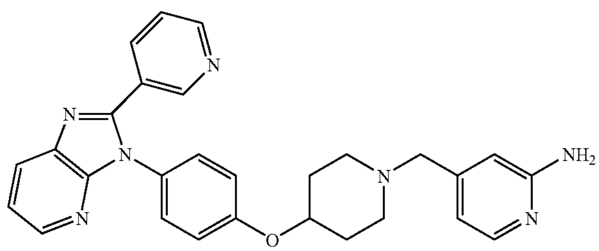 | 478 |
| 93A | 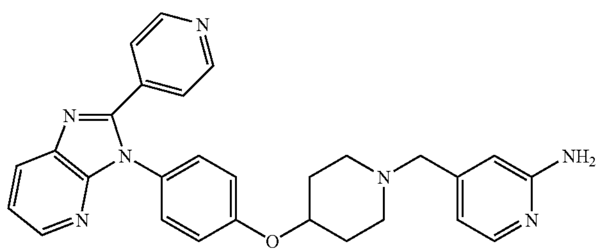 | 478 |
| 94A | 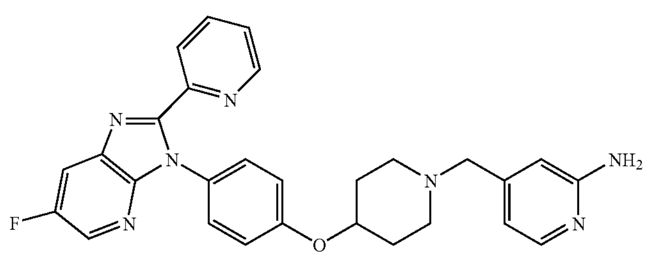 | 496 |
| 95A | 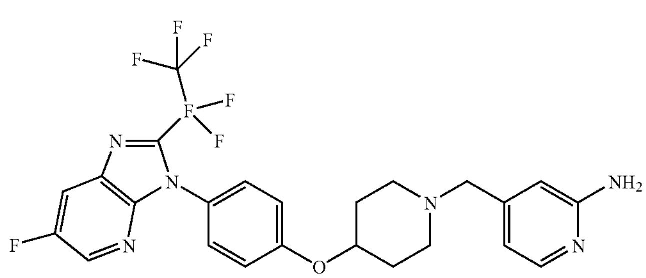 | 537 |

-continued

| Compound | Structure | (M + H)+ |
|---|---|---|
| 96A | 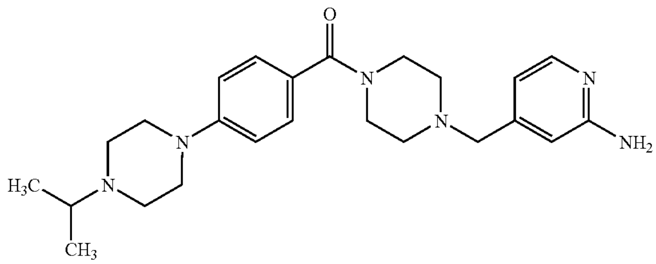 | 423 |
| 97A | 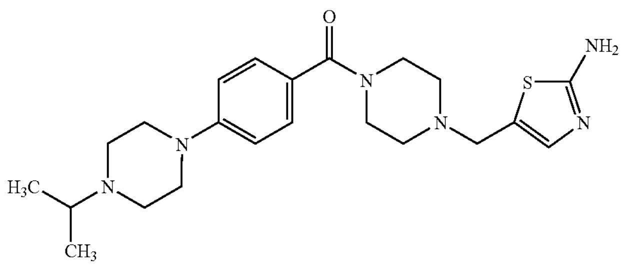 | 429 |
| 98A | 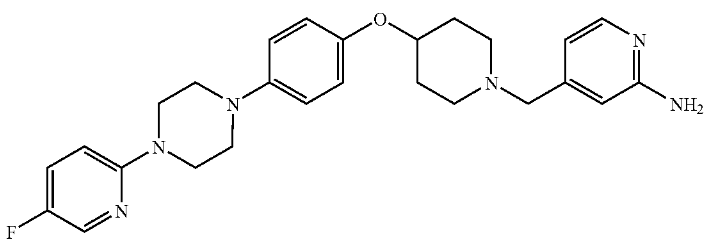 | 463 |
| 99A | 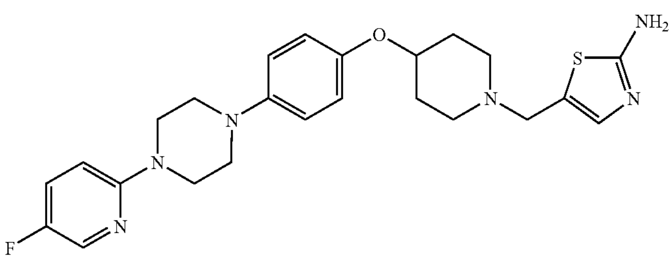 | 469 |
| 100A | 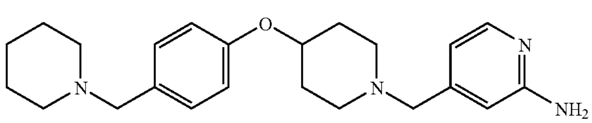 | 381 |
| 101A | 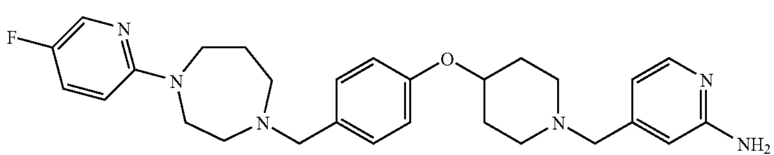 | 491 |
| 102A | 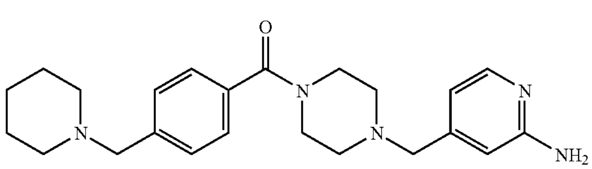 | 394 |

-continued

| Compound | Structure | (M + H)+ |
|---|---|---|
| 103A | 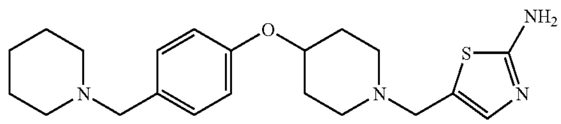 | 387 |
| 104A | 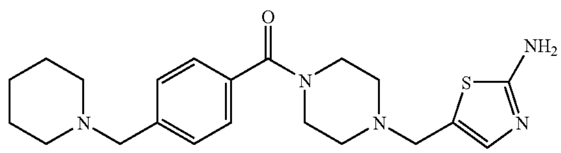 | 400 |
| 105A | 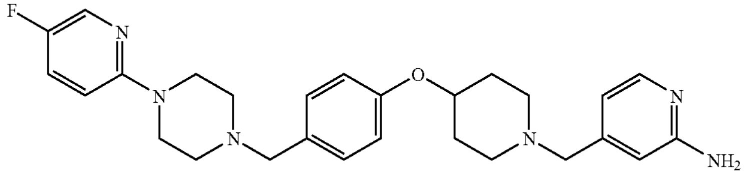 | 477 |
| 106A | 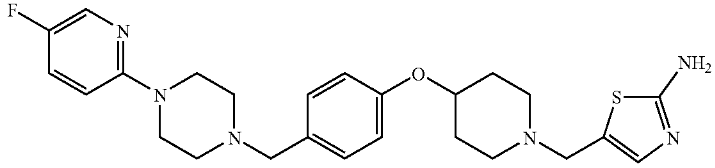 | 483 |
| 107A | 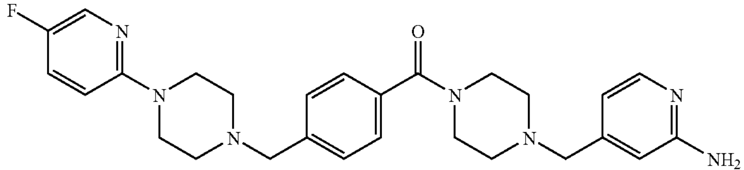 | 490 |
| 108A | 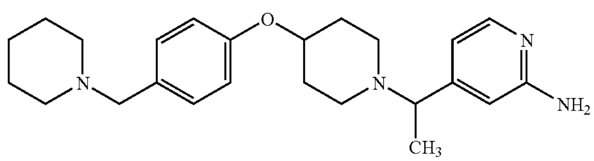 | 395 |
| 109A | 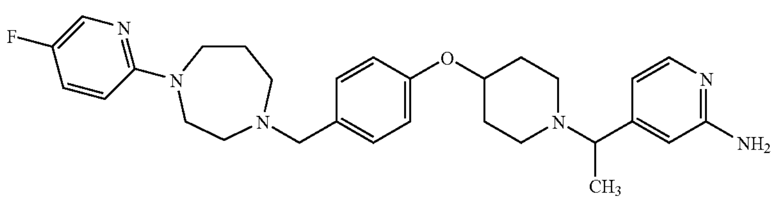 | 505 |
| 110A | 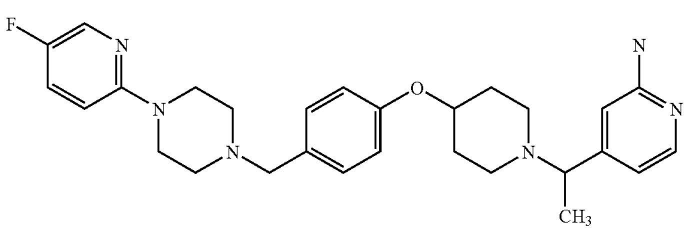 | 491 |

| Compound | Structure | (M + H)+ |
|---|---|---|
| 111A | 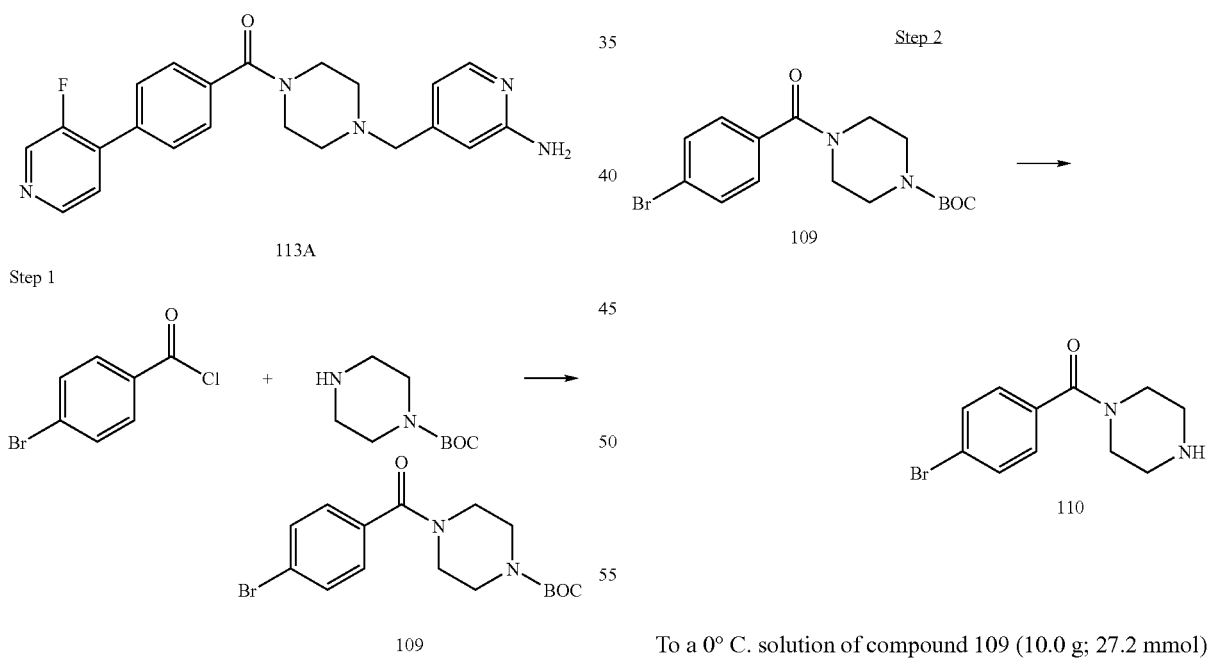 | 505 |
| 112A | 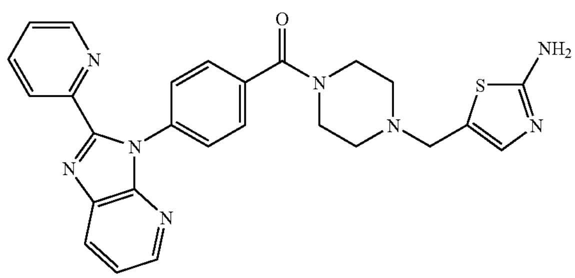 | 497 |

Example 36

Preparation of Compound 113A

Step 1

To a 0° C. solution of 4-bromobenzoyl chloride (11.0 g; 50 mmol) in 200 mL of $CH_2Cl_2$ was added 1-Boc-piperazine (9.3 g; 50 mmol), followed by $Et_3N$ (20.9 mL; 150 mmol). The reaction was allowed to stir at 0° C. for about 1 hour, then at room temperature for 3 hours. The reaction mixture was concentrated in vacuo and the resulting residue was partitioned between ethyl acetate and water. The organic phase was washed with water, then brine, dried over $MgSO_4$ and concentrated in vacuo. The crude product obtained was purified using flash chromatography to provide intermediate compound 109 (15.8 g).

Step 2

To a 0° C. solution of compound 109 (10.0 g; 27.2 mmol) in 60 mL of $CH_2Cl_2$ was added dropwise TFA (15 mL). The reaction was allowed to stir at 0° C. for about 1 hour, then at room temperature for 3 hours. The reaction mixture was concentrated in vacuo and the resulting residue was partitioned between ethyl acetate and aqueous $NaHCO_3$. The organic phase was washed with saturated aqueous $NaHCO_3$ and brine, then was dried and concentrated in vacuo to provide intermediate compound 110 (4.6 g), which was used without purification.

113

Step 3

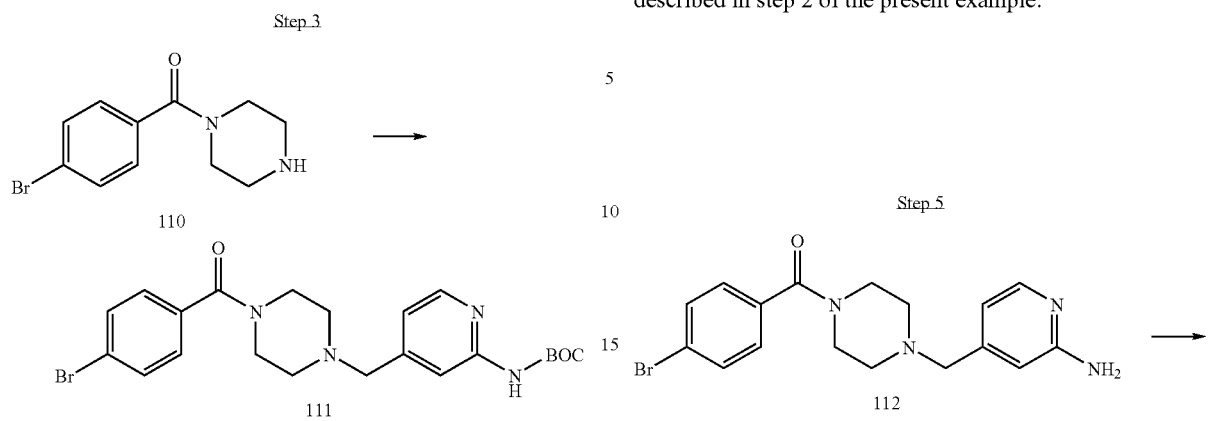

Compound 110 was converted to 111 by using the method described in Example 35, step 8.

Step 4

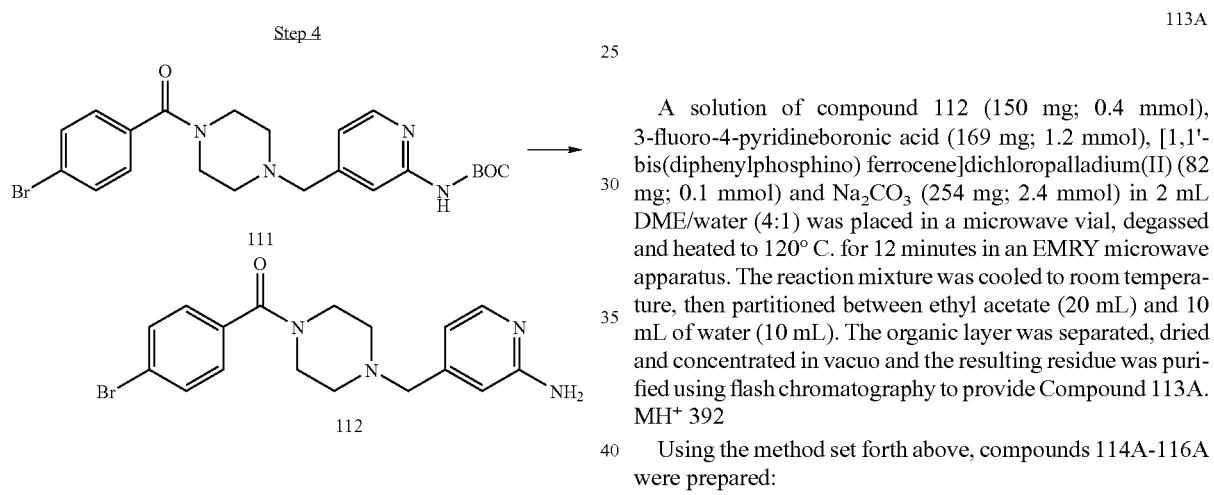

114

Compound 111 was converted to 112 by using the method described in step 2 of the present example.

Step 5

113A

A solution of compound 112 (150 mg; 0.4 mmol), 3-fluoro-4-pyridineboronic acid (169 mg; 1.2 mmol), [1,1'-bis(diphenylphosphino) ferrocene]dichloropalladium(II) (82 mg; 0.1 mmol) and $Na_2CO_3$ (254 mg; 2.4 mmol) in 2 mL DME/water (4:1) was placed in a microwave vial, degassed and heated to 120° C. for 12 minutes in an EMRY microwave apparatus. The reaction mixture was cooled to room temperature, then partitioned between ethyl acetate (20 mL) and 10 mL of water (10 mL). The organic layer was separated, dried and concentrated in vacuo and the resulting residue was purified using flash chromatography to provide Compound 113A. $MH^+$ 392

Using the method set forth above, compounds 114A-116A were prepared:

| Compound | Structure | $(M + H)^+$ |
|---|---|---|
| 114A | 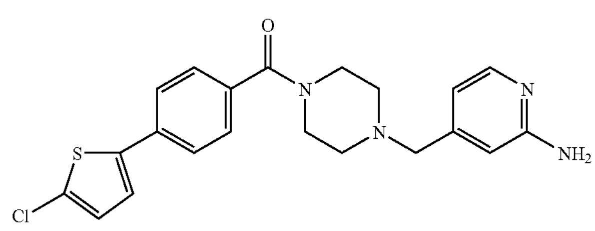 | 413 |
| 115A | 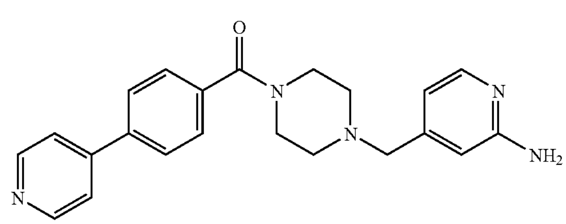 | 374 |

-continued

| Compound | Structure | (M + H)+ |
|---|---|---|
| 116A | 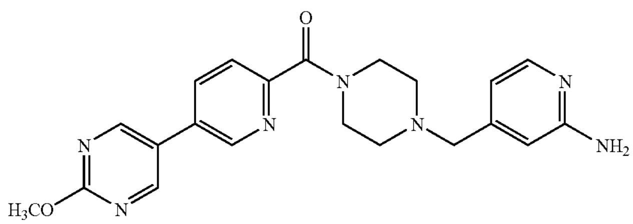 | 406 |

Example 37

General Procedure for H₃-Receptor Binding Assay

The source of the $H_3$ receptors in this experiment was guinea pig brain. Alternatively, the source of $H_3$ receptors was recombinant human receptor, expressed in HEK-293 (human embryonic kidney) cells.

The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein, 5 μg in the case of recombinant human receptor) to the reaction tubes. The reaction was started by the addition of 3 nM [³H]R-α-methyl histamine (8.8 Ci/mmol) or 3 nM [³H]Nα-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula (I) have a $K_i$ within the range of about 0.6 to about 600 nM at the recombinant human $H_3$ receptor and from about 18 nM to about 400 nM at the guinea pig brain receptor. Compound 69A has a $K_i$ of 0.6 nM the recombinant human receptor assay and a $K_i$ of 18 nM in the guinea pig receptor assay.

Example 38

Effects of the Compounds of the Invention on Diet-Induced Obesity in Mice

Lean mice (male, approx. 5 weeks of age, purchased from The Jackson Laboratory, Bar Harbor, Me.) were maintained in individual cages at 22° C. on a 12:12 hr light/dark cycle. The "treated" mice (N=12) were administered a Thiazole Derivative (10 mg/kg) by gavage once daily for four consecutive days. Control mice (N=12) were administered vehicle only, once daily for four days. Both control and treated mice were fed a high-fat diet from days 0 to 4 and body weight and food intake was monitored daily. The percent inhibition for weight gain and food intake was calculated by comparing the increase in weight gain and food intake in the treated mice to the increase in weight gain and food intake in the control mice.

Table 1 shows the effects of illustrative compounds of the invention on diet-induced obesity in mice. Compound numbers correspond to the compound numbering set forth in the specification.

TABLE 1

| Compound No. | Weight Gain Inhibition (%) | Food intake Inhibition (%) |
|---|---|---|
| 4A | 74.1 | 15.9 |
| 22A | 42.4 | 11.2 |
| 36A | 58.0 | 12.7 |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound having the formula:

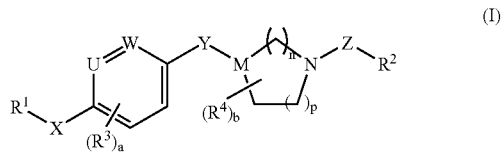

(I)

or a pharmaceutically acceptable salt thereof, wherein:
a is 0, 1, 2, 3 or 4;
b is 0, 1, 2 or 3;
M is CH, n is 2, and p is 1;
U and W are each CH;
X is a bond, alkylene, —C(O)—, —C(N—OR⁵)—, —C(N—OR⁵)—CH(R⁶)—, —CH(R⁶)—C(N—OR⁵)—, —O—, —OCH₂—, —CH₂O—, —CH(OH)—, —S—, —S(O)— or —S(O)₂—;
Y is —O—, —CH₂—, —(CH₂)₂—, —C(=O)—, —C(=NOR⁷)—, —S—, —S(O)— or —SO₂—;

Z is a bond, —CH($R^9$)—($R^{10}$—$C_1$-$C_5$ alkylene)-, —CH($R^9$)—CH($R^9$)—O—, —CH($R^9$)—CH($R^9$)—N—, —CH($R^9$)—C($R^{9a}$)=C($R^{9a}$— or —CH($R^9$)—C($R^{9a}$)=C($R^{9a}$)—($R^{10}$—$C_1$-$C_3$ alkylene)-;

$R^1$ is $R^{11}$-(6-membered heteroaryl),

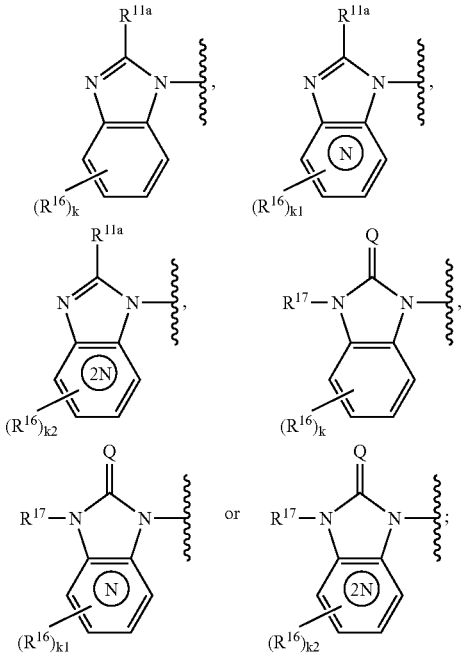

provided that when $R^1$ is attached to X by a nitrogen atom, X is a bond or alkylene;

k is 0, 1, 2, 3 or 4;
k1 is 0, 1, 2 or 3;
k2 is 0, 1 or 2;
Q is O or S;
$R^2$ is $R^{13}$-alkyl-, $R^{13}$-alkenyl-$R^{13}$-aryl-, $R^{13}$-arylalkyl-, $R^{13}$-heteroaryl-, $R^{13}$-heteroarylalkyl-, $R^{13}$-cycloalkyl- or $R^{13}$-heterocycloalkyl-;
each $R^3$ is independently selected from the group consisting of H, alkyl, halo, —OH, alkoxy, —$CF_3$, —$OCF_3$, —$OCHF_2$, —$NO_2$, —$CO_2R^{14}$, —$N(R^{14})_2$, —CON($R^{14})_2$, —NHC(O)$R^{14}$, —NHSO$_2R^{14}$, —SO$_2N(R^{14})_2$ and —CN;
each $R^4$ is independently selected from the group consisting of H, halo, alkyl, haloalkyl, —OH, alkoxy, —$CF_3$ and —CN;
$R^5$ is H, alkyl, haloalkyl, $R^{15}$-aryl-, $R^{15}$-heteroaryl-, $R^{15}$-cycloalkyl-, $R^{15}$-heterocycloalkyl-, $R^{15}$-arylalkyl-, —$CF_3$ or —$CH_2CF_3$;
$R^6$ is H or alkyl;
$R^7$ is H, alkyl, haloalkyl, $R^{15}$-aryl- or $R^{15}$-heteroaryl-;
$R^9$ is independently selected from the group consisting of H, alkyl and haloalkyl;
$R^{9a}$ is independently selected from the group consisting of H, fluoro, alkyl and haloalkyl;
$R^{10}$ is 1, 2 or 3 substituents independently selected from the group consisting of H, $R^{15}$-cycloalkyl-, $R^{15}$-heterocycloalkyl-, $R^{15}$-aryl, $R^{15}$-heteroaryl-, halo, haloalkyl, —CN, —OH, alkoxy —$OCF_3$, —$NO_2$, and N($R^6)_2$;
$R^{11}$ is 1, 2, 3 or 4 substituents independently selected from the group consisting of H, halo, alkyl, haloalkyl, —OH, alkoxy, alkylthio, $R^{15}$-cycloalkyl-, $R^{15}$-heterocycloalkyl-, $R^{15}$-aryl-, $R^{15}$-arylalkyl-, $R^{15}$-heteroaryl-, $R^{15}$-heteroarylalkyl-, aryloxy, —$OCF_3$, —$OCHF_2$, —$NO_2$, —$CO_2R^{12}$, —$N(R^{12})_2$, —CON($R^{12})_2$, —NHC(O)$R^{12}$, —NHSO$_2R^{12}$, —SO$_2N(R^{12})_2$ and —CN;

$R^{11a}$ is H, alkyl, haloalkyl, alkoxy, alkylthio, $R^{15}$-cycloalkyl, $R^{15}$-heterocycloalkyl-, $R^{15}$-aryl-, $R^{15}$-cycloalkyl-, $R^{15}$-heterocycloalkyl-, $R^{15}$-heteroaryl-, $R^{15}$-heteroarylalkyl-, $R^{15}$-aryloxy-, —$OCF_3$, —$OCHF_2$, —$N(R^{12})_2$ or —$SCF_3$;

$R^{12}$ is independently selected from the group consisting of H, alkyl, haloalkyl, $R^{15}$-aryl-, $R^{15}$-heteroaryl, $R^{15}$-arylalkyl-, $R^5$-cycloalkyl- and $R^{15}$-heterocycloalkyl-;

$R^{13}$ is 1, 2 or 3 substituents independently selected from the group consisting of H, halo, alkyl, haloalkyl, —OH, alkoxy, $R^{15}$-aryl-, $R^{15}$-aryloxy-, —$OCF_3$, —$OCHF_2$, —$NO_2$, —$CO_2R^{14}$, —$N(R^{14})_2$, —CON($R^{14})_2$, —NHC(O)$R^{14}$, —NHSO$_2R^{14}$, —SO$_2N(R^{14})_2$ and —CN;

$R^{14}$ is independently selected from the group consisting of H, alkyl, haloalkyl, $R^{15}$-aryl-, $R^{15}$-heteroaryl, $R^{15}$-cycloalkyl- and $R^{15}$-heterocycloalkyl-;

$R^{15}$ is 1, 2 or 3 substituents independently selected from the group consisting of H, alkyl, halo, haloalkyl, alkoxy, —$N(R^{18})_2$, -alkylene-$N(R^{18})_2$, —CN, —$OCF_3$ and —$OCHF_2$;

$R^{16}$ is independently selected from the group consisting of alkyl, halogen, haloalkyl, alkenyl, OH, alkoxy, —$SO_{0-2}$-alkyl and —$OCF_3$;

$R^{17}$ is H, alkyl, hydroxyl-substituted($C_7$-$C_6$)alkyl, haloalkyl-, haloalkoxyalkyl-, alkoxyalkyl-, $R^{15}$-aryl-, $R^{15}$-arylalkyl-, $R^{15}$-heteroaryl-, $R^{15}$-heteroarylalkyl-, $R^{15}$-cycloalkyl- or $R^{15}$-cycloalkylalkyl-; and $R^{18}$ is independently selected from the group consisting of H and alkyl.

2. The compound of claim 1 wherein X is a single bond or C(N—O$R^5$)— and wherein $R^5$ is H or alkyl.

3. The compound of claim 1 wherein Y is —O— or —C(=O)—.

4. The compound of claim 1 wherein Z is $C_1$-$C_3$ alkylene, —CH($R^9$)—($R^{10}$—$C_1$-$C_5$ alkylene)-, —CH($R^9$)—C($R^{9a}$)=C($R^{9a}$)—, —(CH$_2)_2$—O— or $C_1$-$C_3$ alkylene interrupted by a cycloalkylene group, wherein $R^9$ and $R^{9a}$ are each H, and $R^{10}$ is halo.

5. The compound of claim 4 wherein Z is —CH$_2$—, —(CH$_2)_3$—, —CH$_2$—CH=CH—, —(CH$_2)_2$—CH(F)—, —CH$_2$—CH(F)—CH$_2$—, —(CH$_2)_2$—O— or

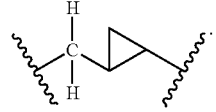

6. The compound of claim 1 wherein M is CH, n is 2, p is 1, a and b are each 0, X is a single bond or —C(N—O$R^5$)—, Y is —O—, and Z is —CH$_2$—.

7. The compound of claim 1 wherein $R^2$ is a 5- or 6-membered $R^{13}$-heteroaryl- or a 4, 5 or 6-membered $R^{13}$-heterocycloalkyl-.

8. The compound of claim 7 wherein $R^2$ is selected from the group consisting of $R^{13}$-pyridyl-, $R^{13}$-pyrimidyl-, $R^{13}$-pyradazinyl, $R^{13}$-tetrahydropyranyl-, $R^{13}$-azetidinyl-$R^{13}$-oxazolyl- and $R^{13}$-thiazolyl-, wherein $R^{13}$ is 1 or 2 substituents independently selected from the group consisting of H, —$CH_3$, —$NH_2$ and —$NHCH_3$.

9. The compound of claim 8 wherein $R^2$ is 2-amino pyridyl, 2-amino oxazolyl, 2-amino thiazolyl, 1-methyl-azetidinyl or tetrahydropyranyl.

10. The compound of claim 1 wherein $R^1$ is $R^{11}$-(6-membered heteroaryl)-,

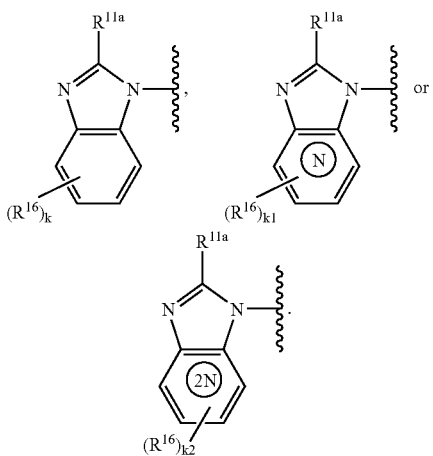

11. The compound of claim 10 wherein $R^1$ is $R^{11}$-pyridyl-, and $R^{11}$ is 1 to 4 substituents independently selected from the group consisting of H, halo, alkyl, haloalkyl and —CN.

12. The compound of claim 1 wherein $R^1$ is

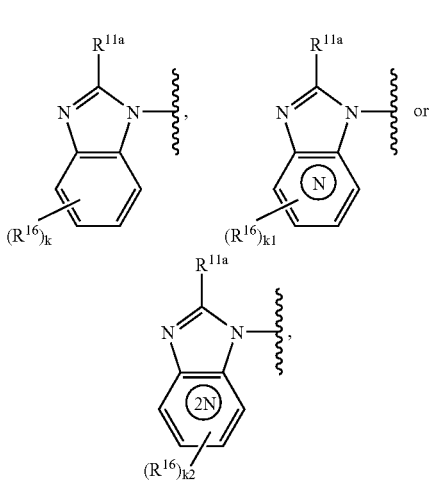

wherein $R^{11a}$ is $C_1$-$C_3$ alkyl, halo($C_1$-$C_3$)alkyl, $C_1$-$C_3$ alkoxy, $C_1$-$C_3$ alkylthio, $R^{15}$-phenyl- or $R^{15}$-pyridyl-; $R^{15}$ is 1-3 substituents independently selected from H, halo, alkyl, haloalkyl, —OCF$_3$, and —CUB; and k, k1 and k2 are each 0, 1 or 2.

13. The compound of claim 12 wherein $R^1$ is

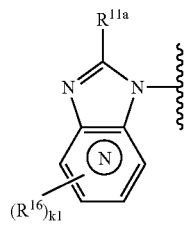

wherein $R^{11a}$ is ($C_1$-$C_3$)alkyl, $C_1$-$C_3$ alkoxy, $C_1$-$C_3$ alkylthio, $R^{15}$-phenyl- or pyridyl-; $R^{15}$ is 1 or 2 substituents independently selected from H, halo, alkyl and haloalkyl; and k1 is 0 or 1.

14. The compound of claim 13 wherein $R^1$ is

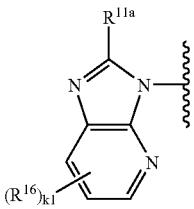

wherein $R^{11a}$ is —$C_2F_5$, —$CF_3$, $C_2H_5$—O—, $CH_3$—O—, $C_2H_5$—S—, $CH_3$—S—, $R^{15}$-phenyl- or $R^{15}$-pyridyl-; $R^{15}$ is 1 or 2 substituents independently selected from H, F, Cl, —CH$_3$, and —CF$_3$; and (i) k1 is 0, or (ii) k1 is 1 and $R^{16}$ is H, F, Cl or —CF$_3$.

15. A compound having the structure:

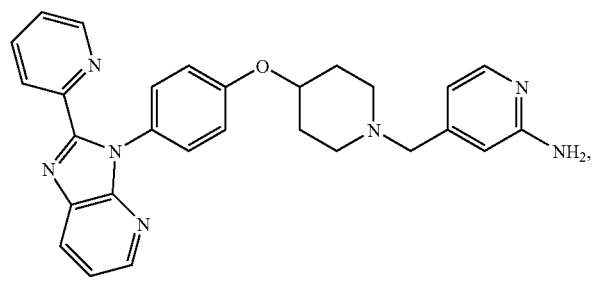
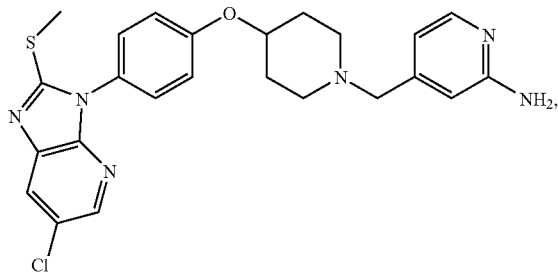

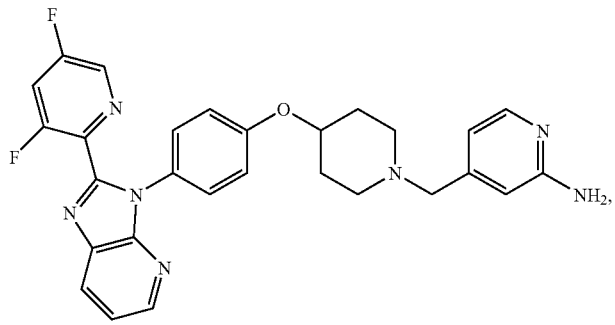
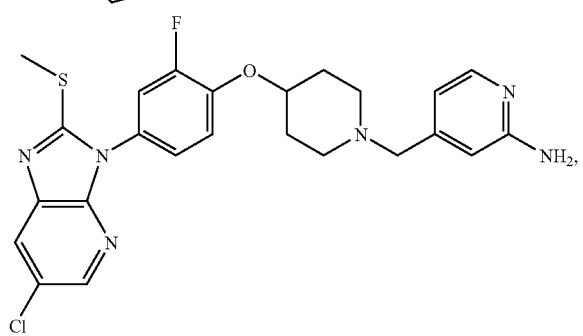
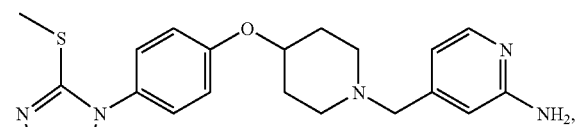
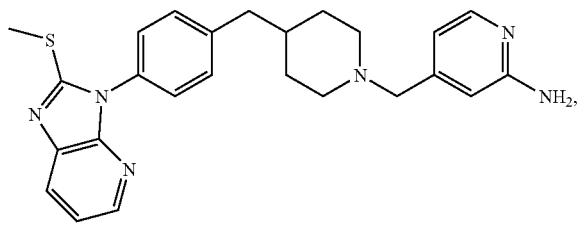
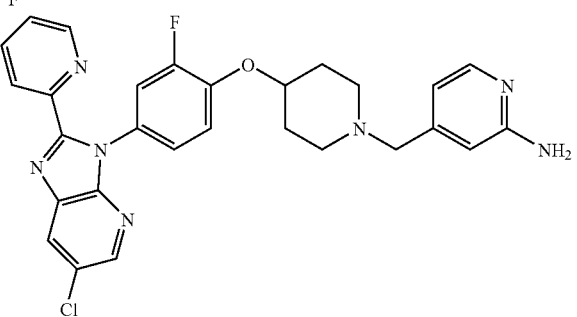
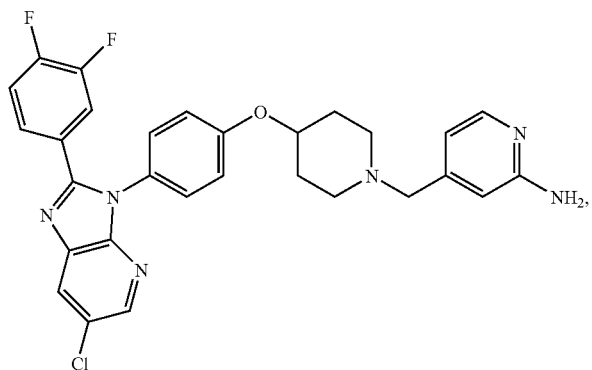
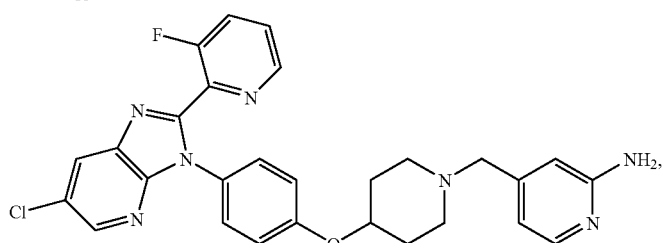
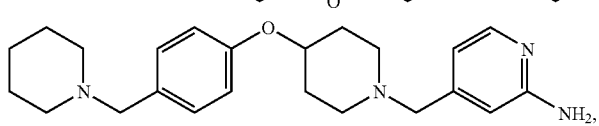

-continued
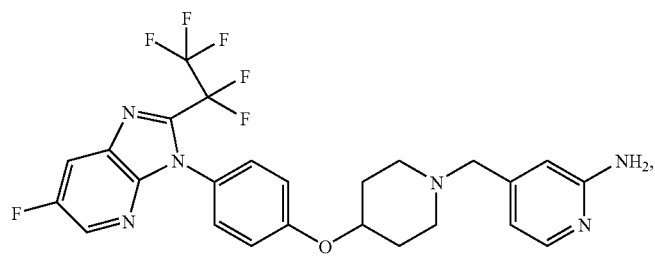
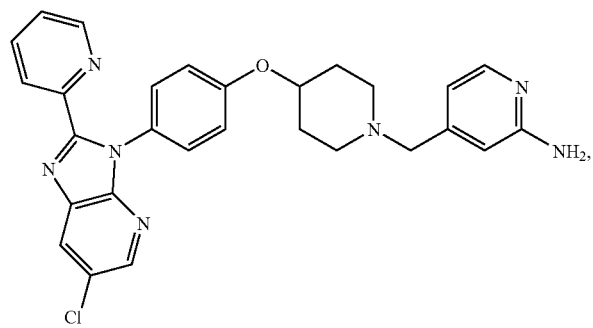
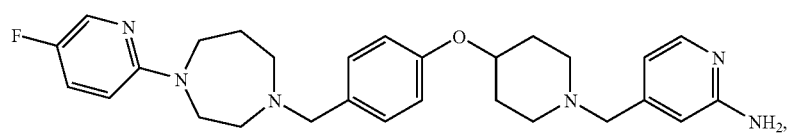
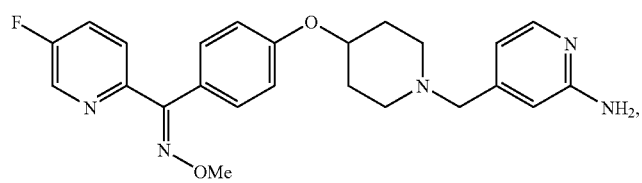
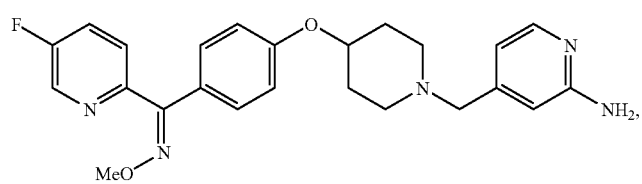
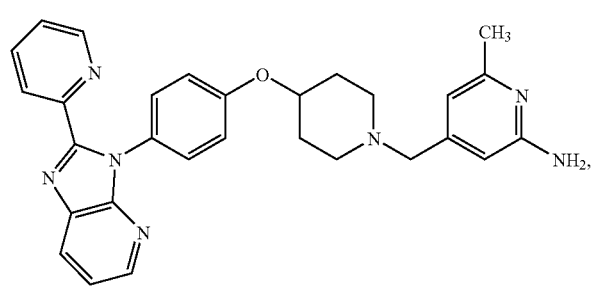
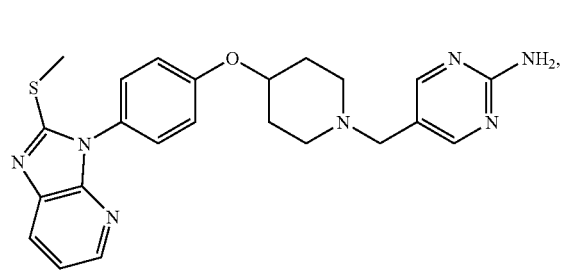
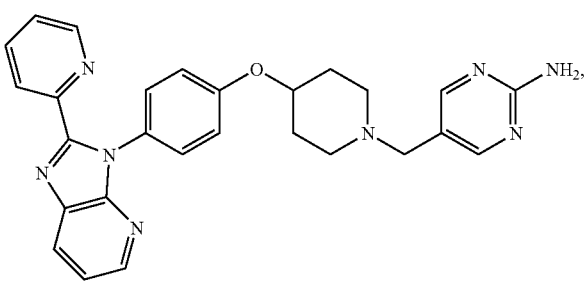

-continued
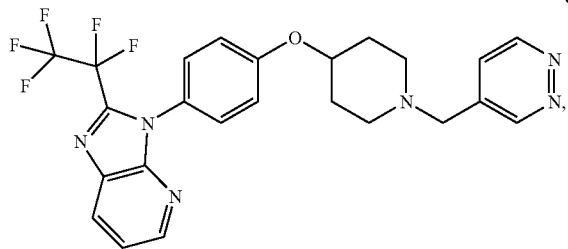
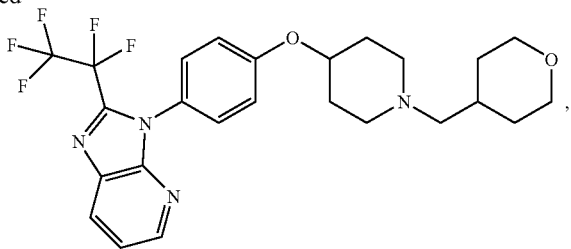
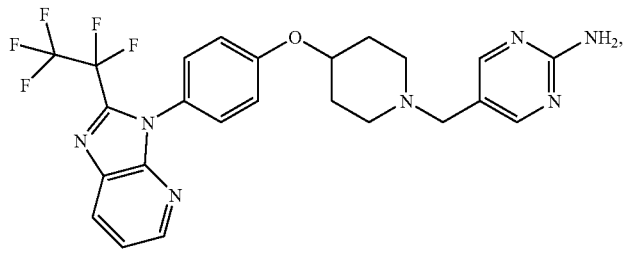
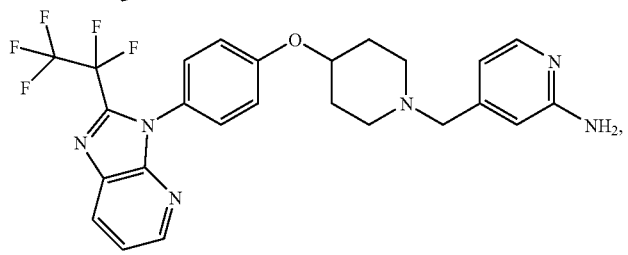
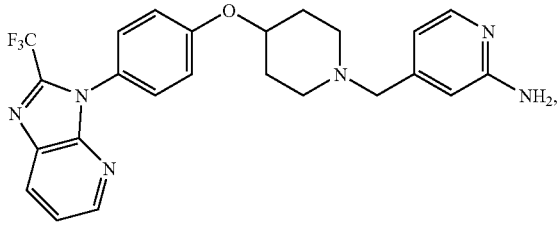
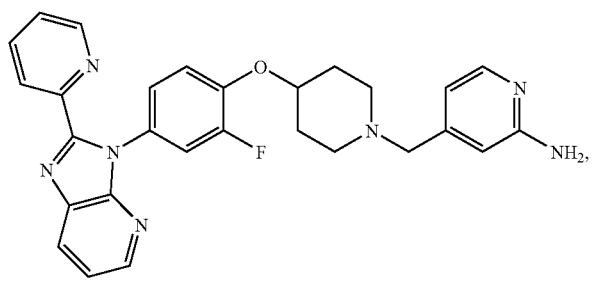
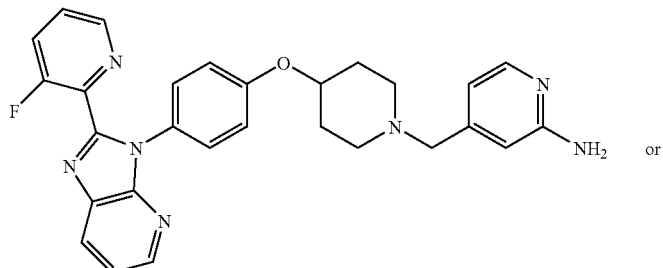 or
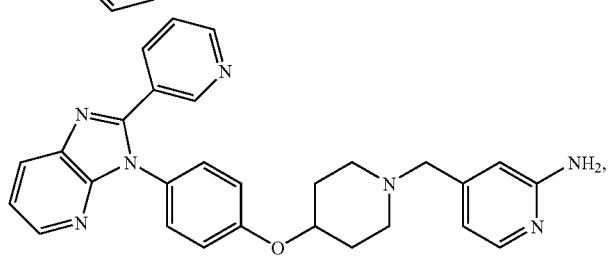
or a pharmaceutically acceptable salt thereof.

16. A pharmaceutical composition comprising an effective amount of at least one compound of claim 1 and a pharmaceutically acceptable carrier.

17. A pharmaceutical composition comprising an effective amount of at least one compound of claim 15 and a pharmaceutically acceptable carrier.

18. A compound having the formula:

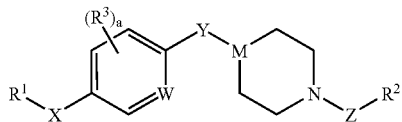

(IA)

or a pharmaceutically acceptable salt thereof, wherein
M is CH;
W is CH;
X is a single bond, —CH$_2$—, —C(O)—, —C(=NOR)—, —CH(OH)—;
Y is —O—, —S—, —SO$_2$—, —C(O)— or —CH$_2$;
Z is a single bond;
R$^1$ is 6-membered heteroaryl,

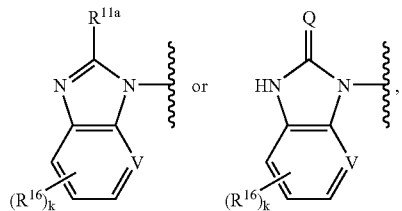

and a 6-membered heteroaryl group can be substituted with up to 2 groups chosen from halo, alkyl and alkoxy;
R$^2$ is heterocycloalkyl, -heteroaryl, —CH(G)-aryl, —CH(G)-heteroaryl,

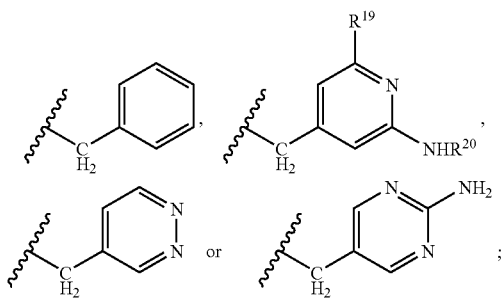

each occurrence of R$^3$ is independently halo;
R11$^a$ is —H, —S-alkyl, heteroaryl, aryl, —CF$_2$(CF$_3$) or —CF$_3$;
R$^{16}$ is —H, halo, —C$_1$-C$_6$ alkyl; or alkenyl;
R$^{19}$ is —H or alkyl;
R$^{20}$ is —H or -alkyl;
G is —H or -alkyl;
Q is O or S;
V is CH or N;
a is 0, 1 or 2; and
k is 0 or 1.

* * * * *

UNITED STATES PATENT AND TRADEMARK OFFICE
CERTIFICATE OF CORRECTION

PATENT NO. : 7,638,531 B2
APPLICATION NO. : 11/641175
DATED : December 29, 2009
INVENTOR(S) : Mutahi et al.

It is certified that error appears in the above-identified patent and that said Letters Patent is hereby corrected as shown below:

Claim 1, column 118, line 12, delete "$R^5$-cycloalkyl-" and replace with "$R^{15}$-cycloalkyl-"

Claim 1, column 118, line 29, delete "$(C_7-C_6)$" and replace with "$(C_2-C_6)$"

Claim 2, column 118, line 36, insert "–" in front of "$C(N-OR^5)$-"

Claim 8, column 118, lines 64-65, delete "$R^{13}$-azetidinyl-$R^{13}$-oxazolyl-" and replace with "$R^{13}$-azetidinyl-, $R^{13}$-oxazolyl-"

Claim 12, column 120, line 4, delete "-CUB" and replace with "-$CHF_2$"

Claim 13, column 120, line 20, delete "pyridyl-;" and replace with "$R^{15}$-pyridyl-;"

Signed and Sealed this

Eighteenth Day of May, 2010

David J. Kappos
*Director of the United States Patent and Trademark Office*